US012797352B2

(12) United States Patent
Strupp

(10) Patent No.: US 12,797,352 B2
(45) **Date of Patent: *Nov. 17, 2026**

(54) THERAPEUTIC AGENTS FOR NEURODEGENERATIVE DISEASES

(71) Applicant: INTRABIO LIMITED, London (GB)

(72) Inventor: Michael Strupp, Munich (DE)

(73) Assignee: IntraBio Limited, London (GB)

( * ) Notice: Subject to any disclaimer, the term of this patent is extended or adjusted under 35 U.S.C. 154(b) by 758 days.

This patent is subject to a terminal disclaimer.

(21) Appl. No.: 18/183,972

(22) Filed: Mar. 15, 2023

(65) Prior Publication Data

US 2023/0210799 A1 Jul. 6, 2023

Related U.S. Application Data

(62) Division of application No. 16/324,353, filed as application No. PCT/IB2017/054929 on Aug. 11, 2017, now Pat. No. 12,144,792.

(30) Foreign Application Priority Data

Aug. 11, 2016 (GB) ..................................... 1613829
Feb. 16, 2017 (GB) ..................................... 1702551
Apr. 10, 2017 (GB) ..................................... 1705766
Apr. 28, 2017 (GB) ..................................... 1706867

(51) Int. Cl.
*A61K 31/198* (2006.01)
*A61P 25/28* (2006.01)

(52) U.S. Cl.
CPC ............ *A61K 31/198* (2013.01); *A61P 25/28* (2018.01)

(58) Field of Classification Search
CPC .......... A61P 25/28; A61P 21/00; A61P 25/00; A61P 25/02; A61P 25/14; A61P 25/16; A61K 31/198; A61K 31/13; C07C 233/46
See application file for complete search history.

(56) References Cited

U.S. PATENT DOCUMENTS

2006/0063827 A1 3/2006 Yu et al.
2008/0214649 A1 9/2008 Yu et al.
2009/0318555 A1 12/2009 Fabre
2013/0317036 A1 11/2013 Rekik

FOREIGN PATENT DOCUMENTS

CN 103079550 A 5/2013
JP 2013527222 A 6/2013
JP 2013544275 A 12/2013
WO WO 2006/036634 A2 4/2006
WO WO2011/151685 A1 12/2011

OTHER PUBLICATIONS

Verma, S., "Is the Era of One-Size-Fits-All Alzheimer's Treatment Officially Over?", J Mol Neurosci 76, 3 (2026), pp. 1-30.*

Gu, "Mapping of the Insomnia Severity Index and other sleep measures to EuroQol EQ-5D health state utilities", Health Qual Life Outcomes 9, 119 (2011), pp. 1-13.*

Strupp et al. (Effects of acetyl-DL-leucine in patients with cerebellar ataxia: a case series. *J Neural.* Oct. 2013;260(10):2556-61. doi: 10.1007/s00415-013-7016-x. Epub Jul. 9, 2013. PMID: 23835634; PMCID: PMC3824630.).

Brueggemann et al. (Effects of Acetyl-DL-Leucine on Ataxia and Downbeat-Nystagmus in Six Patients With Ataxia Telangiectasia. *J Child Neural.* Jan. 2022;37(1 ):20-27. doi: 10.1177/08830738211028394. Epub Oct. 7, 2021.).

Churchill et al. (Acetylation turns leucine into a drug by membrane transporter switching. Sci Rep. Aug. 4, 2021;11(1):15812. doi: 10.1038/s41598-021-95255-5. PMID: 34349180; PMCID: PMC8338929.).

Bremova et al., "Acetyl-DL-leucine in Niemann-Pick type C: A case series," Neurology, vol. 85, No. 16, pp. 1368-1375, Oct. 20, 2015.

International Search Report & Written Opinion dated Nov. 10, 2017, PCT/IB2017/054929.

Schniepp et al., "Acetyl-DL-leucine improves gait variability in patients with cerebellar ataxia-a case series," Cerebellum & Ataxias, vol. 3, p. 8, Apr. 12, 2016.

Miyazaki et al., A case of cyclic ataxia in which 4-aminopyridine was effective, Neurological Therapeutics, 2005, 3:350.

Special Issue: Pharmacotherapy, Guidance, and Management of Chronic Diseases, Medicine and Pharmacy, 1987, 17 (5) (7 pages).

Yabe I, Drug therapy for spinocerebellar degeneration, Journal of Clinical and Experimental Medicine, 2015, 255 (10):1062-1066.

Shuli Sheng, Alzheimer's Disease and Related Disorders, Scientific Technology Document Press, Apr. 30, 2006, pp. 559, 565.

* cited by examiner

*Primary Examiner* — Sahar Javanmard
(74) *Attorney, Agent, or Firm* — Finnegan, Henderson, Farabow, Garrett & Dunner, LLP

(57) ABSTRACT

The present disclosure provides for treating neurodegenerative diseases comprising administering acetyl-leucine or a pharmaceutically acceptable salt thereof.

18 Claims, 31 Drawing Sheets

| | HEXB-/- UNTREATED | HEXB-/- ACETYL-DL-LEUCINE 0.1g/kg |
|---|---|---|
| MEDIAN SURVIVAL | 112 | 120 |

| | BLUE | PINK |
|---|---|---|
| <\|>3 SD | | |
| <\|>2 SD | | |
| <\|>1 SD | | |

BEFORE TREATMENT

| | FAP | VELOCITY (cm/s) | CAD (STEPS/MIN) | $BoS_L$ (cm) | $BoS_R$ (cm) | $SLen_L$ (cm) | $SLen_R$ (cm) | $STIME_L$ (s) | $STIME_R$ (s) | $DSUPP_L$ (%) | $DSUPP_R$ (%) | $SWING_L$ (%) | $SWING_R$ (%) | $STANCE_L$ (%) | $STANCE_R$ (%) | BoS $CV_L$ (%) | BoS $CV_R$ (%) | SLen $CV_L$ (%) | SLen $CV_R$ (%) | STIME $CV_L$ (%) | STIME $CV_R$ (%) | $GAIT_{ASYM}$ (%) | $PHASE_{SYNC}$ (%) |
|---|---|---|---|---|---|---|---|---|---|---|---|---|---|---|---|---|---|---|---|---|---|---|---|
| PS | -15.8 | -43.4 | -17.7 | 31.3 | 27.6 | -31.3 | -30.8 | 20.4 | 20.2 | 33.2 | 34.2 | -12.7 | -7.6 | 8.1 | 4.9 | -25.8 | 41.1 | 81.6 | 59.9 | 86.8 | 54.7 | 153.7 | 67.4 |
| SS | -21.4 | -32.5 | -12.5 | 50.3 | 52.5 | -22.4 | -21.2 | 9.6 | 9.6 | 29.2 | 29.9 | -13.0 | -11.6 | 7.1 | 6.3 | -50.2 | -47.4 | 90.8 | 73.2 | 147.2 | 99.2 | 11.0 | 73.8 |
| MS | 16.0 | -20.5 | -7.2 | 42.8 | 45.5 | -14.3 | -14.1 | 7.2 | 7.2 | 26.5 | 24.3 | -5.4 | -6.2 | 3.8 | 4.4 | -63.5 | -48.2 | 78.2 | 79.7 | -46.8 | -27.8 | -13.7 | -16.9 |
| HR | -26.9 | -51.7 | -25.8 | 46.7 | 46.5 | -34.5 | -33.4 | 33.5 | 37.8 | 41.0 | 47.3 | -14.9 | -11.9 | 9.6 | 7.5 | -13.7 | -52.0 | 122.7 | 11.7 | 161.7 | 250.3 | 20.3 | 168.6 |
| EC | -11.6 | -34.8 | -14.1 | 20.4 | 22.0 | -24.0 | -24.1 | 15.4 | 14.9 | 21.4 | 21.1 | -3.8 | -10.1 | 2.3 | 6.1 | -39.1 | -27.1 | 27.4 | 43.6 | 26.5 | 15.3 | 19.4 | 45.1 |
| DTC | -31.2 | -51.4 | -23.0 | 26.9 | 26.4 | -37.1 | -36.9 | 28.1 | 28.4 | 65.5 | 64.5 | -20.5 | -11.0 | 12.9 | 6.9 | -44.4 | 4.6 | 272.7 | 279.4 | 353.9 | 231.9 | 159.3 | 324.3 |
| DTS | -11.1 | -37.9 | -14.4 | 16.2 | 17.5 | -27.4 | -26.9 | 14.0 | 13.9 | 34.2 | 34.6 | -10.6 | -9.0 | 7.0 | 5.8 | -16.7 | 184.3 | 21.3 | 23.9 | 33.2 | 7.9 | -16.8 | 11.6 |
| DTM | -3.9 | -30.0 | -12.6 | 14.2 | 16.8 | -19.7 | -19.3 | 13.3 | 13.5 | 19.4 | 19.4 | -4.9 | -6.5 | 3.1 | 4.2 | -42.6 | 7.7 | 11.4 | 6.0 | 2.2 | -10.5 | -28.9 | -13.2 |

FIG. 9

| | BLUE | PINK |
|---|---|---|
| < \| > 3 SD | | |
| < \| > 2 SD | | |
| < \| > 1 SD | | |

| 75 YEARS | PHENOTYPE: NOT SPECIFIED | DIAGNOSIS: NOT SPECIFIED

| | FAP | VELOCITY (cm/s) | CAD (STEPS/MIN) | $BoS_L$ (cm) | $BoS_R$ (cm) | $SLen_L$ (cm) | $SLen_R$ (cm) | $STIME_L$ (s) | $STIME_R$ (s) | $DSUPP_L$ (%) | $DSUPP_R$ (%) | $SWING_L$ (%) | $SWING_R$ (%) | $STANCE_L$ (%) | $STANCE_R$ (%) | BoS $CV_L$ (%) | BoS $CV_R$ (%) | SLen $CV_L$ (%) | SLen $CV_R$ (%) | STIME $CV_L$ (%) | STIME $CV_R$ (%) | $GAIT_{ASYM}$ (%) | $PHASE_{SYNC}$ (%) |
|---|---|---|---|---|---|---|---|---|---|---|---|---|---|---|---|---|---|---|---|---|---|---|---|
| PS | -1.4 | -18.0 | -3.3 | 33.4 | 29.9 | -15.4 | -15.1 | 1.5 | 2.1 | 18.8 | 18.4 | -8.1 | -3.6 | 5.2 | 2.3 | 3.3 | 14.0 | 27.3 | -8.0 | 61.8 | 39.4 | 84.6 | 20.4 |
| SS | -20.7 | -27.1 | -11.1 | 49.9 | 52.0 | -16.5 | -16.1 | 7.8 | 7.9 | 17.7 | 17.3 | -8.8 | -3.9 | 4.8 | 2.1 | -36.2 | -31.1 | -8.4 | -0.5 | 55.2 | 34.1 | 199.7 | 79.7 |
| MS | 1.9 | -7.8 | 5.8 | 29.4 | 27.6 | -12.6 | -13.2 | -6.9 | -6.3 | 16.2 | 12.4 | -3.4 | -3.6 | 2.3 | 2.4 | 16.9 | -3.8 | 47.0 | 52.3 | 0.5 | 30.7 | -61.3 | 1.6 |
| HR | -12.1 | -40.8 | -18.2 | 37.0 | 38.1 | -27.3 | -26.9 | 20.5 | 20.7 | 30.2 | 30.0 | -8.6 | -8.4 | 5.6 | 5.3 | 29.0 | -39.6 | -2.6 | -7.5 | 93.7 | 53.6 | 19.3 | 11.5 |
| EC | -11.3 | -38.3 | -20.5 | 8.2 | 9.9 | -22.7 | -22.5 | 24.2 | 24.0 | 21.4 | 22.1 | -6.9 | -9.0 | 4.2 | 5.4 | -32.0 | -38.7 | -41.4 | -30.1 | 4.2 | 7.7 | 1.7 | 9.4 |
| DTC | -6.5 | -29.8 | -8.0 | 22.7 | 28.5 | -23.6 | -22.4 | 5.9 | 7.3 | 23.8 | 21.8 | -8.3 | -6.6 | 5.2 | 4.1 | -27.7 | -24.5 | 92.2 | 69.2 | 30.1 | 16.6 | 83.7 | 53.7 |
| DTS | -12.5 | -40.0 | -15.2 | 36.7 | 38.2 | -29.0 | -28.4 | 14.2 | 15.3 | 39.6 | 38.8 | -11.0 | -10.4 | 7.3 | 6.7 | -26.8 | 223.3 | 9.7 | 6.0 | 28.1 | 27.4 | 3.4 | 49.0 |
| DTM | -8.6 | -37.9 | -16.7 | 21.0 | 24.6 | -25.6 | -25.1 | 18.4 | 18.5 | 27.3 | 27.4 | -8.8 | -8.2 | 5.6 | 5.2 | -13.8 | 14.1 | 71.7 | 48.1 | 49.0 | 37.3 | 16.2 | 50.0 |

FIG. 9 (CONT.)

THERAPEUTIC AGENTS FOR NEURODEGENERATIVE DISEASES

This application is a divisional application of U.S. application Ser. No. 16/324,353, filed Feb. 8, 2019, which is the United States national stage entry under 35 U.S.C. § 371 of International Application No. PCT/IB2017/054929, filed on Aug. 11, 2017, and published as WO 2018/029658, which claims priority to UK Patent Application No. 1613829.9, filed on Aug. 11, 2016, UK Patent Application No. 1702551.1, filed Feb. 16, 2017, UK Patent Application No. 1705766.2, filed Apr. 10, 2017, and UK Patent Application No. 1706867.7, filed Apr. 28, 2017; all of which are incorporated herein by reference in their entirety.

Neurodegenerative diseases are those that affect neurons. The degenerative process can involve the progressive loss of neuronal structure, the progressive loss of neuronal function, or progressive neuron cell death. Such progressive neurodegeneration often results in physical disability and mental deterioration. Many neurodegenerative diseases are severely progressive and unremitting, and there are few, if any, curative treatments.

Although the process of neurodegeneration is not fully understood, therapeutic agents that are shown to be broadly neuroprotective are thought to be applicable to neurodegenerative diseases generally. In addition, many neurodegenerative diseases are associated with lysosomal dysfunction. This includes both neurodegenerative lysosomal storage disorders (LSDs) and many other neurodegenerative diseases, such as Alzheimer's disease and Parkinson's disease, where links to lysosomal defects have been suggested.

The present disclosure addresses a need to develop improved and widely applicable treatments for neurodegenerative diseases. In particular, the present disclosure describes acetyl-leucine for treating a neurodegenerative disease or one or more symptoms of a neurodegenerative disease in a subject. The neurodegenerative disease may, but need not, be associated with lysosomal dysfunction.

In one embodiment, there is disclosed acetyl-leucine, or a pharmaceutically acceptable salt thereof, for use in a method of treating a neurodegenerative disease or one or more symptoms associated with a neurodegenerative disease in a subject in need thereof, wherein the neurodegenerative disease is not cerebellar ataxia or Niemann-Pick type C disease.

In one embodiment of the present disclosure, acetyl-leucine, or a pharmaceutically acceptable salt thereof, is disclosed for use in a method of treating a neurodegenerative disease in a subject in need thereof, wherein the subject is asymptomatic.

In another embodiment, there is disclosed acetyl-leucine, or a pharmaceutically acceptable salt thereof, for use in a method of delaying onset of a neurodegenerative disease or one or more symptoms of a neurodegenerative disease that would otherwise be expected to manifest according to typical disease progression.

In a further embodiment, the present disclosure includes acetyl-leucine, or a pharmaceutically acceptable salt thereof, for use in a method of treating a neurodegenerative disease or one or more symptoms associated with a neurodegenerative disease in a subject in need thereof, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In one embodiment, the present disclosure describes acetyl-leucine, or a pharmaceutically acceptable salt thereof, for use in a method of delaying progression of a neurodegenerative disease or one or more symptoms associated with a neurodegenerative disease over time as compared to typical disease progression, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In a further embodiment, acetyl-leucine, or a pharmaceutically acceptable salt thereof, is disclosed for use in a method of reversing progression of a neurodegenerative disease or one or more symptoms associated with a neurodegenerative disease over time, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In another embodiment, acetyl-leucine, or a pharmaceutically acceptable salt thereof, is disclosed for use in a method of improving in a subject in need thereof a biochemical marker of a neurodegenerative disease over time, wherein the method comprises administering a therapeutically effective amount of the acetyl-leucine to the subject in need thereof for a duration chosen from at least about 3 months, at least about 6 months, at least about 1 year, at least about 2 years, and at least about 5 years.

In another embodiment, the present disclosure includes acetyl-leucine, or a pharmaceutically acceptable salt thereof, for use in a method of reducing the severity of a neurodegenerative disease or reducing the severity of or eliminating one or more existing symptoms associated with a neurodegenerative disease in a subject in need thereof, wherein the neurodegenerative disease is not cerebellar ataxia or Niemann-Pick Type C.

In a further embodiment, the present disclosure includes acetyl-leucine, or a pharmaceutically acceptable salt thereof, for use in a method of providing neuroprotection in a subject having, suspected of having, or at risk of having a neurodegenerative disease, wherein the method comprises administering a therapeutically effective amount of the acetyl-leucine to the subject for a duration chosen from at least about 3 months, at least about 6 months, at least about 1 year, at least about 2 years, and at least about 5 years.

Additional embodiments of the present disclosure include, acetyl-leucine, or a pharmaceutically acceptable salt thereof, for use in a method of delaying progression of a neurodegenerative disease or a lysosomal storage disorder (LSD) in a subject. In another embodiment, acetyl-leucine, or a pharmaceutically acceptable salt thereof, for use in a method of providing neuroprotection in a subject having a neurodegenerative disease or a LSD. In an embodiment, the acetyl-leucine is in racemate form, in an enantiomeric excess of the L-enantiomer or in an enantiomeric excess of the D-enantiomer. In another embodiment, the methods further comprise administering the acetyl-leucine in a dose of between 1.5 g and to g per day. Further still, in an embodiment, the methods further comprise administering the acetyl-leucine for a treatment duration of two weeks or more. For example, the methods comprise administering the acetyl-leucine, or a pharmaceutically acceptable salt thereof, before the onset of a symptom of the disease or disorder to be treated. Yet in an additional embodiment, the methods further comprise administering another therapy or agent intended to prevent or treat the disease or disorder to be treated. In an embodiment of the present disclosure provides for a kit for delaying progression of a neurodegenerative disease or a LSD in a subject, the kit comprising a means for diagnosing or prognosing a neurodegenerative disease or a LSD, and acetyl-leucine or a pharmaceutically acceptable salt thereof. For example, the kit comprises a means for diagnosing or prognosing a neurodegenerative disease or a LSD, and acetyl-leucine or a pharmaceutically acceptable salt thereof. In a further embodiment of the present disclosure, it provides for use of acetyl-leucine, or a pharmaceutically acceptable salt thereof, as a neuroprotective agent in a subject having a neurodegenerative disease or a LSD. In a further embodiment of the methods, the kits, or the uses, the neurodegenerative disease is associated with defects in lysosomal storage. In an embodiment of the methods, the kits, or the uses, the neurodegenerative disease is alcoholism, Alexander's disease, Alper's disease, Alzheimer's Disease, amyotrophic lateral sclerosis (ALS), ataxia telangiectasia, neuronal ceroid lipofuscinoses, Batten disease, bovine spongiform encephalopathy (BSE), Canavan disease, cerebral palsy, Cockayne syndrome, corticobasal degeneration, Creutzfeldt-Jakob disease, frontotemporal lobar degeneration, Huntington's disease, HIV-associated dementia, Kennedy's disease, Lewy body dementia, neuroborreliosis, Machado-Joseph disease, multiple system atrophy, multiple sclerosis, multiple sulfatase deficiency, mucolipidoses, narcolepsy, Niemann Pick disease, Parkinson's Disease, Pick's disease, Pompe disease, primary lateral sclerosis, prion diseases, progressive supranuclear palsy, Refsum's disease, Schilder's disease, subacute combined degeneration of spinal cord secondary to pernicious anaemia, Spielmeyer-Vogt-Sjogren-Batten disease, spinocerebellar ataxia, spinal muscular atrophy, Steele-Richardson-Olszewski disease, or Tabes dorsalis. In a further embodiment of the methods, the kits, or the uses, the LSD is Niemann-Pick Type C (NPC1 and/or NPC2 defect), Smith-Lemli-Opitz Syndrome (SLOS), an inborn error of cholesterol synthesis, Tangier disease, Pelizaeus-Merzbacher disease, a neuronal ceroid lipofuscinosis, a primary glycosphingolipidosis, Farber disease or multiple sulphatase deficiency. For example, in the methods, the kits, or the uses, the primary glycosphingolipidosis is Gaucher disease, Fabry disease, GM1 gangliosidosis, GM2 gangliosidosis, Krabbe disease or metachromatic leukodystrophy (MLD). Further for example, in the methods, the kits, or the uses, the LSD is NPC, Tay-Sachs disease, Sandhoff disease, GM1 gangliosidosis, Fabry disease, a neurodegenerative mucopolysaccharidosis, MPS I, MPS IH, MPS IS, MPS II, MPS III, MPS IIIA, MPS IIIB, MPS IIIC, MPS HID, MPS, IV, MPS IV A, MPS IV B, MPS VI, MPS VII, MPS IX, a disease with secondary lysosomal involvement, SLOS, or Tangier disease. In an additional embodiment of the methods, the kits, or the uses, the neurodegenerative disease is cerebellar ataxia, Niemann Pick disease, parkinsonism, neuronopathic Gaucher disease, Sandhoffs disease, Louis-Barr syndrome, Alzheimer's disease, Parkinson's disease, multiple systems atrophy, frontotemporal dementia or lower body Parkinson's syndrome. In still a further embodiment of the methods, the kits or the uses, the neurodegenerative disease is Niemann Pick disease, Niemann Pick type C, Niemann Pick type A, Tay-Sachs disease, Sandhoffs disease, amyotrophic lateral sclerosis (ALS), multisystemic atrophy cerebellar type (MSA-C), fronto-temporal dementia with parkinsonism, corticobasal-degeneration-syndrome, progressive supranuclear palsy or cerebellar downbeat nystagmus. In an embodiment of the methods, the kits, or the uses, the LSD is Niemann Pick disease, Niemann Pick type C, Niemann Pick type A, Tay-Sachs disease, Sandhoffs disease or mucolipidosis type IT.

BRIEF DESCRIPTION OF THE FIGURES

FIGS. 3D and 3E show front paw (FP) data (stand mean and step cycle in panel D; duty cycle in panel E). FIGS. 3F and 3G show hind paw (HP) data (stand mean and step cycle in panel F; duty cycle in panel G).

FIG. 9 shows a gait analysis matrix for a 75 year-old male patient diagnosed with corticobasal-degeneration-syndrome before and during treatment with acetyl-leucine, wherein fewer pink areas in the matrix indicate improvement compared to before treatment.

DESCRIPTION

Figure 1A:
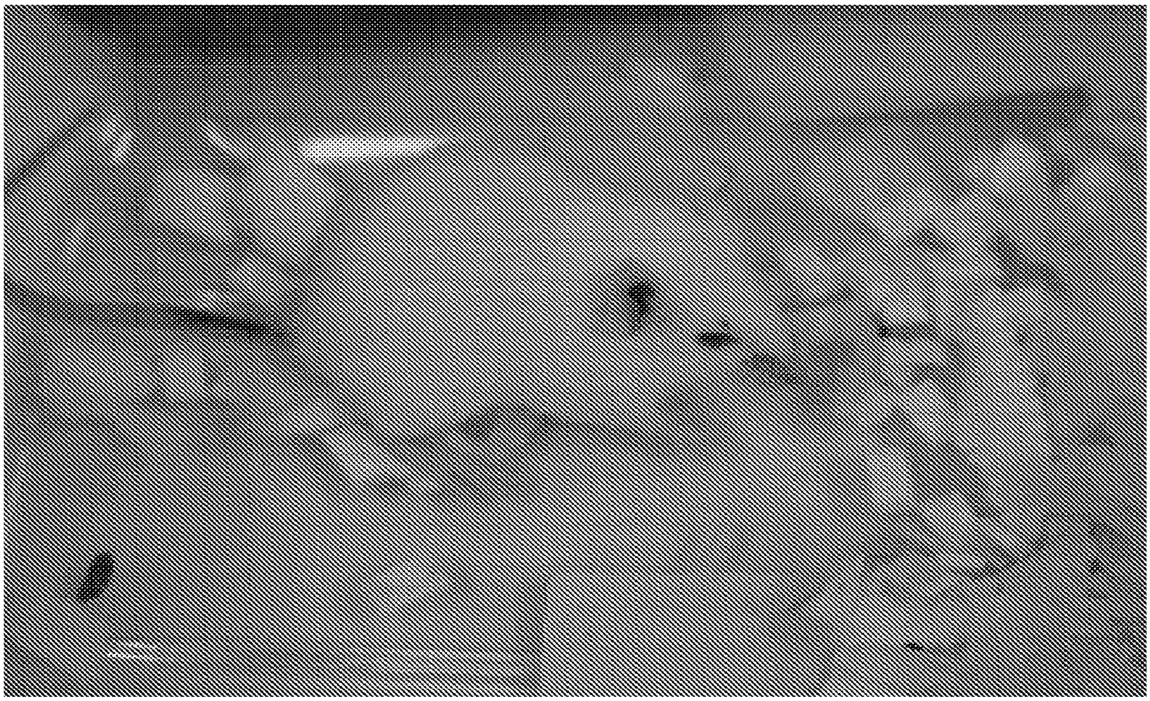
FIG. 1 shows photographs of treated (FIG. 1A) and untreated (FIG. 1B) $Npc1^{-/-}$ mice at nine weeks of age.

Acetyl-leucine in racemate form (acetyl-DL-leucine) and salts of the same are effective in the treatment of vertigo of various origins, notably Meniere's vertigo and vertigo of inflammatory (vestibular neuritis) or toxic origin. For example, acetyl-leucine is marketed by Pierre Fabre Medicament in racemate form as an anti-vertigo medicament under the name Tanganil®. Clinical results of Tanganil® reported by various authors demonstrate an improvement in vertigo symptomology in more than 95% of cases, including the disappearance of vertigo attacks.

Acetyl-DL-leucine has been used in France to treat acute vertigo since 1957 and has an excellent safety profile, but its long-term safety in chronic use has not been determined. Despite numerous hypotheses, including stabilisation of membrane potential, its pharmacological and electrophysiological modes of action remain unclear. (Vibert et al. (2001) *Eur J Neurosci;* 13(4): 735-48; Ferber-Viart et al. (2009) *Audiol Neurootol;* 14(1): 17-25). A FDG-pPET study in a rat model of an acute unilateral labyrinthectomy (Zwergal et al. (2016) *Brain Struct Funct;* 221(1): 159-70) showed a significant effect of an L-enantiomer, N-acetyl-L-leucine, on postural compensation by activation of the vestibulocerebellum and a deactivation of the posterolateral thalamus (Gunther et al. (2015) *PLoS One;* 10(3): eo120891). The symptomatic improvement of cerebellar ataxia using acetyl-DL-leucine was shown in a case series with cerebellar patients (Strupp et al. (2013) *J Neurol;* 260(10): 2556-61). Another case series did not find benefit (Pelz et al. (2015) *J Neurol;* 262(5): 1373-5). Quantitative gait analysis showed that acetyl-DL-leucine improved temporal gait variability in patients with cerebellar ataxia (Schniepp et al. (2015) *Cerebellum;* 3:8). In a one-month study involving 12 patients with Niemann-Pick Type C (NPC), symptomatic improvement of ataxia was shown (Bremova et al. (2015) *Neurology;* 85(16): 1368-75). Further, a PET study in patients with ataxia given acetyl-DL-leucine demonstrated an increased metabolism in the midbrain and lower brainstem in responders (Becker-Bense et al. (2015) Abstract EAN).

Acetyl-leucine, however, is not known to treat neurodegenerative diseases, which generally progress over the course of years to decades. The present disclosure surprisingly shows that acetyl-leucine, or a pharmaceutically acceptable salt of the same, can be used in a method of treating a neurodegenerative disease in a subject in need thereof, for example, by delaying onset of a neurodegenerative disease or one or more symptoms of a neurodegenerative disease that would otherwise be expected to manifest according to typical disease progression, and/or by delaying or reversing progression of a neurodegenerative disease or one or more symptoms of a neurodegenerative disease, such as over long durations, as compared to typical disease progression. These exemplary uses according to the present disclosure, as well as others described herein, were entirely unexpected, as such benefits had not been observed, and could not have been deduced, from the prior art teaching. As evidenced by the Examples, which demonstrate effectiveness over a wide range of neurodegenerative diseases, the inventors believe that acetyl-leucine is acting as a neuroprotective agent and so inhibiting the neurodegeneration that would otherwise be expected to manifest. In addition, many neurodegenerative diseases are associated with defects in lysosomal storage, and, lysosomal dysfunction, such as aberrantly high levels of lysosomal storage, may be a cause of neuronal dysfunction and death. As evidenced by the Examples, but without wishing to be bound by any specific theory, the present inventors discovered, inter alia, that acetyl-leucine can improve cellular dysfunction (e.g., by reducing lysosomal volumes towards control values) and provide neuroprotection.

Consequently, the present disclosure provides acetyl-leucine, or a pharmaceutically acceptable salt of the same, for use in a method of treating a neurodegenerative disease or one or more symptoms of a neurodegenerative disease in a subject in need thereof.

A "subject", as used herein, may be a vertebrate, mammal or domestic animal. Hence, compositions according to the disclosure may be used to treat any mammal, for example livestock (e.g. a horse, cow, sheep or pig), pets (e.g. a cat, dog, rabbit or guinea pig), a laboratory animal (e.g. a mouse or rat), or may be used in other veterinary applications. In one embodiment, the subject is a human being.

"Neurodegenerative disease", as used herein, refers to any disorder that affects neurons and involves the progressive loss of neuronal structure, the progressive loss of neuronal function, or progressive neuron cell death.

As used herein, the singular forms "a," "an," and "the" include plural reference. The terms "approximately" and "about" mean to be nearly the same as a referenced number or value including an acceptable degree of error for the quantity measured given the nature or precision of the measurements.

As used herein, the terms "approximately" and "about" should be generally understood to encompass ±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure.

References to "acetyl-leucine" throughout include pharmaceutically acceptable salts of the same, even if not expressly stated.

The acetyl-leucine may be in racemic form, which means that the compound comprises about equal amounts of enantiomers. Alternatively it may be present in an enantiomeric excess of either the L-enantiomer or the D-enantiomer. The acetyl-leucine may be in a single enantiomeric form of either the L-enantiomer or the D-enantiomer. In one embodiment, the single enantiomeric form is the L-enantiomer. The racemic and enantiomeric forms may be obtained in accordance with known procedures in the art.

A "pharmaceutically acceptable salt" as referred to herein, is any salt preparation that is appropriate for use in a pharmaceutical application. Pharmaceutically acceptable salts include, but are not limited to, amine salts, such as N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chloro-benzyl-2-pyrrolidin-1'-ylmethylbenzimidazole, diethylamine and other alkylamines, piperazine, tris(hydroxymethyl)aminomethane and the like; alkali metal salts, such as lithium, potassium, sodium and the like; alkali earth metal salts, such as barium, calcium, magnesium and the like; transition metal salts, such as zinc, aluminum and the like; other metal salts, such as sodium hydrogen phosphate, disodium phosphate and the like; mineral acids, such as hydrochlorides, sulfates and the like; and salts of organic acids, such as acetates, lactates, malates, tartrates, citrates, ascorbates, succinates, butyrates, valerates, fumarates and the like.

The acetyl-leucine, or a pharmaceutically acceptable salt of the same, may be formulated and administered to a subject in accordance with known teachings in the art. For example, the acetyl-leucine, or a pharmaceutically acceptable salt of the same, may be formulated as a pharmaceutical composition. The pharmaceutical composition may comprise acetyl-leucine, or a pharmaceutically acceptable salt of the same, and a pharmaceutically acceptable carrier. Reference to the pharmaceutical composition encompasses the active agent alone or in the form of a pharmaceutical composition.

The pharmaceutical composition may take any of a number of different forms depending, in particular, on the manner in which it is to be used. Thus, for example, it may be in the form of a powder, tablet, capsule, liquid, ointment, cream, gel, hydrogel, aerosol, spray, micellar solution, transdermal patch, liposome suspension or any other suitable form that may be administered to a person or animal in need of treatment.

A "pharmaceutically acceptable carrier" as referred to herein, is any known compound or combination of known compounds that are known to those skilled in the art to be useful in formulating pharmaceutical compositions. It will be appreciated that the carrier of the pharmaceutical composition should be one which is tolerated by the subject to whom it is given.

In one embodiment, the pharmaceutically acceptable carrier may be a solid, and the composition may be in the form of a powder or tablet. A solid pharmaceutically acceptable carrier may include, but is not limited to, one or more substances which may also act as flavouring agents, buffers, lubricants, stabilisers, solubilisers, suspending agents, wetting agents, emulsifiers, dyes, fillers, glidants, compression aids, inert binders, sweeteners, preservatives, dyes, coatings, or tablet-disintegrating agents. The carrier may also be an encapsulating material. In powders, the carrier may be a finely divided solid that is in admixture with the finely divided active agents according to the invention. In tablets, the active agent may be mixed with a carrier having the necessary compression properties in suitable proportions and compacted in the shape and size desired. The powders and tablets may, for example, contain up to 99% of the active agents. Suitable solid carriers include, for example, calcium phosphate, magnesium stearate, talc, sugars, lactose, dextrin, starch, gelatin, cellulose, polyvinylpyrrolidine, low melting waxes and ion exchange resins. In another embodiment, the pharmaceutically acceptable carrier may be a gel and the composition may be in the form of a cream or the like.

The carrier may include, but is not limited to, one or more excipients or diluents. Examples of such excipients are gelatin, gum arabicum, lactose, microcrystalline cellulose, starch, sodium starch glycolate, calcium hydrogen phosphate, magnesium stearate, talcum, colloidal silicon dioxide, and the like.

In another embodiment, the pharmaceutically acceptable carrier may be a liquid. In one embodiment, the pharmaceutical composition is in the form of a solution. Liquid carriers are used in preparing solutions, suspensions, emulsions, syrups, elixirs and pressurized compositions. The acetyl-leucine may be dissolved or suspended in a pharmaceutically acceptable liquid carrier such as water, an organic solvent, a mixture of both or pharmaceutically acceptable oils or fats. The liquid carrier may contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, such as sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier may also be an oily ester such as ethyl oleate and isopropyl myristate. Sterile liquid carriers are useful in sterile liquid form compositions for parenteral administration. The liquid carrier for pressurised compositions may be a halogenated hydrocarbon or other pharmaceutically acceptable propellant.

Liquid pharmaceutical compositions, which are sterile solutions or suspensions, may be utilised by, for example, intramuscular, intrathecal, epidural, intraperitoneal, intravenous and particularly subcutaneous injection. The active agent may be prepared as a sterile solid composition that may be dissolved or suspended at the time of administration using sterile water, saline, or other appropriate sterile injectable medium.

The compositions may be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The compositions may also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Acetyl-leucine and compositions comprising the same may alternatively be administered by inhalation (e.g. intranasally). Compositions may also be formulated for topical use. For instance, creams or ointments may be applied to the skin.

Acetyl-leucine may be incorporated within a slow- or delayed-release device. Such devices may, for example, be inserted on or under the skin, and the medicament may be released over weeks or even months. Such devices may be advantageous when long-term treatment with acetyl-leucine used according to the present disclosure is required and which would normally require frequent administration (e.g. at least daily administration).

In one embodiment, the pharmaceutical composition is in the form of a tablet. In tablets, the active agent may be mixed with a vehicle, such as a pharmaceutically acceptable carrier, having the necessary compression properties in suitable proportions and compacted in the shape and size desired. The tablets may contain up to 99% by weight of the active agents.

For example, the acetyl-leucine, or a pharmaceutically acceptable salt of the same, may be provided in a solid dosage form suitable for oral administration, notably in the form of a tablet.

Pharmaceutical compositions in solid oral dosage form, such as tablets, may be prepared by any method known in the art of pharmacy. Pharmaceutical compositions are usually prepared by mixing the acetyl-leucine, or a pharmaceutically acceptable salt thereof, with conventional pharmaceutically acceptable carriers.

A tablet may be formulated as is known in the art. Tanganil®, for example, includes wheat starch, pregelatinised maize (corn) starch, calcium carbonate and magnesium stearate as excipients. The same, or similar, excipients, for example, may be employed with the present disclosure.

The composition of each 700 mg Tanganil® tablet is as follows: 500 mg acetyl-DL-leucine, 88 mg wheat starch, 88 mg pregelatinised maize (corn) starch, 13 mg calcium carbonate and 11 mg magnesium stearate. The same tablets, for example, may be employed with the present disclosure.

The present disclosure describes acetyl-leucine, including compositions and methods thereof, for treating a neurodegenerative disease or one or more symptoms of a neurodegenerative disease in a subject in need thereof. The subject in need thereof may have a genetic, biochemical, or other similar identifiable marker of a neurodegenerative disease. For example, the marker of a neurodegenerative disease may be a cellular marker. The subject in need thereof may have been diagnosed as having a neurodegenerative disease. For example, the subject may have been diagnosed with a neurodegenerative disease according to a genetic, biochemical, or other similar identifiable marker. The subject in need thereof may be suspected of having or at risk of having a neurodegenerative disease. For example, the subject may have a genetic predisposition to a neurodegenerative disease (e.g., the subject may have one or more family members with a neurodegenerative disease). The subject in need thereof may be symptomatic (i.e., have one or more symptoms associated with a neurodegenerative disease). The subject in need thereof may be asymptomatic. It should be understood that the terms "symptomatic" and "asymptomatic" are used with reference to symptoms of a neurodegenerative disease. Subjects who have a genetic, biochemical, or other similar identifiable marker of a neurodegenerative disease, such as subjects who have been diagnosed with a neurodegenerative disease based on a genetic, biochemical, or other similar identifiable marker, but who have no further symptoms of the disease are included within the scope of "asymptomatic" for purposes of the present disclosure.

As used herein, "treating a neurodegenerative disease or one or more symptoms of a neurodegenerative disease" and the like refer to delaying onset of a neurodegenerative disease or one or more symptoms of a neurodegenerative disease that would otherwise be expected to manifest according to typical disease progression, reducing the severity of a neurodegenerative disease or reducing the severity of or eliminating one or more existing symptoms associated with a neurodegenerative disease, delaying progression of a neurodegenerative disease or one or more symptoms of a neurodegenerative disease over time as compared to typical disease progression, and/or reversing progression of a neurodegenerative disease or one or more symptoms of a neurodegenerative disease over time. "Treating a neurodegenerative disease or one or more symptoms of a neurodegenerative disease" may also refer to improving a biochemical marker of a neurodegenerative disease.

As used herein, "typical disease progression," "disease progression that would typically be expected" and the like refer to the typical or expected progression of a neurodegenerative disease, one or more symptoms associated with a neurodegenerative disease, or a biochemical marker of a neurodegenerative disease if the subject were untreated. Typical or expected disease progression may be based, for example, on a known scale, index, rating, or score, or other suitable test, for assessing the progression of a neurodegenerative disease, one or more symptoms of a neurodegenerative disease, or a biochemical marker of a neurodegenerative disease, such as those described as examples herein. The scale, index, rating, score, or other suitable test may correspond to the progression of the disease overall or to the progression of one or more symptoms associated with the disease. For instance, typical or expected disease progression may be based on the typical or expected onset or severity of the neurodegenerative disease or a symptom or collection of symptoms associated with the neurodegenerative disease. The typical or expected disease progression may be determined on a subject-by-subject basis or may be based on what is typically observed for or experienced by a collection of subjects afflicted with the neurodegenerative disease, such as a population or subpopulation of subjects. Subpopulations may include, for example, subpopulations of the same gender, of the same or similar age, of the same or similar timing for the onset of one or more symptoms, etc.

In one embodiment, "treating a neurodegenerative disease or one or more symptoms of a neurodegenerative disease" refers to delaying onset of a neurodegenerative disease or one or more symptoms of a neurodegenerative disease that would otherwise be expected to manifest according to typical disease progression. As used herein, "delaying onset of a neurodegenerative disease or one or more symptoms of a neurodegenerative disease" and the like refer to increasing the time to, or preventing, onset of the neurodegenerative disease or one or more symptoms of the neurodegenerative disease. For example, onset can be said to be delayed when the time to manifestation of a neurodegenerative disease or one or more symptoms of a neurodegenerative disease takes at least 5% longer than that observed according to typical disease progression. Further, for example, an increase in time of at least 10%, at least 15%, at least 20%, at least 25%, at least 30%, at least 40%, at least 50%, at least 60%, at least 70%, at least 80%, at least 90% or at least 100% is observed. In one embodiment, the subject is asymptomatic. The administration of acetyl-leucine may be initiated at the time the subject is asymptomatic to delay onset of a neurodegenerative disease or one or more symptoms of a neurodegenerative disease that would otherwise be expected to manifest according to typical disease progression. In another embodiment, the subject is symptomatic. The administration of acetyl-leucine may be initiated at the time the subject has some symptoms in order to delay onset of one or more additional symptoms of a neurodegenerative disease that would otherwise be expected to manifest according to typical disease progression. The subject in need thereof may continue to receive treatment with acetyl-leucine in accordance with the durations described herein. In one embodiment, the treatment prevents onset of one or more symptoms of the neurodegenerative disease that would otherwise be expected to manifest according to typical disease progression.

In one embodiment, "treating a neurodegenerative disease or one or more symptoms of a neurodegenerative disease" refers to reducing the severity of a neurodegenerative disease or reducing the severity of or eliminating one or more existing symptoms associated with a neurodegenerative disease. The severity of a neurodegenerative disease or of the existing symptom(s) may be assessed using a known scale, index, rating, or score, such as those described as examples herein, or another suitable test for assessing severity. For example, the scale, index, rating, score, or other suitable test may correspond to the severity of the disease overall or to the severity of one or more symptoms associated with the disease. In one embodiment, the treatment improves such an assessment from a value or degree characteristic of a symptomatic patient to a value or degree characteristic of a non-symptomatic patient.

In one embodiment, "treating a neurodegenerative disease or one or more symptoms of a neurodegenerative disease" refers to delaying progression of a neurodegenerative disease or one or more symptoms associated with a neurodegenerative disease over time as compared to typical disease progression, or reversing progression of a neurodegenerative disease or one or more symptoms associated with a neurodegenerative disease over time. The time over which the treatment delays or reverses progression may coincide with the duration of treatment as described herein. The treatment may delay or reverse progression over a duration of, for example, about seven days or more, about two weeks or more, about three weeks or more, about one month or more, about six weeks or more, about seven weeks or more or about two months or more. The treatment may delay or reverse progression over a duration of, for example, about three months or more, about four months or more, about five months or more or about six months or more. It may delay or reverse progression over a duration of, for example, about 1 year or more, about 2 years or more, about 3 years or more, about 4 years or more, about 5 years or more, or about 10 years or more. The treatment may delay or reverse progression of the neurodegenerative disease or one or more symptoms associated with the neurodegenerative disease over the lifetime of the patient.

In one embodiment, "treating a neurodegenerative disease or one or more symptoms of a neurodegenerative disease" refers to delaying progression of a neurodegenerative disease or one or more symptoms of a neurodegenerative disease over time as compared to typical disease progression. As used herein, "delaying progression of a neurodegenerative disease or one or more symptoms associated with a neurodegenerative disease over time" and the like refer to slowing and/or stopping progression of the disease or one or more symptoms of the disease (e.g., slowing and/or stopping the worsening or increasing severity of the disease or one or more symptoms of the disease) over time. Disease progression may be determined, for example, using a known scale, index, rating, or score, such as those described as examples herein, or another suitable test for assessing progression. For example, the scale, index, rating, score, or other suitable test may correspond to the progression of the disease overall or to the progression of one or more symptoms associated with the disease. In one embodiment, "delaying progression of a neurodegenerative disease or one or more symptoms associated with a neurodegenerative disease" means that a subject's disease severity value (e.g., overall severity or severity of one or more symptoms) determined by a known scale, index, rating, score, etc., or other suitable test for evaluating severity, does not meaningfully increase (e.g., at least remains substantially constant). In one embodiment, "delaying progression of a neurodegenerative disease or one or more symptoms of a neurodegenerative disease" means preventing the subject from reaching, or increasing the time taken for a subject to reach (e.g., decreasing the rate of change of increasing severity), a severity value according to a known scale, index, rating, score, etc., or other suitable test, for assessing progression compared to a value corresponding to typical disease progression. For example, progression can be said to be delayed when the time to reach a severity value takes at least 5% longer than that observed according to typical disease progression. Further for example, an increase in time of at least 10%, at least 15%, at least 20%, at least 25%, at least 30%, at least 40%, at least 50%, at least 60%, at least 70%, at least 80%, at least 90% or at least 100% is observed. The time over which the treatment delays progression of a neurodegenerative disease or one or more symptoms of a neurodegenerative disease may coincide with the duration of treatment as described herein. In one embodiment, the treatment delays progression for at least about three months, at least about four months, at least about five months, or at least about six months. The treatment may delay progression for at least about 1 year, at least about 2 years, at least about 3 years, at least about 4 years, at least about 5 years, or at least about 10 years. The treatment may delay progression over the lifetime of the patient.

In one embodiment, "treating a neurodegenerative disease or one or more symptoms of a neurodegenerative disease" refers to reversing progression of a neurodegenerative disease or one or more symptoms of a neurodegenerative disease over time. As used herein, "reversing progression of a neurodegenerative disease or one or more symptoms of a neurodegenerative disease over time" and the like refer to stopping progression and reducing the severity of the disease or one or more symptoms of the disease over time. Disease progression and severity may be determined, for example, using a known scale, index, rating, or score, such as those described as examples herein, or another suitable test for assessing progression and severity. For example, the scale, index, rating, score, or other suitable test may correspond to the progression and severity of the disease overall or to the progression and severity of one or more symptoms associated with the disease. In one embodiment, "reversing progression of a neurodegenerative disease or one or more symptoms of a neurodegenerative disease over time" means that a subject's disease severity value (e.g., overall severity or severity of one or more symptoms) determined by a known scale, index, rating, score, etc., or another suitable test, for evaluating severity, improves over time (i.e., shows a reduction in severity over time). The time over which the treatment reverses progression of a neurodegenerative disease or one or more symptoms of a neurodegenerative disease may coincide with the duration of treatment as described herein. In one embodiment, the treatment reverses progression for at least about three months, at least about four months, at least about five months, or at least about six months. In a further embodiment, the treatment reverses progression for at least about 1 year, at least about 2 years, at least about 3 years, at least about 4 years, at least about 5 years, or at least about 10 years. The treatment may reverse progression over the lifetime of the patient.

In one embodiment, "treating a neurodegenerative disease or one or more symptoms of a neurodegenerative disease" refers to improving in the subject a biochemical marker of a neurodegenerative disease (e.g., increased levels of the storage metabolite(s) or secondary biochemical changes resulting from the primary storage). A biochemical marker is a signal of disease activity and may provide ongoing indications of disease severity and progression over time. In one embodiment, the biochemical marker is improved in view of a control value. In one embodiment, the biochemical marker is chosen from increased lysosomal volume, increased glycosphingolipid (GSL) levels, increased microtubule-associated protein 1A/1B-light chain 3-phosphatidylethanolamine conjugate (LC3-JJ) levels, and increased amyloid precursor protein C-terminal fragment (APP-CTF) levels. In one embodiment, the biochemical marker is increased lysosomal volume and the treatment reduces lysosomal volume in the subject. In one embodiment, the biochemical marker is increased glycosphingolipid (GSL) levels and the treatment reduces GSL levels in the subject. In one embodiment, the biochemical marker is increased microtubule-associated protein 1A/1B-light chain 3-phosphatidylethanolamine conjugate (LC3-IJ) levels and the treatment reduces LC3-JI levels in the subject. In one embodiment, the biochemical marker is increased amyloid precursor protein C-terminal fragment (APP-CTF) levels and the treatment reduces APP-CTF levels in the subject. In one embodiment, the treatment improves a biochemical marker over time. For example, in one embodiment, improving a biochemical marker over time means that the treatment improves a biochemical marker over time toward a control value, prevents the progression of a biochemical marker over time, and/or delays the progression of the biochemical marker over time as compared to typical disease progression. The time over which the treatment improves a biochemical marker may coincide with the duration of treatment as described herein. In one embodiment, the treatment improves a biochemical marker for at least about three months, at least about four months, at least about five months, or at least about six months. The treatment may improve a biochemical marker for at least about 1 year, at least about 2 years, at least about 3 years, at least about 4 years, at least about 5 years, or at least about 10 years. The treatment may improve the biochemical marker over the lifetime of the patient.

A "symptom" of a neurodegenerative disease includes any clinical or laboratory manifestation associated with a neurodegenerative disease and is not limited to what the subject can feel or observe. Symptoms as described herein include, but are not limited to, neurological symptoms and psychiatric symptoms. Examples of neurological symptoms include ataxia, other movement disorders such as hypokinesia, rigor, tremor or dystonia, central ocular motor disorders such as vertical and horizontal supranuclear saccade/gaze palsy and neuropsychological deficits such as dementia. Examples of psychiatric symptoms include depression, behavioural disoders or psychosis. Onset of symptoms may range from birth to adulthood.

Progression of a neurodegenerative disease over time or through treatment can be monitored, for example, using one or more known tests at two or more time points and comparing the results. Disease progression and/or severity can be assessed, for example, using the Scale for the Assessment and Rating of Ataxia (SARA), Spinocerebellar Ataxia Functional Index (SCAFI), the International Cooperative Ataxia Rating Scale (ICARS), the brief ataxia rating scale (BARS), the modified Disability Rating Scale (mDRS), EuroQol 5Q-5D-5L (EQ-5D-5L), the visual analogue scale (VAS), neuropsychological tests, such as Wechsler Adult Intelligence Scale-Revised (WAIS-R), Wechsler Intelligence Scale for Children-IV (WISC-IV), Montreal Cognitive Assessment (MoCA), as well as scales used in movement disorders, such as the Unified Parkinson's Rating Scale (UPRS) or the Unified Multiple System Atrophy Rating Scale (UMSARS), or other suitable tests. For certain LSDs, such as NPC, particular scores have been developed and validated over the last decades, for instance the clinical severity score (CSS) and annual severity increment score (ASIS) (see Yanjanin et al., "Linear Clinical Progression, Independent of Age of Onset, in Niemann-Pick Disease, Type C," *Am J Med Genet Part B* 153B:132-140) and the modified 6-Domain NP-C disability Scale (mDRS score). For example, an NPC patient's severity can be quantified by assigning a CSS, which assesses various parameters of the disease (ambulation, seizures, eye movement, etc.) and gives each parameter a score out of 5. A higher score equals a greater severity. The ASIS quantifies the annual rate of change in the CSS, calculated by dividing the CSS by the patient's age. In this regard, certain scores in these tests are characteristic of symptomatic neurodegenerative disease patients and evidence disease progression and/or severity.

Thus, "treating a neurodegenerative disease or one or more symptoms of a neurodegenerative disease", for example, may be equated to achieving an improved assessment, such as those described herein, of a SARA, SCAFI, ICARS, BARS, mDRS, EQ-5D-5L, VAS, WAIS-R, WISC-IV, CSS, UPRS, UMSARS, and/or MoCA score, or result of another test suitable for characterising a neurodegenerative disease patient. For example, in one embodiment, "reducing the severity of a neurodegenerative disease or reducing the severity of or eliminating one or more existing symptoms of a neurodegenerative disease" means improving a SARA, SCAFI, ICARS, BARS, mDRS, EQ-5D-5L, VAS, WAIS-R, WISC-IV, CSS, UPRS, UMSARS, and/or MoCA score, or a result of another suitable test, for evaluating severity, such as improving the score or result from a severity value characteristic of a symptomatic subject to a value characteristic of a non-symptomatic subject. In another embodiment, "delaying progression of a neurodegenerative disease or one or more symptoms of a neurodegenerative disease" means that a subject's SARA, SCAFI, ICARS, BARS, mDRS, EQ-5D-5L, VAS, WAIS-R, WISC-IV, CSS, UPRS, UMSARS, and/or MoCA score, or a result of another suitable test for evaluating progression, does not meaningfully increase (e.g., at least remains substantially constant). In a further embodiment, "delaying progression of a neurodegenerative disease or one or more symptoms associated with a neurodegenerative disease" means preventing a subject's SARA, SCAFI, ICARS, BARS, mDRS, EQ-5D-5L, VAS, WAIS-R, WISC-IV, CSS, UPRS, UMSARS, and/or MoCA score, or a result of another suitable test for evaluating progression, from reaching, or increasing the time taken to reach, a value compared to that of typical disease progression. In another embodiment, "reversing progression of a neurodegenerative disease or one or more symptoms of a neurodegenerative disease over time" means that a subject's SARA, SCAFI, mDRS, EQ-5D-5L, VAS, WAIS-R, WISC-IV, CSS and/or MoCA score, or a result of another suitable test for evaluating progression, improves over time (i.e., shows a reduction in severity over time).

For example, to evaluate overall neurological status, mDRS, a four-domain scale (ambulation, manipulation, language and swallowing), may be applied. Cerebellar function may be evaluated using SARA, an eight-item clinical rating scale (gait, stance, sitting, speech, fine motor function and taxis; range 0-40, where 0 is the best neurological status and 40 the worst), and SCAFI, comprising the 8-m-Walking-Time (8 MW; performed by having patients walking twice as quickly as possible from one line to another excluding turning), 9-Hole-Peg-Test (9HPT) and the number of "PATA" repetitions over 10 s. Subjective impairment and quality of life may be evaluated using the EQ-5D-5L questionnaire and VAS. To assess ocular motor function, 3-dimensional videooculography (EyeSeeCam) may be used to measure the peak velocity of saccades, gain of smooth pursuit, peak slow phase velocity of gaze-evoked nystagmus (gaze-holding function), peak slow phase velocity of optokinetic nystagmus, and gain of horizontal vestibulo-ocular reflex. To evaluate the cognitive state, WAIS-R or WISC-IV, and MoCA, assessing different cognitive domains, including attention and concentration, executive functions, memory, language, visuoconstructional skills, conceptual thinking, calculations, and orientation with a maximum of 30 points and a cut-off score of 26, may be used. The skilled person will know how to perform these and other such tests.

The acetyl-leucine, or a pharmaceutically acceptable salt of the same, may be administered, for example, at a dose ranging from about 500 mg to about 15 g per day or ranging from about 500 mg to about 10 g per day, such as ranging from about 1.5 g to about 10 g per day, optionally by solid oral or liquid oral route. The acetyl-leucine, or a pharmaceutically acceptable salt of the same, may be administered, for example, in a dose according to that of Tanganil®, which is prescribed to adults in a dose of 1.5 g to 2 g per day, 3-4 tablets in two doses, morning and evening.

If one enantiomer is administered, the doses may be reduced accordingly. For instance if only acetyl-L-leucine or if only acetyl-D-leucine is administered, the dose may range from about 250 mg to about 15 g per day, range from about 250 mg to about 10 g per day, or range from about 250 mg to about 5 g per day, such as from about 0.75 g to about 5 g per day.

In one embodiment, the administered dose ranges from about 1 g to about 15 g per day, from about 1 g to about 10 g per day, or from about 1.5 g to about 7 g per day. It may be from about 2, 3, 4, 5, 6, 7, 8, 9, 10, 11, 12, 13, or 14 g to about 15 g per day. It may be from about 2, 3, 4, 5, 6, 7, 8 or 9 g to about 10 g per day. It may be more than about 1.5 g per day, but less than about 15, 14, 13, 12, 11, 10, 9, 8, 7, 6 or 5 g per day. In one embodiment, the dose ranges from about 4 g to about 6 g per day. In one embodiment, the dose ranges from about 4 g to about 5 g per day. In one embodiment, the dose is about 4.5 g per day. In one embodiment, the dose is about 5 g per day. In one embodiment, these doses are administered in a solid oral dosage form, notably tablets. In another embodiment, these doses are for acetyl-leucine when in its racemic form. Doses for acetyl-leucine when an enantiomeric excess is present may be lower than those recited here, for example, around 50% lower. The above recited dose-ranges when halved are thus also explicitly encompassed by the present disclosure.

The total daily dose may be spread across multiple administrations, i.e. administration may occur two or more times a day to achieve the total daily dose. As an example, the required number of tablets to provide the total daily dose of acetyl-leucine may be split across two administrations (for example, in the morning and evening) or three administrations (for example, in the morning, noon and evening). Each dose may be suitably administered with or without food. For example, acetyl-leucine may be dosed by about 1 or about 2 hours before meals, such as at least about 20 minutes, at least about 30 minutes, at least about 40 minutes, or at least about 1 hour before meals, or may be dosed by about 1, about 2, or about 3 hours after meals, such as waiting at least about 20 minutes, at least about 30 minutes, at least about 1 hour, at least about 1.5 hours, at least about 2 hours, or at least about 2.5 hours after meals. For example, a total daily dose of 4.5 g acetyl-DL-leucine may be administered as three Tanganil® (or equivalent) tablets before, with, or after breakfast, three further tablets before, with, or after lunch and three further tablets before, with, or after dinner.

Administration of acetyl-leucine in accordance with the present disclosure may be initiated before or after a subject is found to have a genetic, biochemical, or other similar identifiable marker of a neurodegenerative disease, such as, in the case of the former, when the subject is suspected of having or is at risk of having a neurodegenerative disease. Administration may be initiated at or around the time a subject is found to have a genetic, biochemical, or other similar identifiable marker of a neurodegenerative disease. Similarly, administration may be initiated before, at or around the time, or after a subject is diagnosed with a neurodegenerative disease, such as before, at or around the time, or after a subject is found to have a genetic, biochemical, or other similar identifiable marker of a neurodegenerative disease. Administration of acetyl-leucine may be initiated when the subject is symptomatic or asymptomatic. In particular, one of the advantages of treatment with acetyl-leucine, according to the present disclosure, is that the administration of acetyl-leucine may be initiated as early as the time after a subject is found to have a genetic and/or biochemical marker of a neurodegenerative disease but before the subject shows symptoms of the neurodegenerative disease (other than the genetic and/or biochemical marker, i.e., the subject is asymptomatic) or before the subject shows one or more symptoms considered hallmarks of the disease. The treatment may delay onset of the neurodegenerative disease or one or more symptoms associated with the neurodegenerative disease, as described herein. The treatment may also be continued for a duration as described herein.

As discussed herein, an advantage of treatment with acetyl-leucine, according to the present disclosure, is that acetyl-leucine may be administered over a long duration of time to, for example, delay or even reverse progression of a neurodegenerative disease or one or more symptoms of a neurodegenerative disease in a subject as compared to typical disease progression. Treatment duration may be, for example, about seven days or more, about two weeks or more, about three weeks or more, about one month or more, about six weeks or more, about seven weeks or more, or about two months or more. In one embodiment, it is about three months or more, about four months or more, about five months or more or about six months or more. The treatment duration may be about 1 year or more, about 2 years or more, about 4 years or more, about 5 years or more, or about 10 years or more. The treatment duration may be the life-time of the patient.

Any and all combinations of dosage form, dose amount, dosing schedule and treatment duration are envisaged and encompassed by the invention. In one embodiment, the dose is from about 4 g to about 10 g per day, taken across one, two, or three administrations per day, for a treatment duration of about two months or more. In another embodiment, the dose is more than 4 g but no more than 5 g per day, taken across one, two, or three administrations per day, for a treatment duration of about six months or more. The dosage form may be a solid oral dosage form, notably tablets.

The pharmaceutical composition may be used as a monotherapy (e.g., use of the active agent alone) for treating a neurodegenerative disease in a subject. Alternatively, the pharmaceutical composition may be used as an adjunct to, or in combination with, other known therapies, e.g., for treating a neurodegenerative disease in a subject.

The neurodegenerative disease may, but need not, be associated with lysosomal dysfunction (e.g., lysosomal storage defect). Neurodegenerative diseases, according to the present disclosure, not associated with lysosomal dysfunction include, but are not limited to, Alexander's disease, Alper's disease, cerebral palsy, Cockayne syndrome, corticobasal degeneration, HIV-associated dementia, Kennedy's disease, neuroborreliosis, primary lateral sclerosis, Refsum's disease, Schilder's disease, subacute combined degeneration of spinal cord secondary to pernicious anaemia, hereditary motor and sensory neuropathy with proximal dominance, Wobbly Hedgehog Syndrome (WHS), progressive muscular atrophy (Duchenne-Aran muscular atrophy), progressive bulbar palsy, pseudobulbar palsy, HIV-associated neurocognitive disorders (HAND), Vascular Parkinsonism, lower body Parkinson's syndrome, cerebellar downbeat nystagmus, and cerebellar ataxia, which includes Spinocerebellar ataxia (SCA) 4, Spinocerebellar ataxia (SCA) 5 (Lincoln's Ataxia), Spinocerebellar ataxia (SCA) 8, Spinocerebellar Ataxia (SCA) 10, Spinocerebellar Ataxia (SCA) 11, Spinocerebellar Ataxia (SCA) 12, Spinocerebellar Ataxia (SCA) 13, Spinocerebellar Ataxia (SCA) 14, Spinocerebellar Ataxia (SCA) 15/16, Spinocerebellar Ataxia (SCA) 18 (sensory/motor neuropathy with ataxia), Spinocerebellar Ataxia (SCA) 19/22, Spinocerebellar Ataxia (SCA) 20, Spinocerebellar Ataxia (SCA) 21, Spinocerebellar Ataxia (SCA) 23, Spinocerebellar Ataxia (SCA) 25, Spinocerebellar Ataxia (SCA) 26, Spinocerebellar Ataxia (SCA) 27, Spinocerebellar Ataxia (SCA) 29, Spinocerebellar Ataxia (SCA) 30, Spinocerebellar Ataxia (SCA) 31, Spinocerebellar Ataxia (SCA) 32, Spinocerebellar Ataxia (SCA) 35, Spinocerebellar Ataxia (SCA) 36, Episodic Ataxia (EA) 1, Episodic Ataxia (EA) 2, Episodic Ataxia (EA) 3, Episodic Ataxia (EA) 4, Episodic Ataxia (EA) 5, Episodic Ataxia (EA) 6, Episodic Ataxia (EA) 7, Spinocerebellar Ataxia (SCA) 28, Spinocerebellar Ataxia (SCA) 24 (spinocerebellar ataxia autosomal recessive type 4 (SCAR4); Spinocerebellar ataxia with saccadic intrusions), Tabes *dorsalis*, Ataxia with Oculomotor Apraxia Type 1 (AOA1), Ataxia with Oculomotor Apraxia Type 2 (AOA2), Ataxia with Oculomotor Apraxia Type 4 (AOA4), spinocerebellar ataxia autosomal recessive type 10 (SCAR 10), mitochondrial recessive ataxia syndrome (MIRAS), Myclonic Epilepsy Myopathy Sensory Ataxia (MEMSA), Sensory Ataxic Neuropathy Dysarthria Opthalmoparesis (SANDO), infantile-onset spinocerebellar ataxia, Hereditary Spastic Paraplegia 7 (HSP SPG7 gene), mitochondrial myopathy, encephalopathy, lactacidosis, stroke syndrome (MELAS), myoclonic epilepsy with ragged red fibers (MERRF), neurogenic muscle weakness, ataxia, and retinitis pigmentosa (NARP), Kearns-Sayre (KSS), Fragile X tremor/ataxia syndrome (FXTAS), Arts Syndrome, X-linked Spinocerebellar Ataxia 1, X-linked Spinocerebellar Ataxia 2, X-linked Spinocerebellar Ataxia 3, X-linked Spinocerebellar Ataxia 4 or X-linked Spinocerebellar Ataxia 5, Christianson type X-linked syndromic mental retardation, X-linked sideroblastic anemia, Idiopathic Late-Onset Cerebellar Ataxia, Sporadic Adult-Onset Ataxia of Unknown Etiology (SAOA), and cerebellar ataxia, neuropathy, vestibular areflexia syndrome (CANVAS). In one embodiment, the neurodegenerative disease not associated with lysosomal dysfunction is corticobasal degeneration, SCA 28, and AOA4.

As mentioned above, many neurodegenerative diseases are associated with lysosomal dysfunction, which includes both neurodegenerative lysosomal storage disorders (LSDs) and many other neurodegenerative diseases where links to lysosomal defects have been suggested. See, e.g., Boman et al., *Journal of Parkinson's Disease*, vol. 6, no. 2, pp. 307-315 (May 2016); Makioka et al., *Neuroreport,* 23(5): 270-276 (March 2012); Orr et al., *Alzheimer's Research & Therapy,* 5:53 (October 2013); Barlow et al., *Proc. Nat'l. Acad. Sci. USA,* 18; 97(2):871-6 (2000).

In one embodiment, the neurodegenerative disease is associated with lysosomal dysfunction (e.g., lysosomal storage defect). Neurodegenerative diseases, according to the present disclosure, associated with lysosomal dysfunction include, but are not limited to, alcoholism, Alzheimer's disease, amyotrophic lateral sclerosis (ALS), Canavan disease, frontotemporal lobar degeneration, Huntington's disease, Lewy body dementia, multiple system atrophy (MSA-P/MSA-C), multiple sclerosis, narcolepsy, Parkinson's Disease, Smith Lemli Opitz Syndrome (SLOS) (an inborn error of cholesterol synthesis), Tangier disease, Pelizaeus-Merzbacher Disease, Pick's disease, frontotemporal dementia and parkinsonism linked to chromosome 17, prion diseases, including scrapie, transmissible mink encephalopathy, chronic wasting disease, bovine spongiform encephalopathy (BSE), feline spongiform encephalopathy, exotic ungulate encephalopathy, kuru, Creutzfeldt-Jakob disease, Gerstmann-Sträussler-Scheinker syndrome, and fatal familial insomnia, progressive supranuclear palsy, spinal muscular atrophy, neurodegenerative LSDs, and cerebellar ataxia, which includes Spinocerebellar Ataxia (SCA) 1, Spinocerebellar Ataxia (SCA) 2, Spinocerebellar Ataxia (SCA) 3 (Machado-Joseph disease), Spinocerebellar Ataxia (SCA) 6, Spinocerebellar Ataxia (SCA) 7, Spinocerebellar Ataxia (SCA) 17, dentatorubral-pallidoluysian atrophy, Autosomal Recessive Spastic Ataxia of Charlevoix-Saguenay (ARSACS), autosomal recessive cerebellar ataxia type 1 (Recessive Ataxia of Beauce (RAB), SYNE-1 mutation), autosomal recessive cerebellar ataxia type 2 (spinocerebellar ataxia autosomal recessive 9, SCAR9), ataxia with vitamin E deficiency (AVED), ataxia telangiectasia (Louis Barr disease), Freidreich's ataxia (FRDA), and ataxia with coenzyme Q10 deficiency. In one embodiment, the neurodegenerative disease associated with lysosomal dysfunction is chosen from alcoholism, Alzheimer's disease, amyotrophic lateral sclerosis (ALS), Canavan disease, frontotemporal lobar degeneration, Huntington's disease, multiple system atrophy (MSA-P/MSA-C), multiple sclerosis, narcolepsy, Parkinson's Disease, Smith Lemli Opitz Syndrome (SLOS) (an inborn error of cholesterol synthesis), Tangier disease, Pelizaeus-Merzbacher Disease, Pick's disease, frontotemporal dementia, frontotemporal dementia with parkinsonism, prion diseases, progressive supranuclear palsy, and spinal muscular atrophy. In one embodiment, the neurodegenerative disease associated with lysosomal dysfunction is chosen from ALS, MSA-P, MSA-C, frontotemporal dementia with parkinsonism, progressive supranuclear palsy, SCA 28, SCA 1, and Alzheimer's disease.

Neurodegenerative LSDs are characterized by the accumulation of undigested or partially digested macromolecules resulting in cellular dysfunction and neurodegeneration, which is often progressive leading to physical disability and/or mental deterioration. They tend to present in the first few years of life and the severe progression results in frequent hospitalization. If left untreated, patients often die in their mid-teens. Adult-onset patients have also been described. Neurodegenerative LSDs, according to the present disclosure, include, but are not limited to, neuronal ceroid lipofuscinoses (Types 1-10), Gaucher disease Type 2/3 (neuronopathic), Krabbe disease, multiple sulfatase deficiency, mucolipidoses, including mucolipidosis I, mucolipidosis II, and mucolipidosis IV, Niemann-Pick Disease Type A, Niemann-Pick Disease Type B, Niemann-Pick Disease Type C, Infantile-Onset Pompe Disease, Late-Onset Pompe Disease, Tay-Sachs disease, Sandhoff disease, Farber disease, galactosialidosis, Fabry disease, Schindler disease, GM1 gangliosidosis, AB variant GM2 gangliosidosis, metachromatic leukodystrophy (MLD), mucopolysaccharidoses, including MPS IH, MPS IS, MPS IH-S, MPS II, MPS IIIA, MPS IIIB, MPS IIIC, MPS IIID, and MPS VII, beta-mannosidosis, aspartylglucosaminuria, fucosidosis, Salla disease, infantile free sialic acid storage disease (ISSD), and Danon disease. In one embodiment, the neurodegenerative LSD is chosen from NPC, NPA, mucolipidosis II, MPS IIIB, aspartylglucosaminuria, mucolipidosis IIIA, MPS VII, Sandhoff disease, Tay-Sachs disease, the AB variant of Tay-Sachs disease, and GM1 gangliosidosis. In one embodiment, the neurodegenerative disease is not chosen from a neurodegenerative LSD.

In one embodiment, the neurodegenerative disease is a Motor Neuron Disease. In one embodiment, the Motor Neuron Disease is chosen from primary lateral sclerosis, progressive muscular atrophy, progressive bulbar palsy, pseudobulbar palsy, ALS, Alzheimer's disease, Canavan disease, frontotemporal lobar degeneration, Huntington's disease, multiple sclerosis, narcolepsy, Parkinson's Disease, Pelizaeus-Merzbacher disease, and spinal muscular atrophy.

In one embodiment, the neurodegenerative disease is cerebellar ataxia. In one embodiment, the neurodegenerative disease is Niemann-Pick disease. In one embodiment, the neurodegenerative disease is Niemann-Pick type C. In one embodiment, the neurodegenerative disease is Niemann-Pick type A. In one embodiment, the neurodegenerative disease is parkinsonism. In one embodiment, the neurodegenerative disease is neuronopathic Gaucher disease. In one embodiment, the neurodegenerative disease is Tay-Sachs disease. In one embodiment, the neurodegenerative disease is Sandhoff's disease. In one embodiment, the neurodegenerative disease is Fabry disease. In one embodiment, the neurodegenerative disease is GM1 gangliosidosis. In one embodiment, the neurodegenerative disease is Louis-Barr syndrome. In one embodiment, the neurodegenerative disease is Alzheimer's disease. In one embodiment, the neurodegenerative disease is Parkinson's disease. In one embodiment, the neurodegenerative disease is multiple system atrophy. In one embodiment, the neurodegenerative disease is multiple system atrophy type C (MSA-C). In one embodiment, the neurodegenerative disease is multiple system atrophy type P (MSA-P). In one embodiment, the neurodegenerative disease is fronto-temporal dementia. In one embodiment, the neurodegenerative disease is fronto-temporal dementia with parkinsonism. In one embodiment, the neurodegenerative disease is lower body Parkinson's syndrome. In one embodiment, the neurodegenerative disease is amyotrophic lateral sclerosis (ALS). In one embodiment, the neurodegenerative disease is corticobasal-degeneration-syndrome. In one embodiment, the neurodegenerative disease is progressive supranuclear palsy. In one embodiment, the neurodegenerative disease is cerebellar downbeat nystagmus. In one embodiment, the neurodegenerative disease is SCA 28. In one embodiment, the neurodegenerative disease is ataxia telangiectasia. In one embodiment, the neurodegenerative disease is SCA 1. In one embodiment, the neurodegenerative disease is AOA4.

Major symptoms of Parkinson's Disease (PD) include rigidity, tremor, and slow movement. There are other diseases in which these symptoms are prevalent. These diseases, and PD itself, fall under the umbrella term Parkinsonism. PD can be referred to as Primary Parkinsonism. Other examples of Parkinsonisms include: Multiple System Atrophy; Progressive Supranuclear Palsy; Normal pressure hydrocephalus; and Vascular or arteriosclerotic parkinsonism. Those diseases that can be classed as Parkinsonisms, but are not PD, can also be referred to as "Parkinson-Plus Syndromes". Unlike PD patients, individuals with Parkinson-Plus Syndromes do not respond to L-Dopa. The term "parkinsonism" as used herein may refer to a motor syndrome whose main symptoms are tremor at rest, stiffness, slowing of movement and postural instability. Parkinsonian syndromes can be divided into four subtypes, according to their origin: primary or idiopathic; secondary or acquired; hereditary parkinsonism; and Parkinson plus syndromes or multiple system degeneration.

In one embodiment, the parkinsonism is a Parkinson plus syndrome or multiple system degeneration.

In one embodiment, the parkinsonism is vascular (arteriosclerotic) Parkinsonism, lower-body Parkinsonism, Multiple System Atrophy with predominant parkinsonism (MSA-P), Multiple System Atrophy with cerebellar features (MSA-C; Sporadic olivopontocerebellar atrophy (OPCA)), Shy-Drager syndrome, Progressive Supranuclear Palsy (Steele-Richardson-Olszewski syndrome), Lewy body dementia, Pick's disease, or frontotemporal dementia and parkinsonism linked to chromosome 17.

Niemann-Pick diseases are a heterogeneous group of autosomal recessive LSDs. Common cellular features include abnormal sphingomyelin (SM) storage in mononuclear phagocytic cells and parenchymal tissues, as well as (hepato)splenomegaly. Among the three main subgroups of Niemann-Pick disease (A-C), NPC (previously classified as NPC and NPD and now appreciated to be a single disease) is classified as a fatal neurovisceral LSD caused by abnormal intracellular cholesterol transport-induced accumulation of unesterified cholesterol in late endosome/lysosomal compartments. Outside the CNS, the cellular characteristics of NPC include abnormal accumulation of unesterified cholesterol and other lipids (e.g. GSLs) within late endosome/lysosomal compartments. Conversely, there is no net elevation in cholesterol in the CNS (although it does have an altered distribution) but there are highly elevated levels of GSLs. Progressive neurodegeneration is particularly characterised by sequential degeneration of GABAergic Purkinje neurons in the cerebellum, which parallels the onset and progression of cerebellar ataxia and other aspects of neurological dysfunctions seen during the course of NPC. Genetic studies have shown that NPC disease is caused by mutations in either the Npc1 or Npc2 genes. The precise mechanistic link between these two genes remains unknown and the functional roles of these proteins remains enigmatic. NPC1 encodes a multimembrane spanning protein of the limiting membrane of the late endosome/lysosome, whereas NPC2 is a soluble cholesterol binding protein of the lysosome. When NPC1 is inactivated, sphingosine is the first lipid to be stored, suggesting that NPC1 plays a role in the transport of sphingosine from the lysosome, where it is normally generated as part of sphingolipid catabolism. Elevated sphingosine in turn causes a defect in calcium entry into acidic stores resulting in greatly reduced calcium release from this compartment. This then prevents late endosome-lysosome fusion, which is a calcium dependent process, and causes the secondary accumulation of lipids (cholesterol, sphingomyelin and glycosphingolipids) that are cargos in transit through the late endocytic pathway. Other secondary consequences of inhibiting NPC1 function include defective endocytosis and failure to clear autophagic vacuoles. It has been shown that the NPC1/NPC2 cellular pathway is targeted by pathogenic mycobacteria to promote their survival in late endosomes.

The NPC mouse model shares a number of pathological features with, e.g., Alzheimer's disease (AD). Microtubule-associated protein 1A/1B-light chain 3-phosphatidylethanolamine conjugate (LC3-II) levels have previously been reported to be elevated in the NPC mouse. LC3-II is a marker of autophagosome formation, and increased levels of LC3-II can reflect impaired clearance of autophagic vacuoles. Autophagosomes are formed, but are not cleared. Autophagy is impaired in AD, and AD brains exhibit increased levels of LC3-II. In addition, amyloid precursor protein (APP) is the precursor molecule whose proteolysis generates beta amyloid (Aβ). Aβ plaques are a hallmark of the AD brain and have been proposed to be a causative factor in disease pathology. Amyloid precursor protein C-terminal fragments (APP-CTFs), which are an intermediate in the proteolysis of APP to Aβ, accumulate in the AD brain and also progressively accumulate in the brains of NPC1 mice.

Tay-Sachs disease is a fatal hereditary disorder of lipid metabolism characterised especially in CNS tissue due to deficiency of the A isozyme of β-hexosaminidase. Mutations in the HEXA gene, which encodes the a subunit of β-hexosaminidase, cause the A isozyme deficiency. Tay-Sachs is a prototype of a group of disorders, the GM2 gangliosidoses, characterized by defective GM2 ganglioside degradation. The GM2 ganglioside (monosialylated ganglioside 2) accumulates in the neurons beginning already in fetal life.

Sandhoff disease results from a deficiency of both the A and B (basic) isozymes of β-hexosaminidase. Mutations in the HEXB gene, which encodes the P subunit of β-hexosaminidase, cause the B isozyme deficiency.

GM1 gangliosidosis is caused by a deficiency of β-galactosidase, which results in lysosomal storage of GM1 ganglioside (monosialylated ganglioside 1).

Fabry disease is caused by a deficiency of α-galactosidase, which results in lysosomal storage of a ceramide trihexoside.

In one embodiment, the neurodegenerative disease is not cerebellar ataxia. In one embodiment, the neurodegenerative disease is not Niemann Pick disease. In one embodiment, the neurodegenerative disease is not Niemann Pick type C disease. In one embodiment, the neurodegenerative disease is not cerebellar ataxia or Niemann Pick disease (e.g., Niemann Pick type C disease).

In one embodiment, the acetyl-leucine, or a pharmaceutically acceptable salt thereof, treats weight loss, gait deterioration, and/or motor function deterioration associated with Niemann-Pick disease (e.g., Niemann-Pick type C or A) or mucolipidosis type II. For example, the acetyl-leucine, or a pharmaceutically acceptable salt thereof, may delay onset of, reduce the severity of or eliminate, or delay or reverse the progression of weight loss, gait deterioration, and/or motor function deterioration associated with Niemann-Pick disease (e.g. Niemann-Pick type C or A) or mucolipidosis type II. In one embodiment, the weight loss, gait deterioration, and/or motor function deterioration is associated with Niemann-Pick type A or mucolipidosis type II.

In one embodiment, the acetyl-leucine, or a pharmaceutically acceptable salt thereof, treats gait deterioration, motor function deterioration and/or reduced mobility associated with Sandhoff's disease. For example, the acetyl-leucine, or a pharmaceutically acceptable salt thereof, may delay onset of, reduce the severity of or eliminate, or delay or reverse the progression of gait deterioration, motor function deterioration, and/or reduced mobility associated with Sandhoffs disease.

In one embodiment, the acetyl-leucine, or a pharmaceutically acceptable salt thereof, treats reduced co-ordination, tremors, reduced mobility, cognitive impairment, and/or gait deterioration associated with Tay-Sachs disease. For example, the acetyl-leucine, or a pharmaceutically acceptable salt thereof, may delay onset of, reduce the severity of or eliminate, or delay or reverse the progression of reduced co-ordination, tremors, reduced mobility, cognitive impairment, and/or gait deterioration associated with Tay-Sachs disease.

In one embodiment, the acetyl-leucine, or a pharmaceutically acceptable salt thereof, treats speech deterioration (e.g., fluency of speech and/or modulation of voice), gait deterioration, reduced mobility, reduced swallowing functions, and/or paresis associated with amyotrophic lateral sclerosis (ALS). For example, the acetyl-leucine, or a pharmaceutically acceptable salt thereof, may delay onset of, reduce the severity of or eliminate, or delay or reverse the progression of speech deterioration (e.g., fluency of speech and/or modulation of voice), gait deterioration, reduced mobility, reduced swallowing functions, and/or paresis associated with ALS. In another embodiment, the acetyl-leucine, or a pharmaceutically acceptable salt thereof treats reduced sleep quality associated with ALS. For example, the acetyl-leucine, or a pharmaceutically acceptable salt thereof, may delay onset of, reduce the severity of or eliminate, or delay or reverse the progression of reduced sleep quality associated with ALS.

In one embodiment, the acetyl-leucine, or a pharmaceutically acceptable salt thereof, treats speech deterioration, gait deterioration, and/or increased propensity to falls associated with multisystemic atrophy cerebellar type (MSA-C). For example, the acetyl-leucine, or a pharmaceutically acceptable salt thereof, may delay onset of, reduce the severity of or eliminate, or delay or reverse the progression of speech deterioration, gait deterioration, and/or increased propensity to falls associated with MSA-C.

In one embodiment, the acetyl-leucine, or a pharmaceutically acceptable salt thereof, treats gait deterioration, increased propensity to falls, and/or speech deterioration associated with fronto-temporal dementia with parkinsonism. For example, the acetyl-leucine, or a pharmaceutically acceptable salt thereof, may delay onset of, reduce the severity of or eliminate, or delay or reverse the progression of gait deterioration, increased propensity to falls, and/or speech deterioration associated with fronto-temporal dementia with parkinsonism.

In one embodiment, the acetyl-leucine, or a pharmaceutically acceptable salt thereof, treats increased propensity to falls and/or gait deterioration associated with corticobasal-degeneration-syndrome. For example, the acetyl-leucine, or a pharmaceutically acceptable salt thereof, may delay onset of, reduce the severity of or eliminate, or delay or reverse the progression of increased propensity to falls and/or gait deterioration associated with corticobasal-degeneration-syndrome.

In one embodiment, the acetyl-leucine, or a pharmaceutically acceptable salt thereof, treats gait deterioration associated with progressive supranuclear palsy. For example, the acetyl-leucine, or a pharmaceutically acceptable salt thereof, may delay onset of, reduce the severity of or eliminate, or delay or reverse the progression of gait deterioration associated with progressive supranuclear palsy.

In one embodiment, the acetyl-leucine, or a pharmaceutically acceptable salt thereof, treats oscillopsia, deterioration of spatial orientation, deterioration of visual acuity, and/or increase in postural sway associated with cerebellar downbeat nystagmus. For example, the acetyl-leucine, or a pharmaceutically acceptable salt thereof, may delay onset of, reduce the severity of or eliminate, or delay or reverse the progression of oscillopsia, deterioration of spatial orientation, deterioration of visual acuity, and/or increase in postural sway associated with cerebellar downbeat nystagmus.

There is also provided a method of treating a neurodegenerative disease or one or more symptoms of a neurodegenerative disease in a subject in need thereof, the method comprising administering a therapeutically effective amount of acetyl-leucine, or a pharmaceutically acceptable salt thereof, to the subject.

A "therapeutically effective amount" of an agent is any amount which, when administered to a subject, is the amount of agent that is needed to produce the desired effect, which, for the present disclosure, can be therapeutic and/or prophylatic. The dose may be determined according to various parameters, such as the specific form of acetyl-leucine used; the age, weight and condition of the patient to be treated; the type of the disease; the route of administration; and the required regimen. A physician will be able to determine the required route of administration and dosage for any particular patient. For example, a daily dose may be from about 10 to about 225 mg per kg, from about 10 to about 150 mg per kg, or from about 10 to about 100 mg per kg of body weight.

Also disclosed is a kit for treating a neurodegenerative disease in a subject, comprising a means for diagnosing or prognosing the disease/disorder, and acetyl-leucine or a pharmaceutically acceptable salt thereof.

The means for diagnosing or prognosing a neurodegenerative disease may include a specific binding agent, probe, primer, pair or combination of primers, an enzyme or antibody, including an antibody fragment, which is capable of detecting or aiding in the detection of a neurodegenerative disease, as defined herein. The kit may comprise LysoTracker®, which is a fluorescent marker and is commercially-available from both Invitrogen and also Lonza. The LysoTracker® may be blue, blue-white, yellow, green or red.

The kit also comprises acetyl-leucine or a pharmaceutically acceptable salt thereof, as defined herein. The kit may further comprise buffers or aqueous solutions. The kit may further comprise instructions for using the acetyl-leucine or a pharmaceutically acceptable salt thereof in a method of the invention.

In a further embodiment, there is disclosed acetyl-leucine, or a pharmaceutically acceptable salt thereof, for use in a method of providing neuroprotection in a subject in need thereof (e.g., a subject having, suspected of having, or at risk of having a neurodegenerative disease).

"Neuroprotection" and its cognates, as used herein, refer to prevention, a slowing in, and/or a reversed progression of neurodegeneration, including, but not limited to, progressive loss of neuronal structure, progressive loss of neuronal function, and/or progressive neuronal death. Providing neuroprotection may result in delaying onset of a neurodegenerative disease or one or more symptoms of a neurodegenerative disease that would otherwise be expected to manifest according to typical disease progression, reducing the severity of a neurodegenerative disease or reducing the severity of or eliminating one or more existing symptoms associated with a neurodegenerative disease, delaying progression of a neurodegenerative disease or one or more symptoms of a neurodegenerative disease over time as compared to typical disease progression, and/or reversing progression of a neurodegenerative disease or one or more symptoms of a neurodegenerative disease over time. The time over which neuroprotection is provided may coincide with the duration of treatment as described herein. The treatment may provide neuroprotection over a duration of, for example, about seven days or more, about two weeks or more, about three weeks or more, about one month or more, about six weeks or more, about seven weeks or more or about two months or more. The treatment may provide neuroprotection over a duration of, for example, about three months or more, about four months or more, about five months or more or about six months or more. It may provide neuroprotection over a duration of, for example, about 1 year or more, about 2 years or more, about 3 years or more, about 4 years or more, about 5 years or more, or about 10 years or more. The treatment may provide neuroprotection over the lifetime of the patient.

In another embodiment, a method of providing neuroprotection in a subject in need thereof (e.g., a subject having, suspected of having, or at risk of having a neurodegenerative disease) comprises administering a therapeutically effective amount of acetyl-leucine, or a pharmaceutically acceptable salt thereof, to the subject.

Also disclosed is a kit for providing neuroprotection in a subject in need thereof (e.g., a subject having, suspected of having, or at risk of having a neurodegenerative disease), the kit comprising a means for diagnosing or prognosing the disease/disorder, and acetyl-leucine or a pharmaceutically acceptable salt thereof.

The present disclosure further includes the use of acetyl-leucine, or a pharmaceutically acceptable salt thereof, as a neuroprotective agent in a subject in need thereof (e.g., a subject having, suspected of having, or at risk of having a neurodegenerative disease).

All of the features described herein (including any accompanying claims, abstract and drawings), and/or all of the steps of any method so disclosed, may be combined with any of the above aspects in any combination, except combinations where at least some of such features and/or steps are mutually exclusive.

EXAMPLES

The invention will now be explained in further detail in the following Examples, which demonstrate the utility of acetyl-leucine in treating a neurodegenerative disease in a subject and providing neuroprotection in said subject.

Example 1

In Vivo Mouse Study—Methods

Mouse Model

This study made use of an authentic mouse model of NPC, the $Npc^{-/-}$ (BALB/cNctr-$Npc1^{m1N}$/J) mouse, which is null for the NPC1 protein and displays all the hallmarks of the clinical disease (Loftus, 1997).

This mutant strain arose spontaneously and has a lifespan in the range of 10-14 weeks and therefore has a course of disease more acute that the vast majority of patients. The mutant mouse has been exploited successfully, not only for determining the ontogeny of disease and underlying pathogenic mechanisms, but also for the evaluation of experimental therapies. Analyses using these mice have been undertaken at the whole animal, cellular, and molecular levels (Baudry, 2003; Smith, 2009; Cologna, 2014; Cologna, 2012). It is the most intensively studied animal model of NPC.

Prior to about 4-5 weeks of age $Npc1^{-/-}$ mice have no discernible behavioural indication of disease that distinguishes them from wild-type littermates. First indications of behavioural deficits, such as tremor and ataxic gait, appear by weeks 5-6; by weeks 7-8 defects in motor coordination become more apparent, and by 9-10 weeks ataxia is advanced and accompanied by increased loss in weight and poor coat condition as feeding and drinking becomes difficult (humane end point applied) (Smith, 2009).

Wild-type ($Npc1^{+/+}$) littermates were used as a control.

Treatment Protocol

A group of $Npc1^{-/-}$ mice and a group of $Npc1^{+/+}$ mice were treated with 0.1 g/kg acetyl-DL-leucine, provided mixed in the mouse chow, from weaning (three weeks of age). Separate groups of $Npc1^{-/-}$ and $Npc1^{+/+}$ mice were left untreated, as controls.

Coat Condition

The coat condition of $Npc1^{-/-}$ mice, with and without acetyl-DL-leucine treatment, was compared by simple observation of the mice at nine weeks of age.

Weight Data

Animals were weighed twice a week. Weights were averaged (mean) across all mice in each group and compared.

Gait Analysis

Gait analysis was performed on mice at eight weeks of age using a CatWalk® 15.0 system according to manufacturer's instructions (Noldus, Nottingham, UK). Five runs were recorded per animal.

CatWalk® parameters measured were:

1. Stand Mean: average duration (s) of paws in contact with glass plate;
2. Step Cycle: duration (s) between two consecutive contacts of the same paw;
3. Duty Cycle: percentage of time paws in contact with plate compared with time to complete a step cycle;
4. Step Sequence (AB): percentage of time spent walking in LF-RH-RF-LH alternating pattern (LF: left front; RH: right hind; RF: right front; LH left hind);
5. Cadence: step per seconds in a trial;
6. Diagonal Support: percentage of time with simultaneous contact of diagonal paws with the glass plate (RF&LH or RH&LF).

Motor Function Analysis

Motor function analysis was performed on mice at eight and nine weeks of age using an Open Field Activity Monitor according to manufacturer's instructions (Linton Instruments, Amlogger Software). Each mouse was placed in a plastic cage with bedding and analysed for five minutes. Rears were counted manually.

Motor function parameters measured were:

1. Centre Rearing: mice rearing on hind legs unsupported;
2. Rearing: mice rearing on hind legs with and without the support of cage walls;
3. Activity: regular movement of the animal including walks;
4. Front to Back (FR) count: movement of the animal from front to back of the cage;
5. Active Time: duration (s/min) of activeness regardless of movement;
6. Mobile Time: duration (s/min) of mobility;
7. Rearing Time: duration of any rearing.

Results

Coat Condition

Figure 1B:
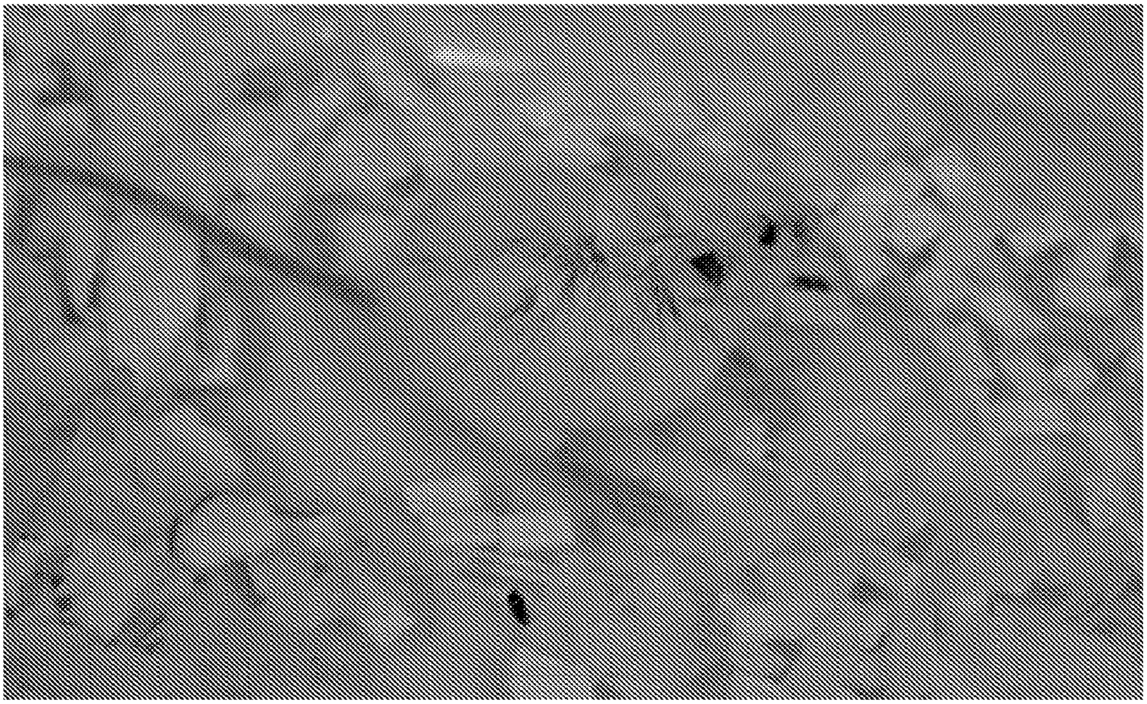

FIG. 1 B shows an untreated $Npc1^{-/-}$ age matched littermate. $Npc1^{-/-}$ mice were observed as having poor coat condition at nine weeks of age, as feeding and drinking had become difficult (see FIG. 1B).

In distinct contrast, FIG. 1A shows an $Npc1^{-/-}$ mouse treated with acetyl-DL-leucine from weaning. $Npc1^{-/-}$ mice treated with acetyl-DL-leucine had a smooth and glossy coat, reminiscent of wild-type ($Npc1^{+/+}$) littermates (see FIG. 1A).

Weight Data

Figure 2A:
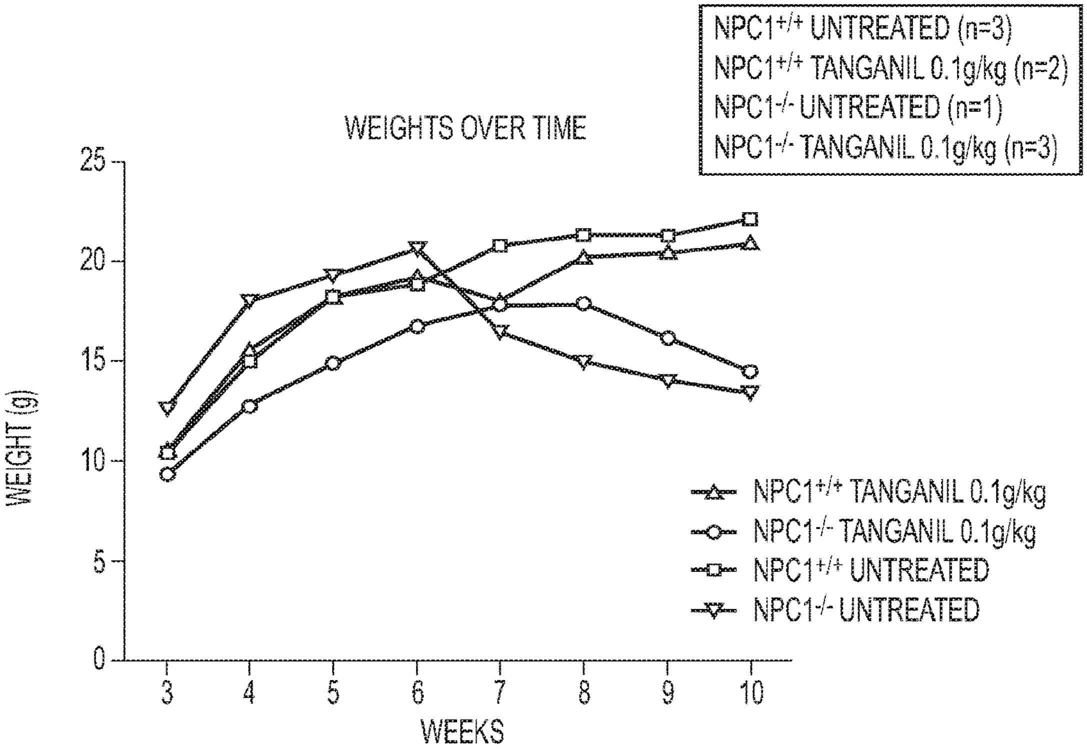
FIGS. 2A and 2B show weight data for $Npc1^{-/-}$ mice compared to wild-type ($Npc1^{+/+}$) mice, with and without acetyl-DL-leucine treatment from weaning.

As can be seen in FIG. 2A, wild-type ($Npc1^{+/+}$) mice progressively put on weight for the duration of the study, i.e. from three weeks to 10 weeks of age. Further, FIG. 2A shows the mean weight per group of mice at each point in time ($Npc1^{-/-}$ untreated, n=1; $Npc1^{-/-}$ acetyl-DL-leucine 0.1 g/kg, n=3; $Npc1^{+/+}$ untreated, n=3; $Npc1^{+/+}$ acetyl-DL-leucine 0.1 g/kg, n=2).

Treatment with acetyl-DL-leucine had no significant effect on this weight gain.

$Npc1^{-/-}$ mice initially put on weight, largely in the same manner as $Npc1^{+/+}$ controls. However, the $Npc1^{-/-}$ mice then began to lose weight from six weeks of age. At the end of the study (10 weeks of age), the mice weighed nearly as little as at just four weeks of age.

Treatment with acetyl-DL-leucine delayed these weight loss symptoms by two weeks compared to the untreated group.

Figure 2B:
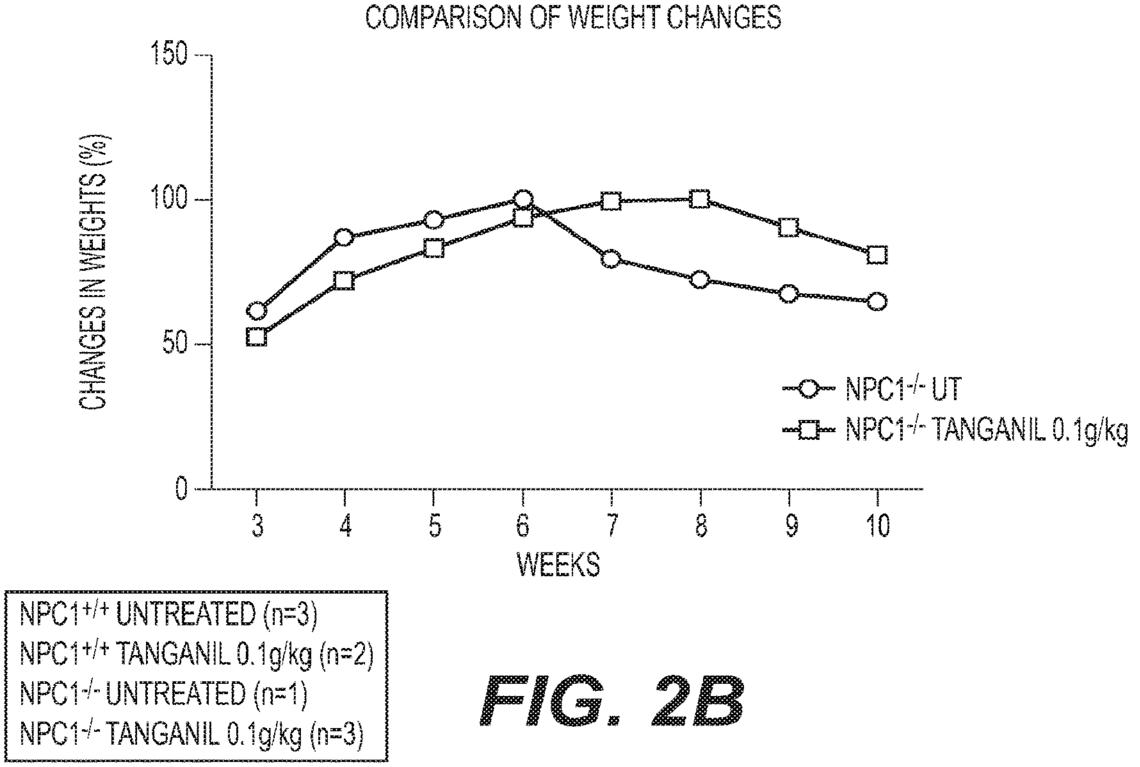
Figure 3A:
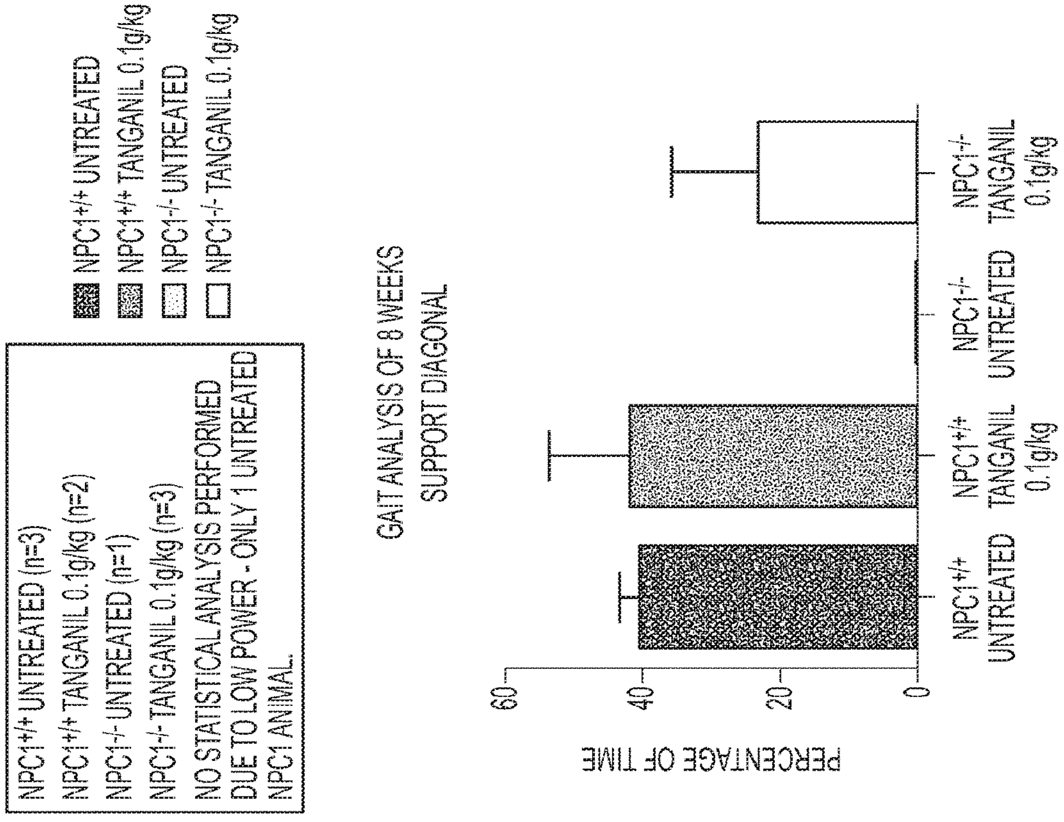
FIGS. 3A-3G show gait analysis data for $Npc1^{-/-}$ mice compared to wild-type ($Npc1^{+/+}$) mice, with and without acetyl-DL-leucinetreatment from weaning. For example, diagonal support, cadence and step sequence data are shown in FIGS. 3A-3C, respectively.
Figure 3B:
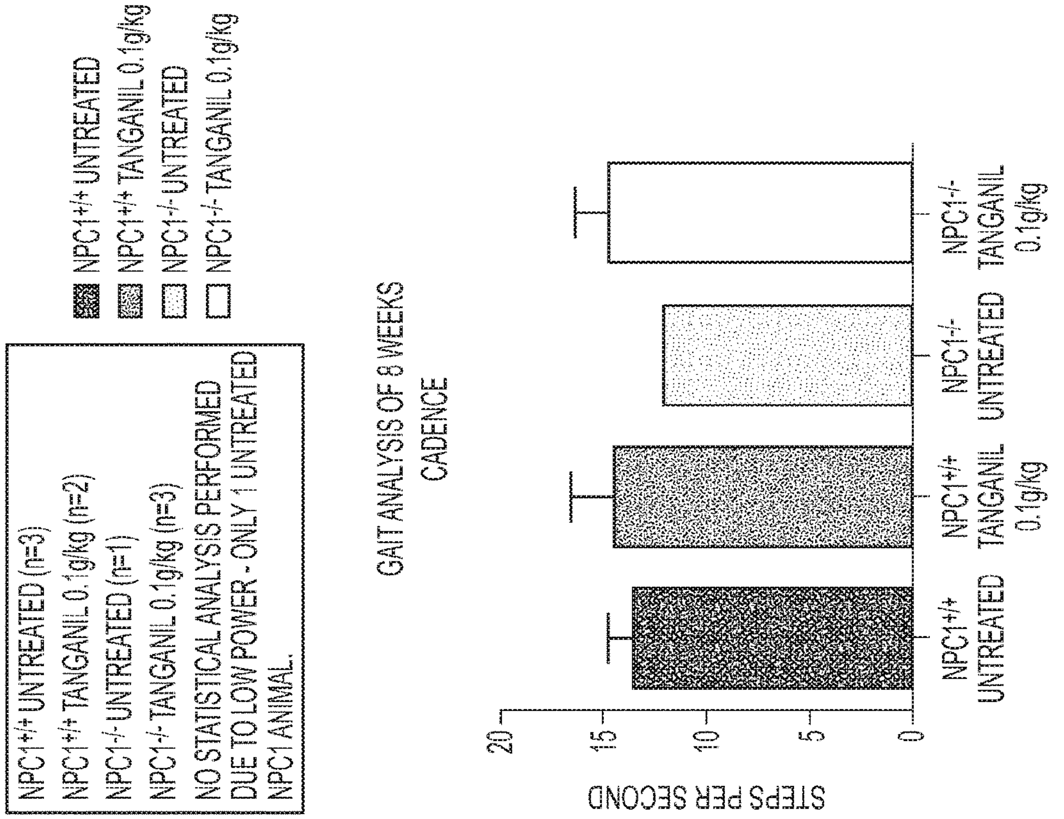
Figure 3D:
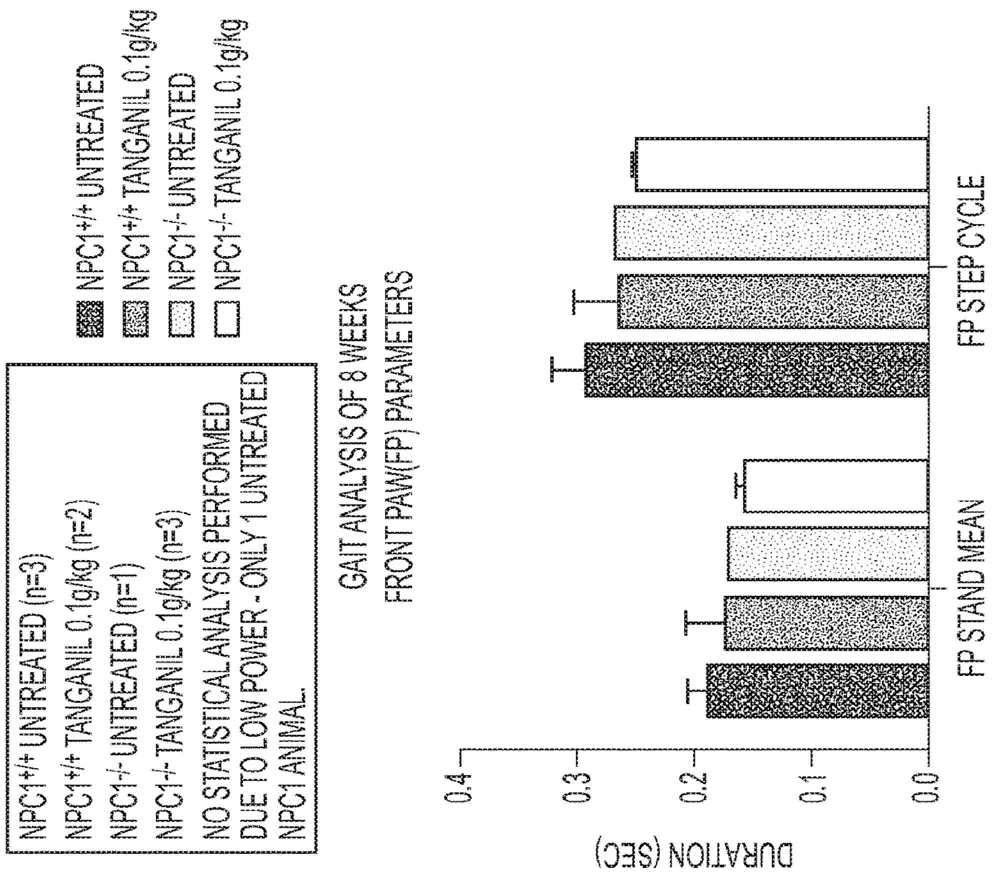
Figure 3C:
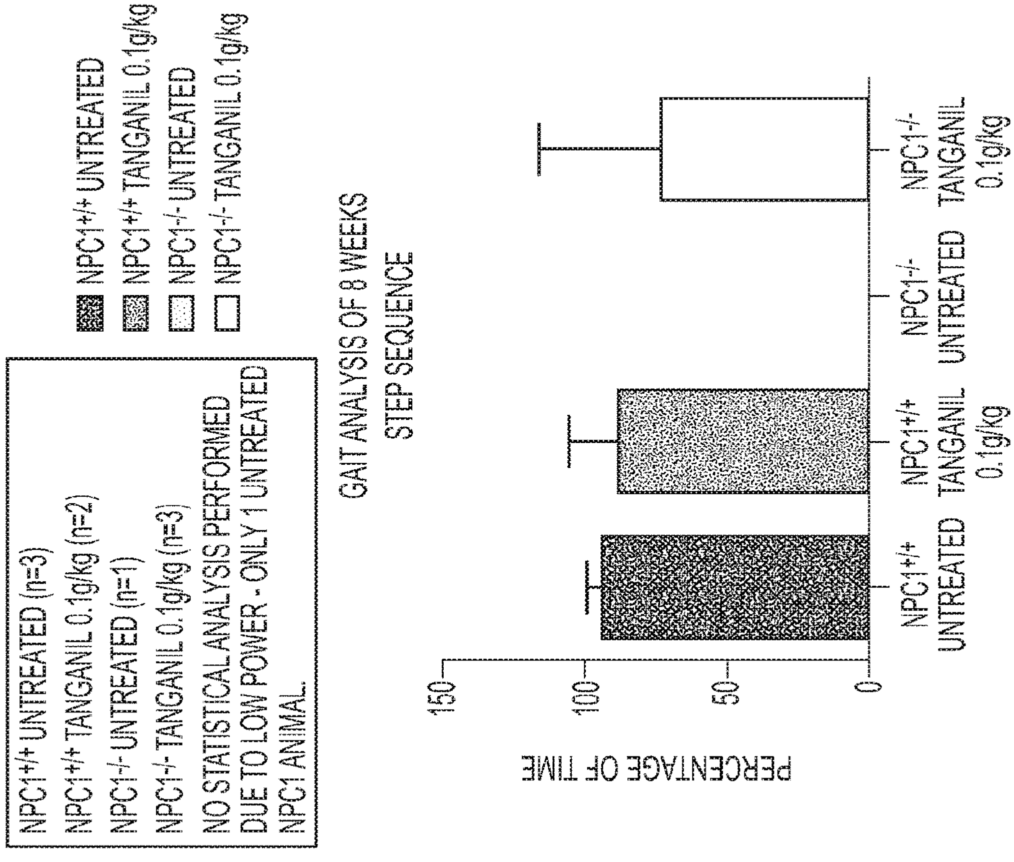
Figure 3F:
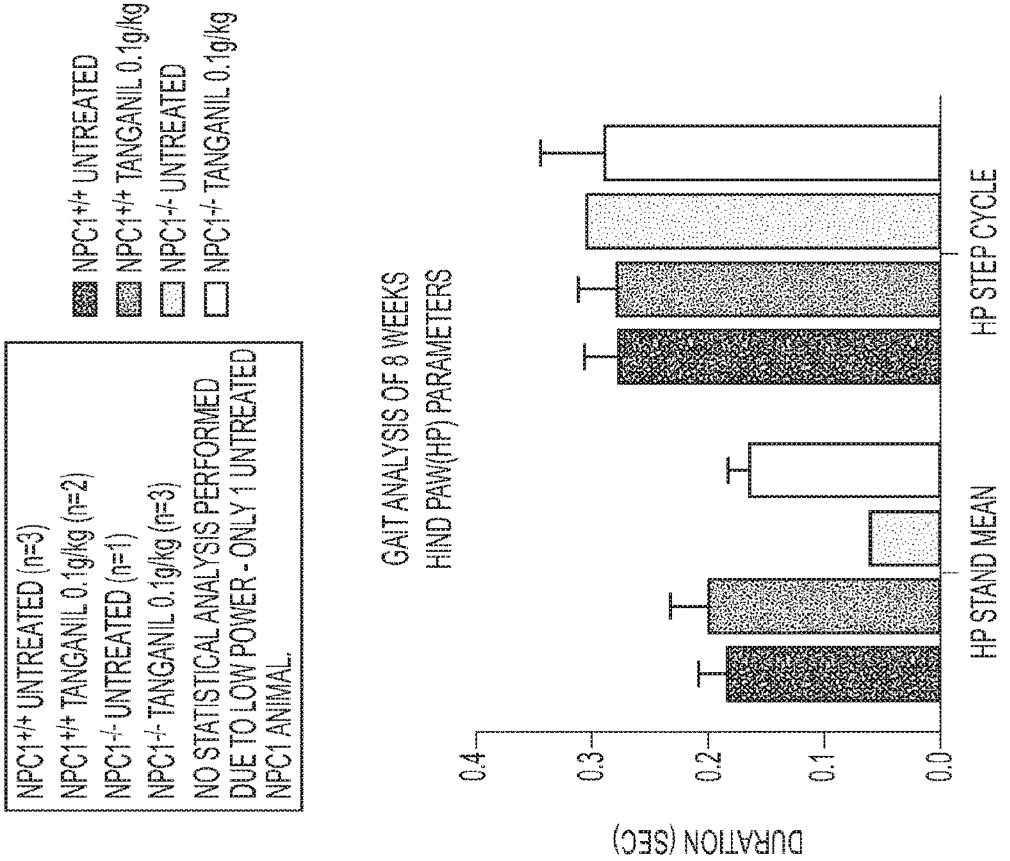
Figure 3E:
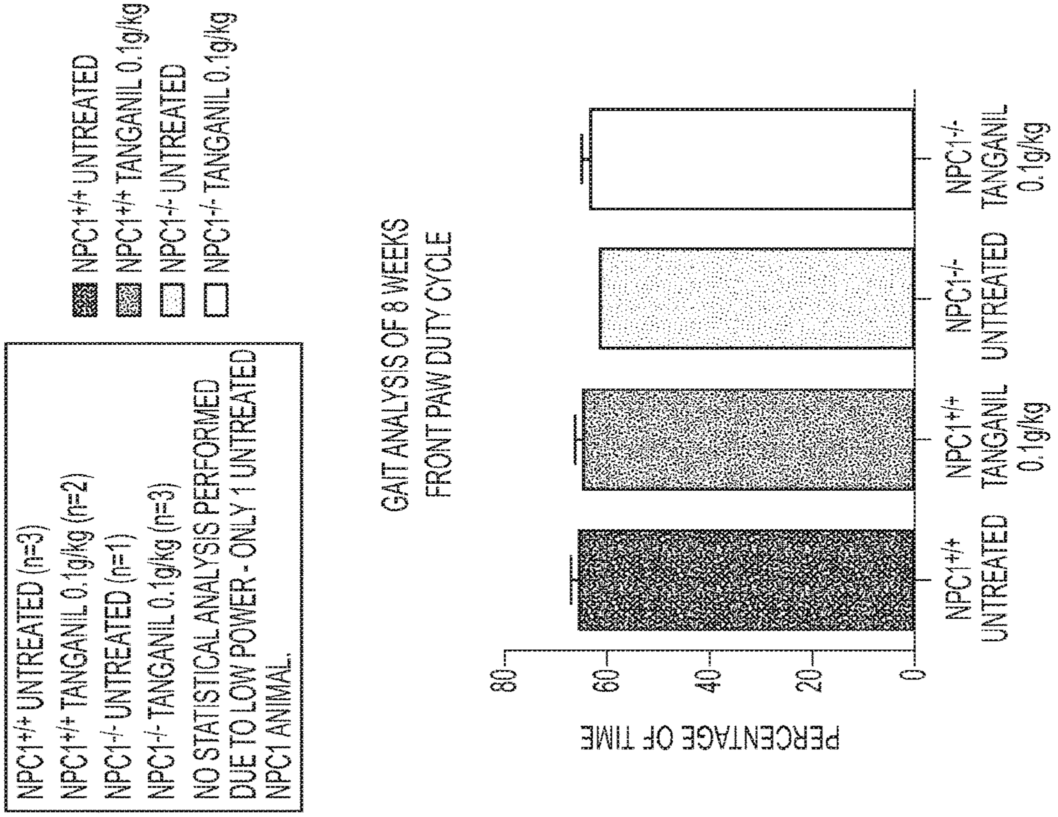
Figure 3G:
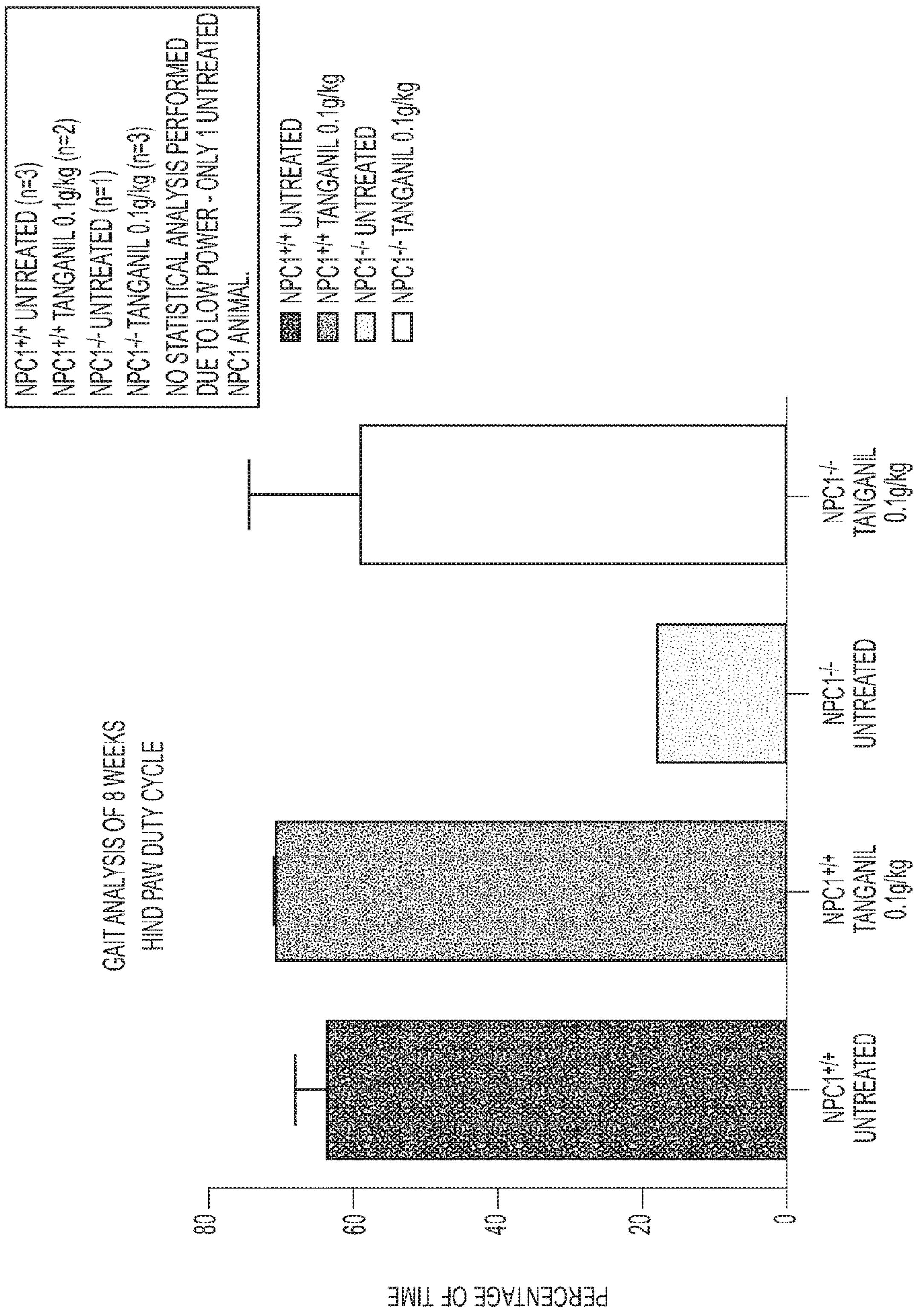
Figure 4A:
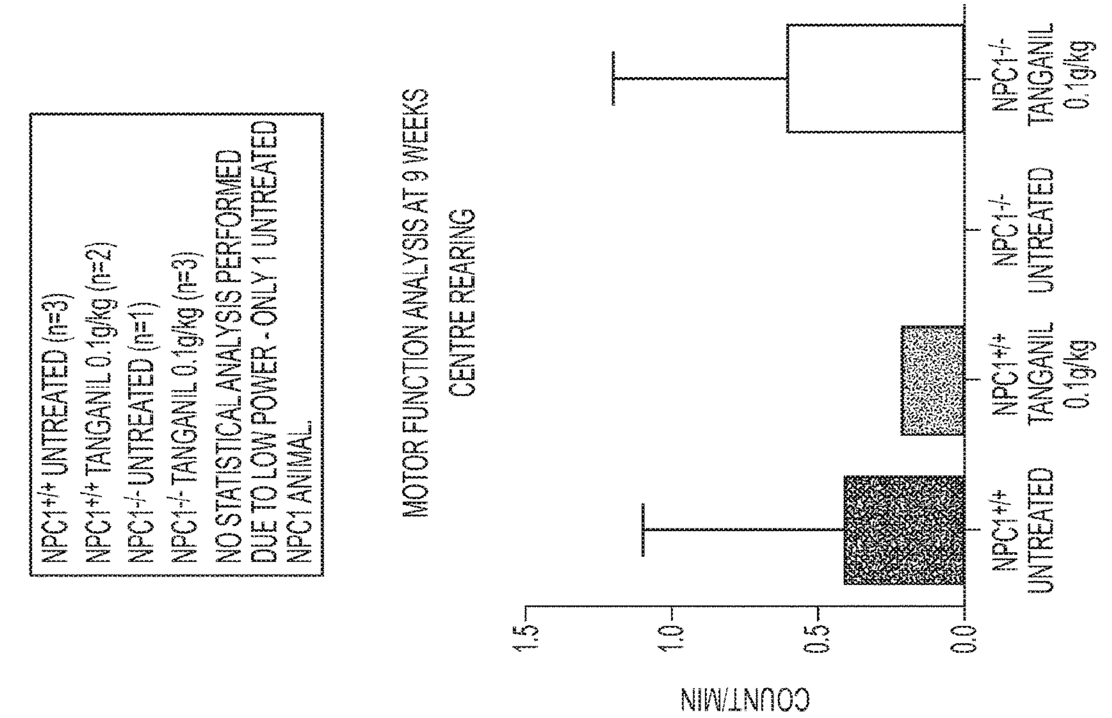
FIGS. 4A-4H show motor function analysis data for $Npc1^{-/-}$ mice compared to wild-type ($Npc1^{+/+}$) mice, with and without acetyl-DL-leucine treatment from weaning. Centre rearing, activity, rearing and front to back (FR) count are shown in FIGS. 4A-4D, respectively. Active time, mobile time, rearing time and total manual rearing count are shown in FIGS. 4E-4H, respectively.
Figure 4B:
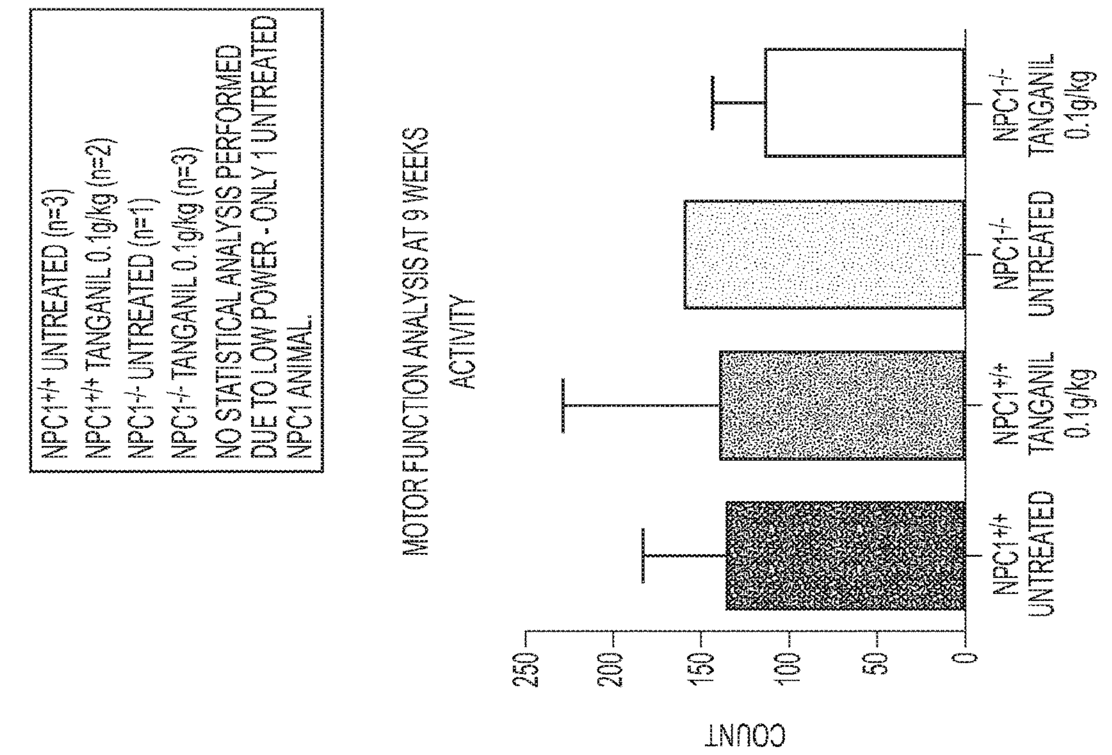
Figure 4C:
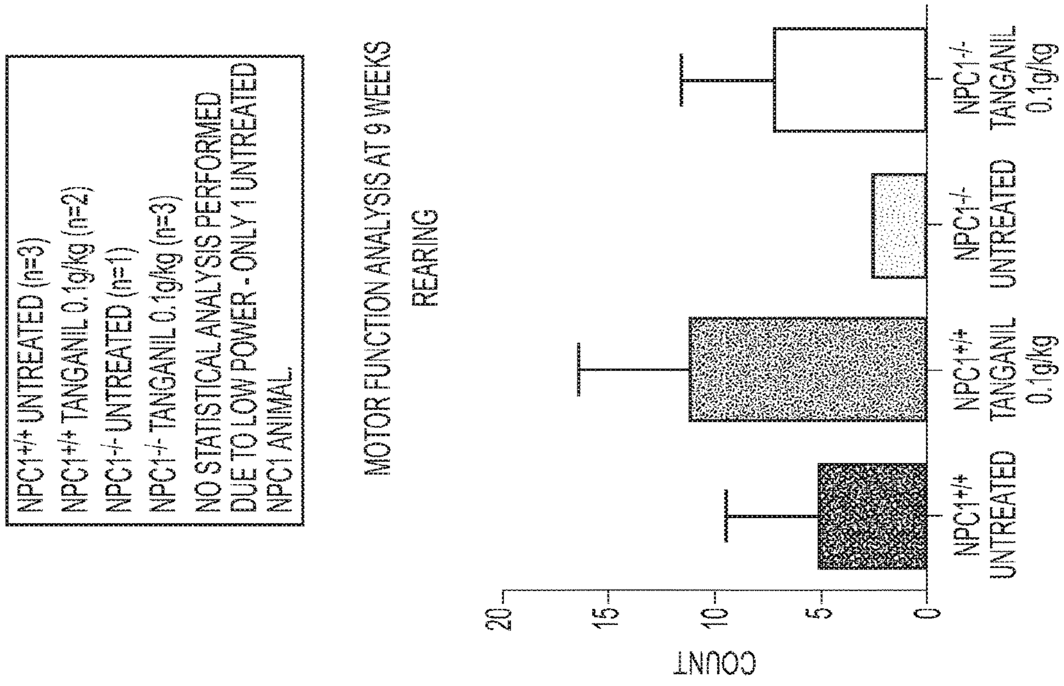
Figure 4D:
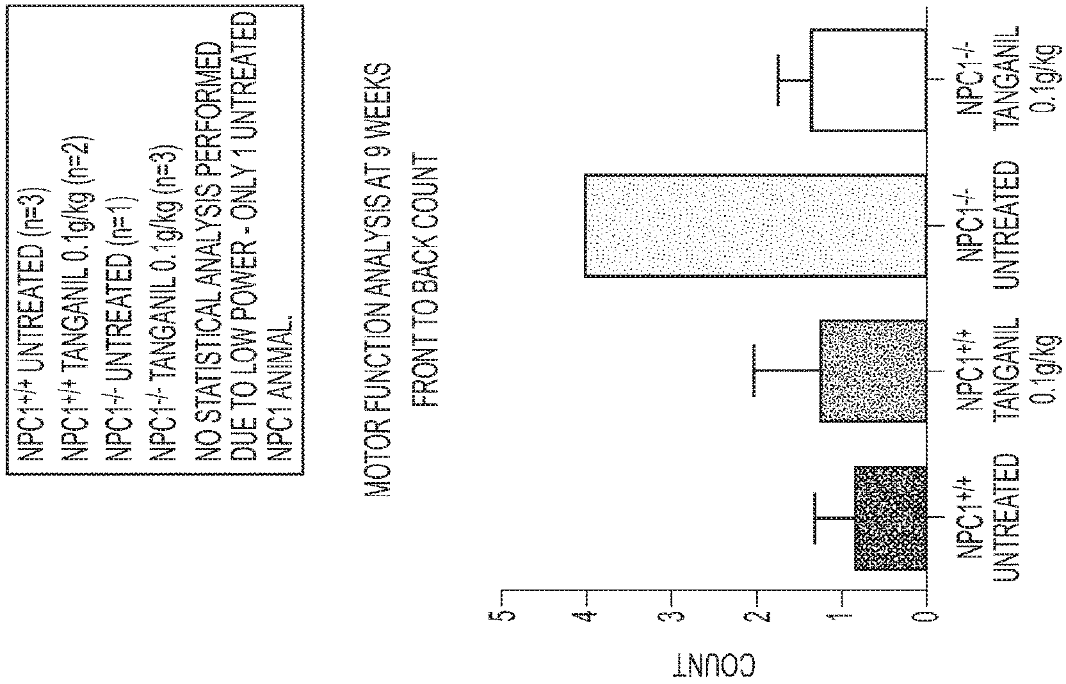
Figure 4E:
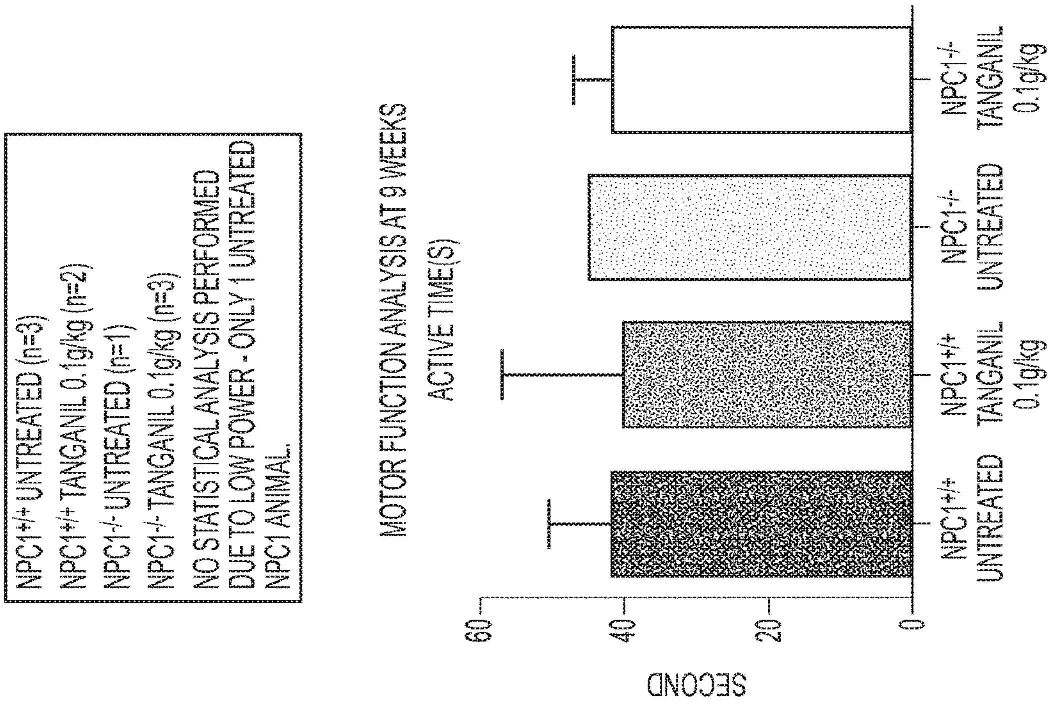
Figure 4F:
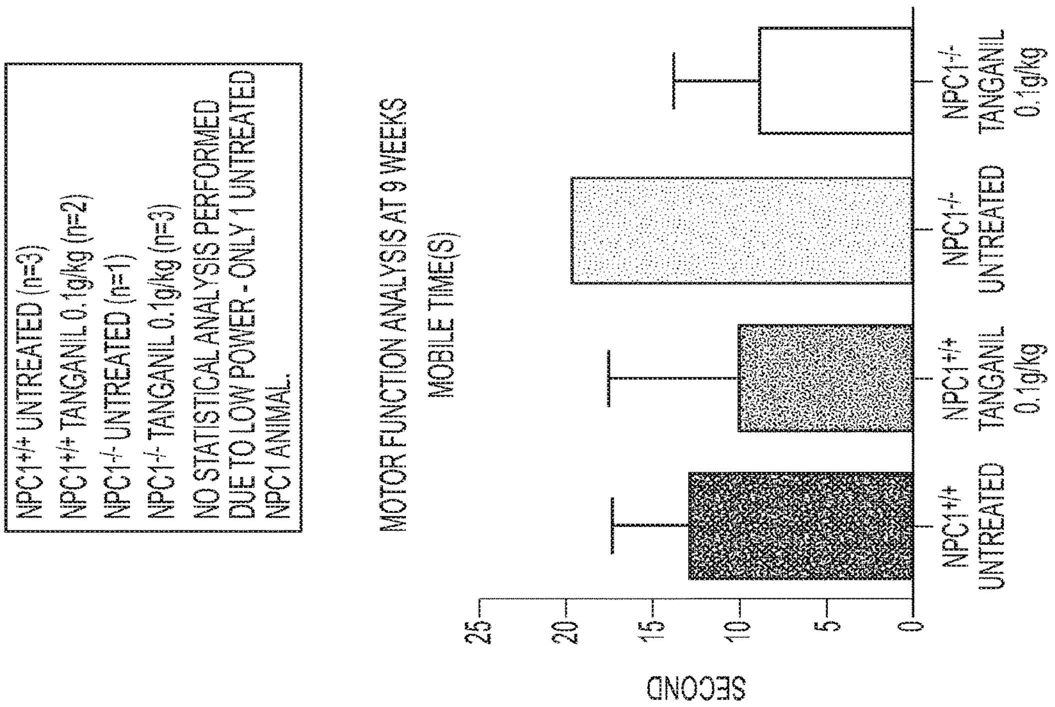
Figure 4H:
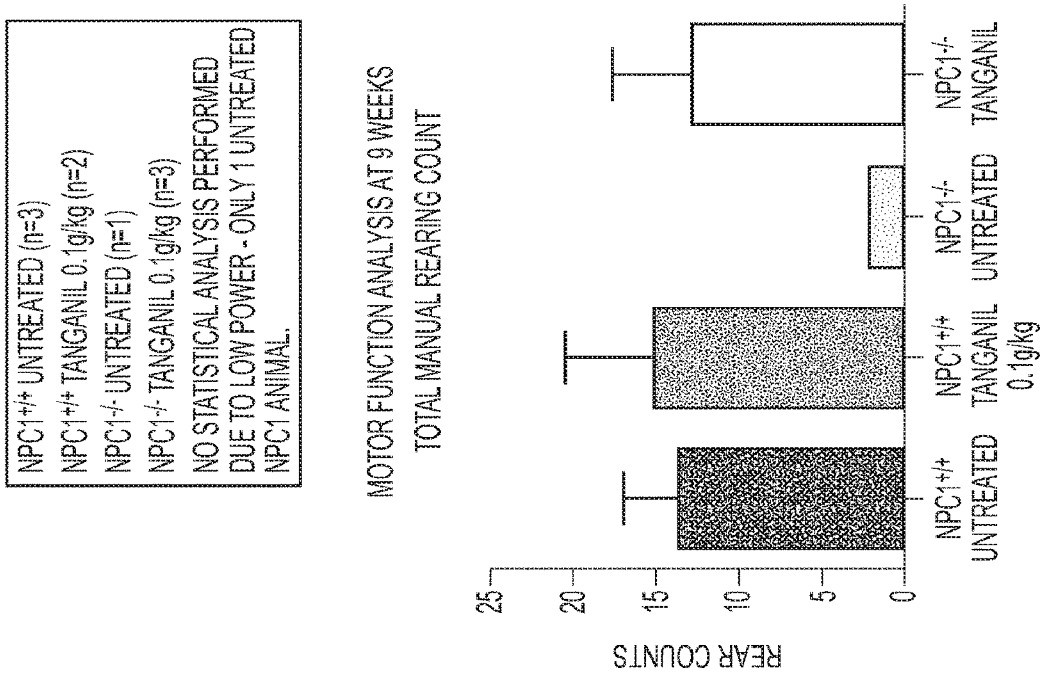
Figure 4G:
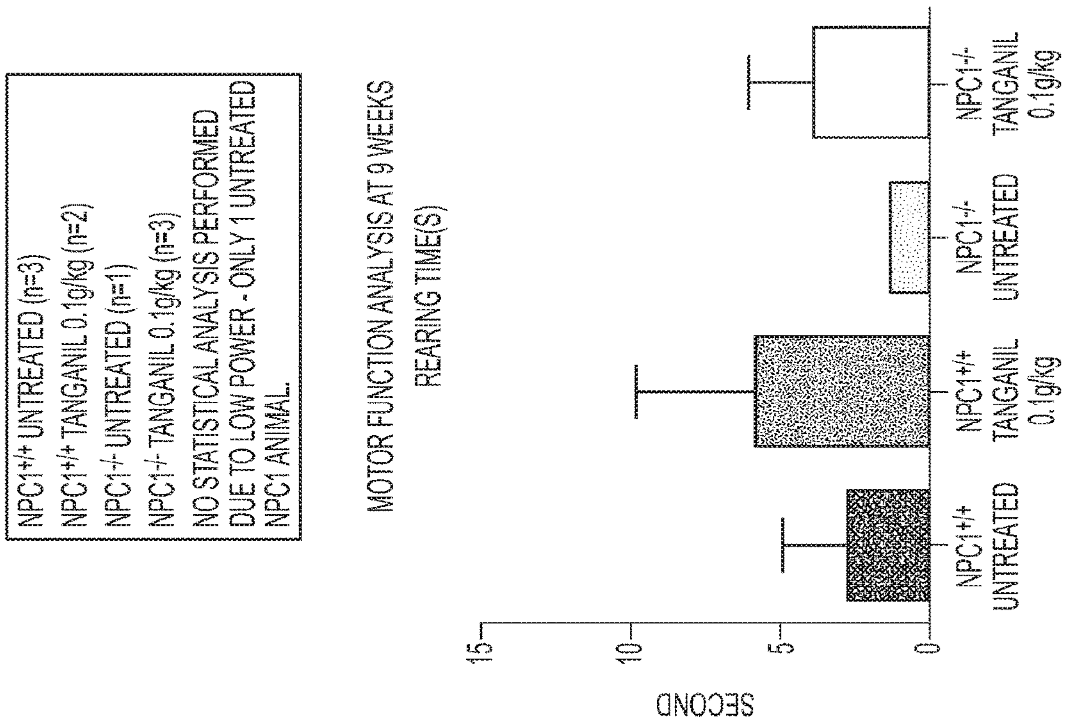

A comparison of the weight changes in $Npc1^{-/-}$ mice, with and without acetyl-DL-leucine treatment, is shown in FIG. 2B. In particular, FIG. 2 B shows the change in weight (%) per group of mice at each point in time, for the $Npc1^{-/-}$ mice only. The beneficial effect of acetyl-DL-leucine treatment in delaying weight loss is clearly evident from this Figure.

Gait Analysis

The results of the gait analysis are shown in FIG. 3. Diagonal support, cadence and step sequence data are shown in FIGS. 3A-3C, respectively. FIGS. 3D and 3E show front paw (FP) data (stand mean and step cycle in FIG. 3D; duty cycle in FIG. 3E). FIGS. 3F and 3G show hind paw (HP) data (stand mean and step cycle in FIG. 3F; duty cycle in FIG. 3G). Data are presented as mean±SEM. n=3 for $Npc1^{+/+}$ untreated, n=2 for $Npc1^{+/+}$ treated, n=1 for $Npc1^{-/-}$ untreated (hence no statistical analysis performed), n=3 for $Npc1^{-/-}$ treated.

The first bar in each graph shows the gait properties of wild-type ($Npc1^{+/+}$) mice.

The second bar in each graph shows the gait properties of wild-type ($Npc1^{+/+}$) mice treated with acetyl-DL-leucine. There was no significant difference in gait properties between these mice and their untreated littermates.

The third bar in each graph shows the gait properties of an $Npc1^{-/-}$ mouse. On the whole, this mouse showed poor gait compared to $Npc1^{+/+}$ mice. The mouse spent extremely little time, if any, in diagonal support (FIG. 3A) or step sequence (FIG. 3C), and its hind paw function in stand mean (FIG. 3F) and duty cycle (FIG. 3G) were also drastically hindered.

The fourth bar in each graph shows the gait properties of $Npc1^{-/-}$ mice treated with acetyl-DL-leucine. These mice demonstrated significantly improved gait compared to their untreated littermates. In fact, they showed similar gait properties to $Npc1^{+/+}$ mice.

Motor Function Analysis

Analysis at eight weeks of age revealed no difference in motor function properties between $Npc1^{-/-}$ and wild-type ($Npc1^{+/+}$) mice (data not shown).

By nine weeks of age, however, defects in motor coordination had become apparent.

The results of the motor function analysis at nine weeks are shown in FIG. 4. Centre rearing, activity, rearing and front to back (FR) count are shown in FIGS. 4A-4D, respectively. Active time, mobile time, rearing time and total manual rearing count are shown in FIGS. 4E-4H, respectively. Data are presented as mean±SEM. n=3 for $Npc1^{+/+}$ untreated, n=2 for $Npc1^{+/+}$ treated, n=1 for $Npc1^{-/-}$ untreated (hence no statistical analysis performed), n=3 for $Npc1^{-/-}$ treated.

The first bar in each graph shows the motor function properties of wild-type ($Npc1^{+/+}$) mice.

The second bar in each graph shows the motor function properties of wild-type ($Npc1^{+/+}$) mice treated with acetyl-DL-leucine. There was no significant difference in motor function properties between these mice and their untreated littermates.

The third bar in each graph shows the motor function properties of an $Npc1^{-/-}$ mouse. On the whole, this mouse showed poor motor function compared to $Npc1^{+/+}$ mice. The mouse spent extremely little time, if any, rearing (panel H), particularly on its hind legs unsupported (panel A).

The fourth bar in each graph shows the motor function properties of $Npc1^{-/-}$ mice treated with acetyl-DL-leucine. These mice demonstrated significantly improved motor function compared to their untreated littermates. In fact, they showed similar motor function properties to $Npc1^{+/+}$ mice.

Lifespan

Figure 5:
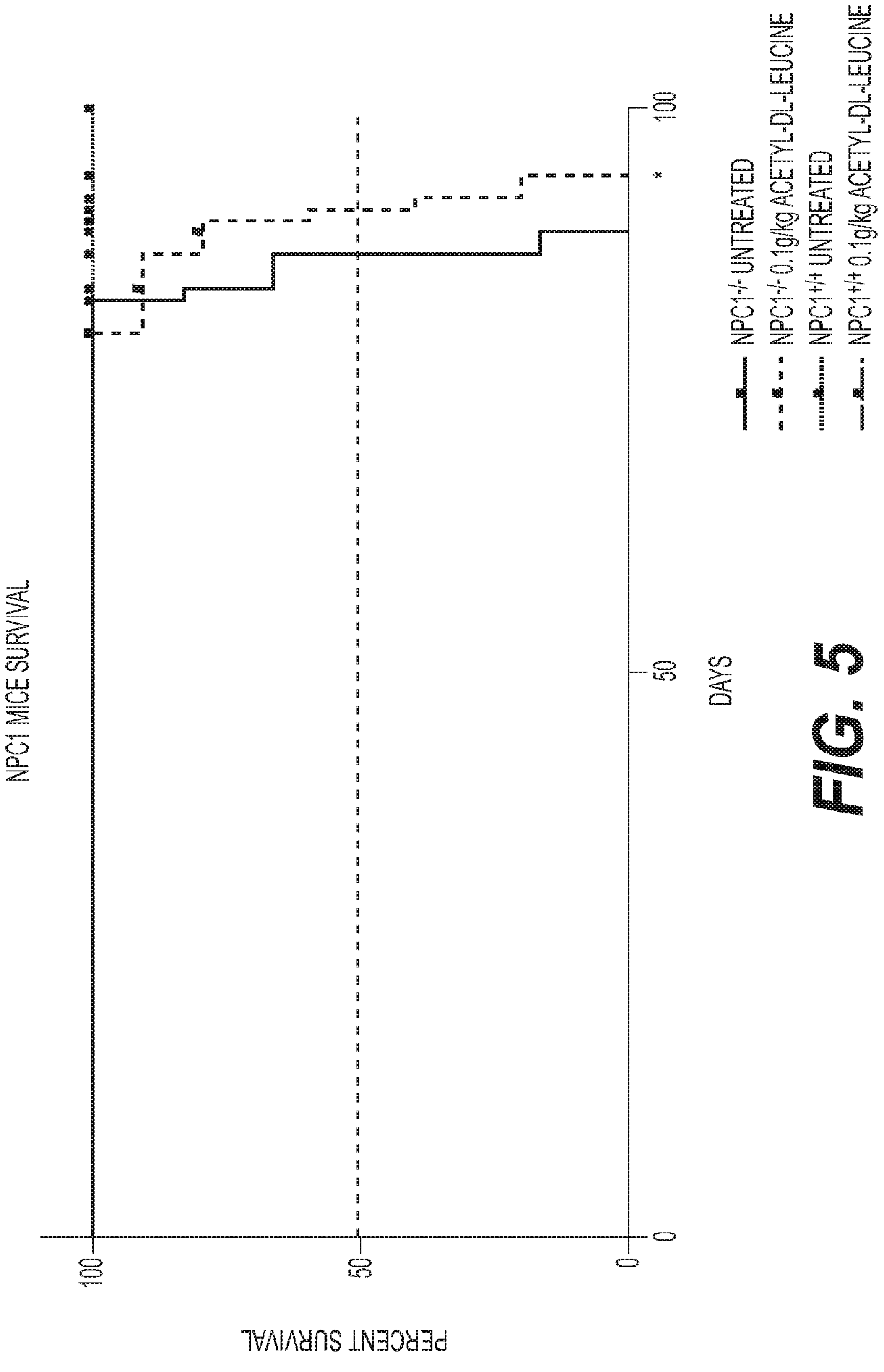
FIG. 5 shows that treatment with acetyl-DL-leucine (0.1 g/kg from 3 weeks of age) is associated with a small but statistically significant increase in lifespan in the $Npc1^{-/-}$ mouse.

It was also observed that treatment of the $Npc1^{-/-}$ mouse with acetyl-DL-leucine (0.1 g/kg from 3 weeks of age) is associated with a statistically significant increase in lifespan (FIG. 5). This data further indicates the effect of acetyl-leucine in delaying the onset of the disease.

Conclusion

Where $Npc1^{-/-}$ mice had discernible indication of disease that distinguished them from wild-type littermates from 5-6 weeks of age, $Npc1^{-/-}$ littermates treated with acetyl-DL-leucine from weaning did not display such symptoms until two or more weeks later. Treatment of $Npc1^{-/-}$ mice with acetyl-DL-leucine delayed onset and progression of NPC symptoms and showed evidence of neuroprotection.

It is reasonable to expect that, as acetyl-DL-leucine provided general neuroprotection, that the results observed in NPC will also be observed in other neurodegenerative disorders, and neurodegenerative disorders that are associated with defects in lysosomal storage.

Example 2

Methods

A fibroblast cell line from an NPC patient was treated for 3 days with N-acetyl-DL-leucine (1 mM) and relative lysosomal volume was quantified via LysoTracker, a fluorescent dye that accumulates in acidic organelles. Increased LysoTracker fluorescence is indicative of an increase in lysosomal size and/or number, and is a hallmark of NPC cells.

In addition, fibroblasts derived from Niemann-Pick A (NPA), Mucolipidosis Type II (MLII), Mucopolysaccharidosis Type IIIB (MPS IIIB), Aspartylglucosaminuria, Mucolipidosis Type IIIA (MLIIIA), and Mucopolysaccharidosis Type VII (MPS VII) patients were treated with acetyl-DL-Leucine (1 mM) for 6 days and lysosomal volume was quantified via LysoTracker.

Results

Figure 6A:
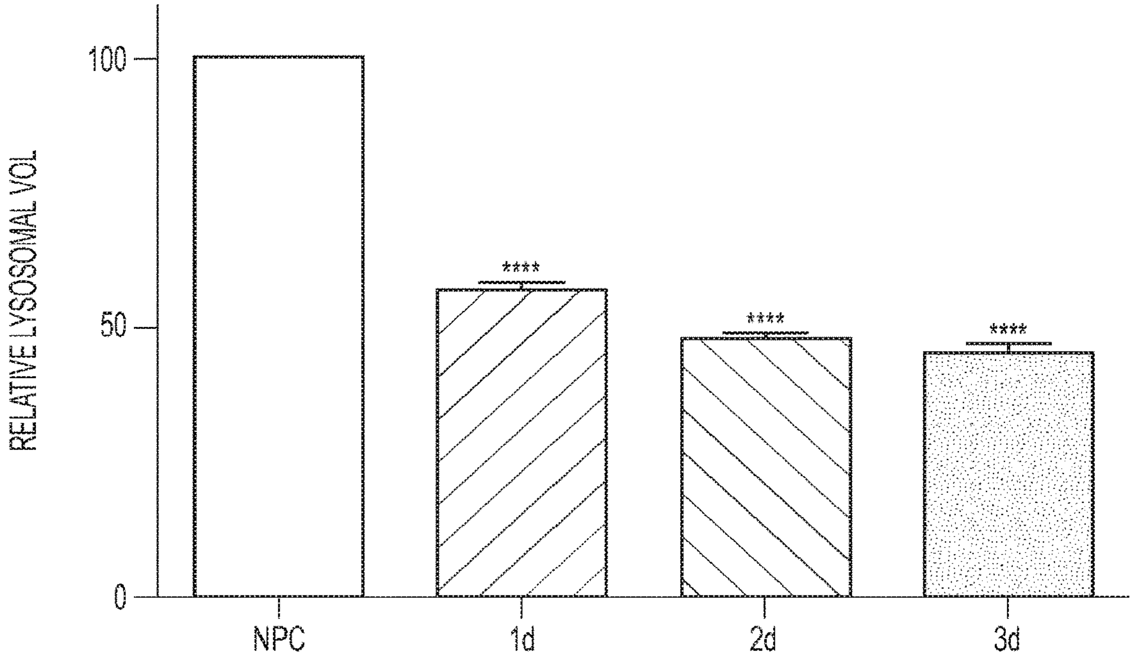
FIGS. 6A and 6B shows the reduction of lysosomal volume in non-neuronal NPC cells following treatment with acetyl-DL-leucine.
Figure 6B:
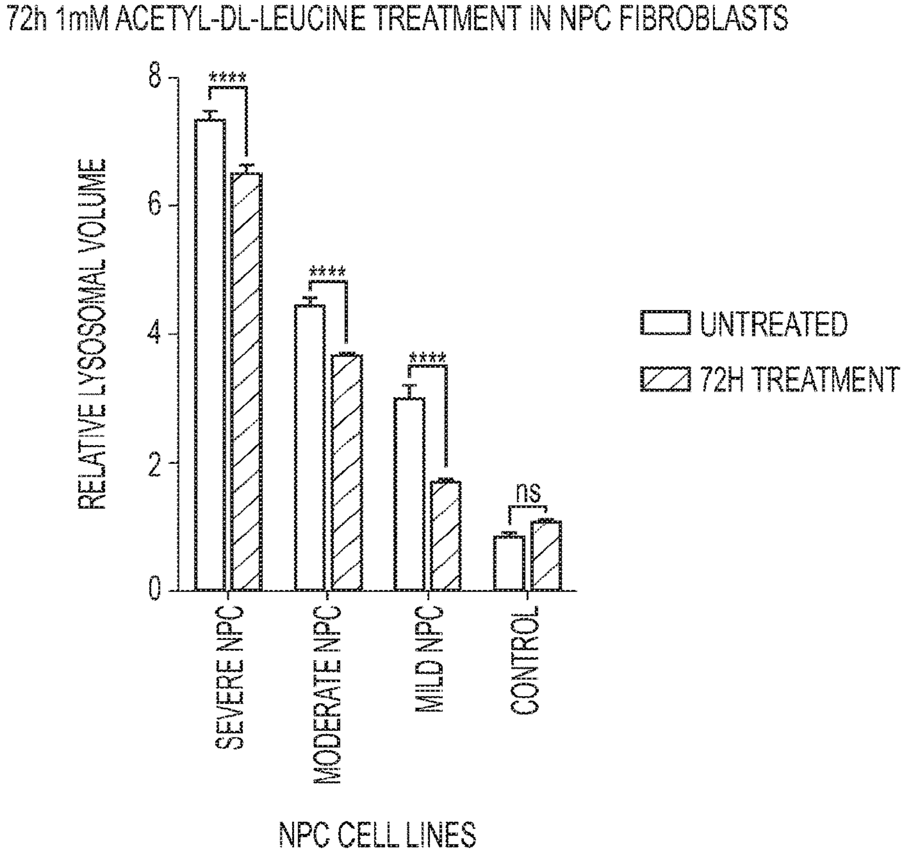
Figure 6C:
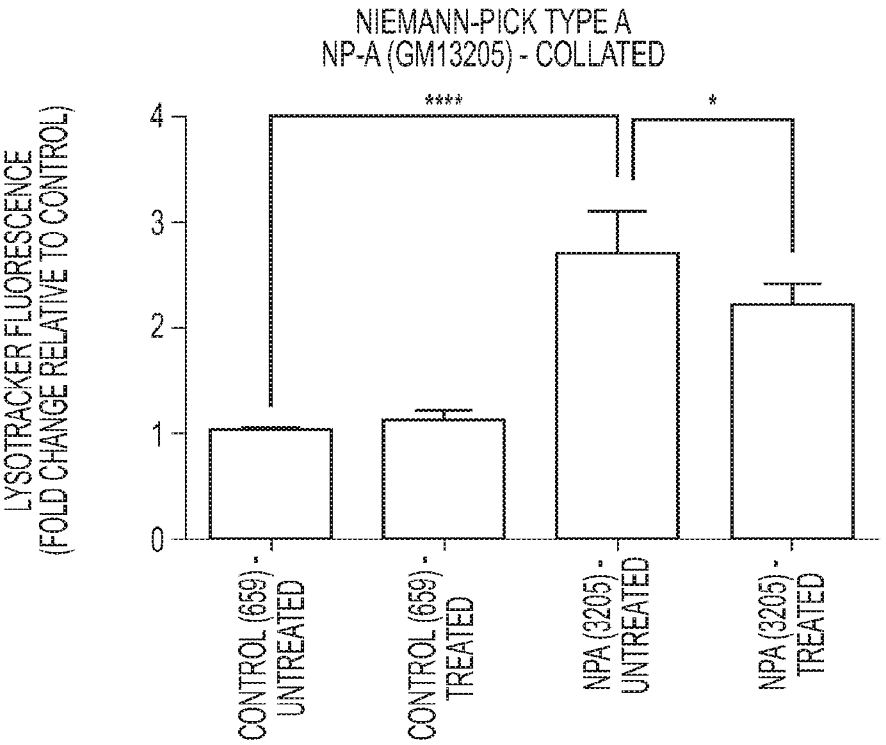
FIGS. 6C-6H show the effect of treatment with acetyl-DL-Leucine on lysosomal volume in NPA, MLII, MPS IIIB, Aspartylglucosaminuria, MLIIIA, and MPS VII patient fibroblasts, respectively.
Figure 6D:
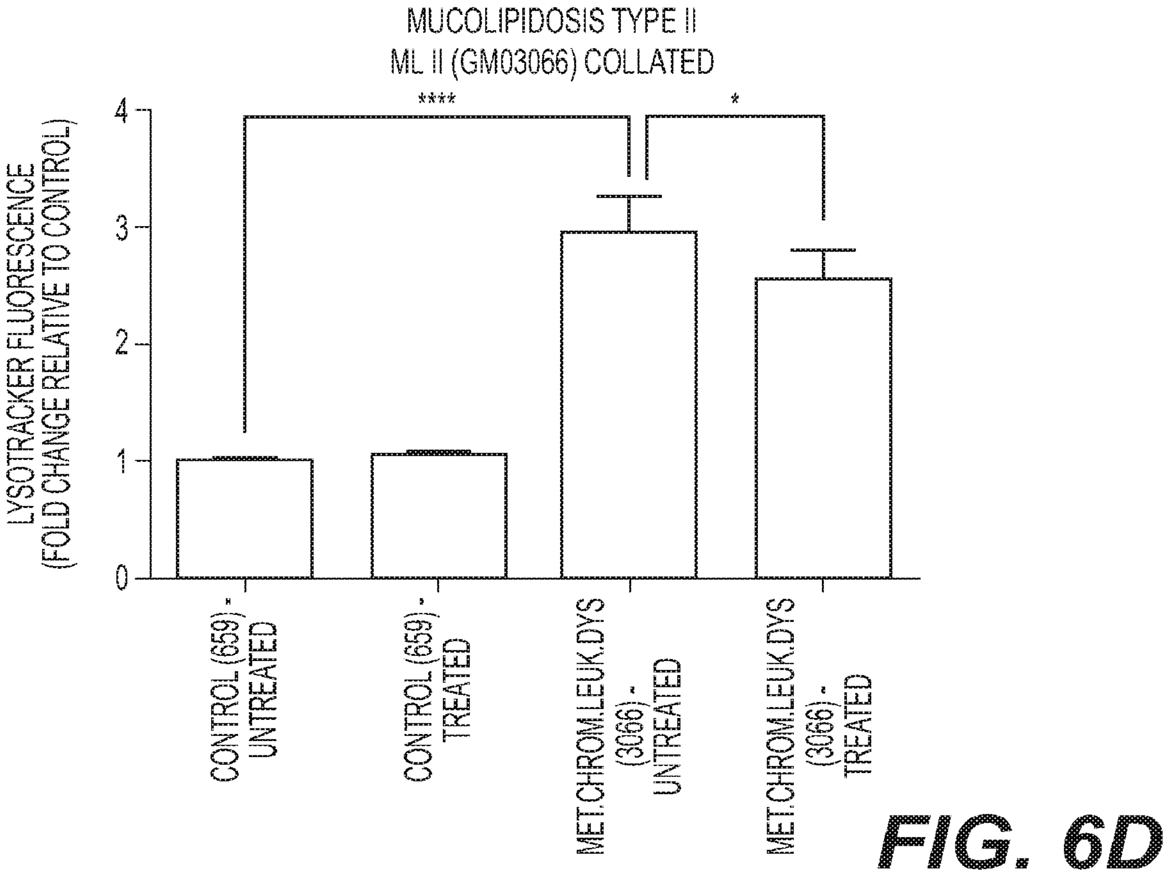
Figure 6E:
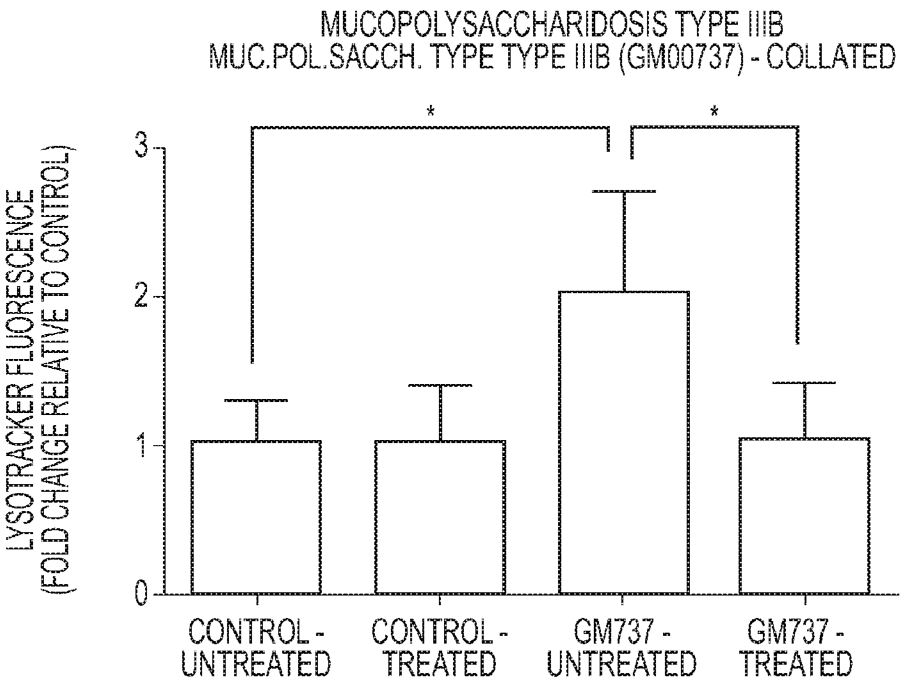

Treatment of fibroblasts derived from an NPC patient of mild clinical severity with 1 mM N-acetyl-DL-leucine was associated with a significant decrease in LysoTracker fluorescence, indicative of reduced lysosomal volume over time (FIG. 6A). These findings were replicated in fibroblasts obtained from additional NPC patients of variable clinical severity that were treated with 1 mM N-acetyl-DL-leucine for 72 hours (FIG. 6B).

Figure 6F:
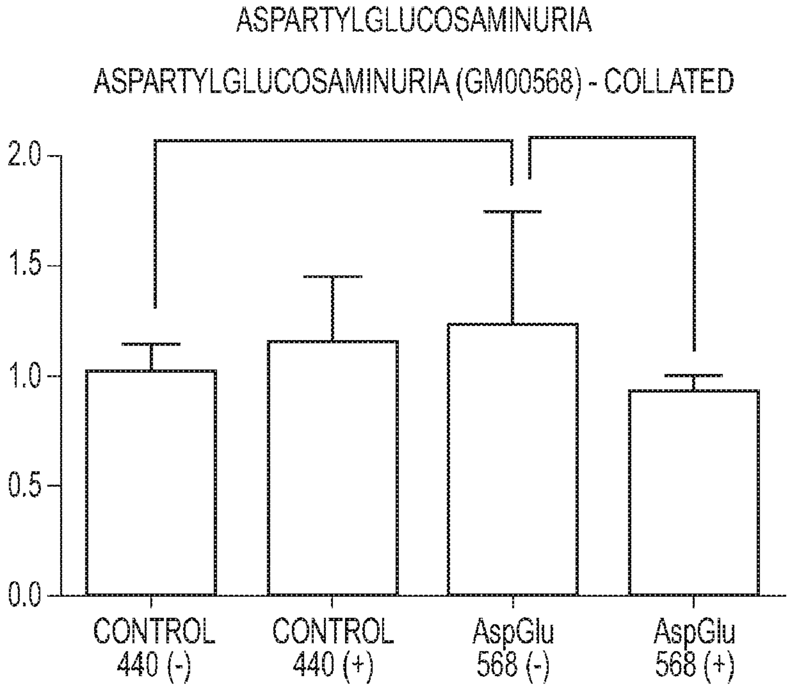
Figure 6G:
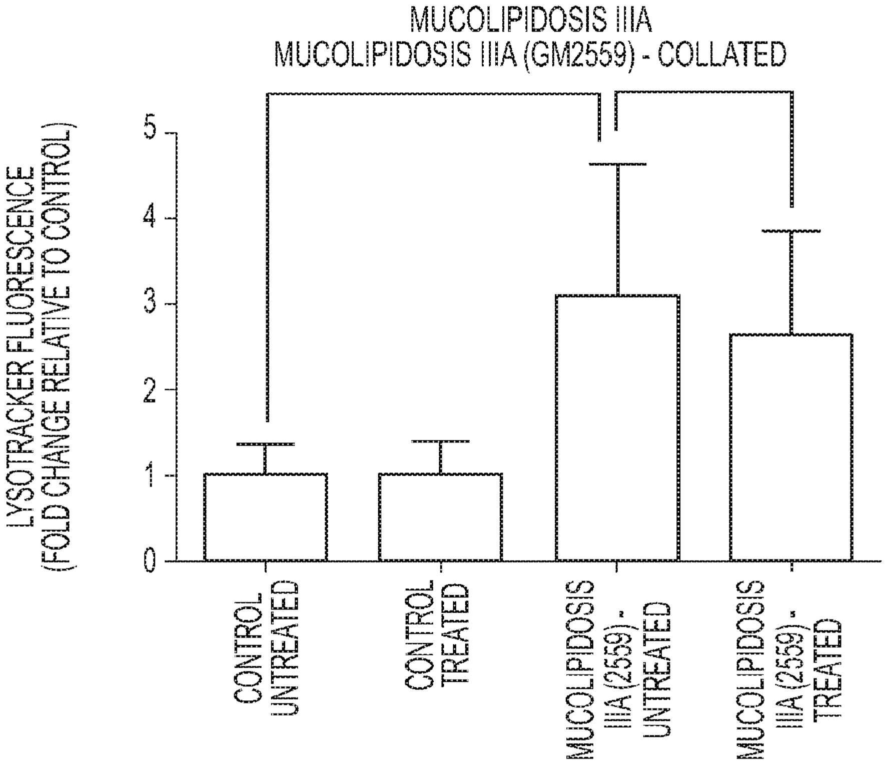
Figure 6H:
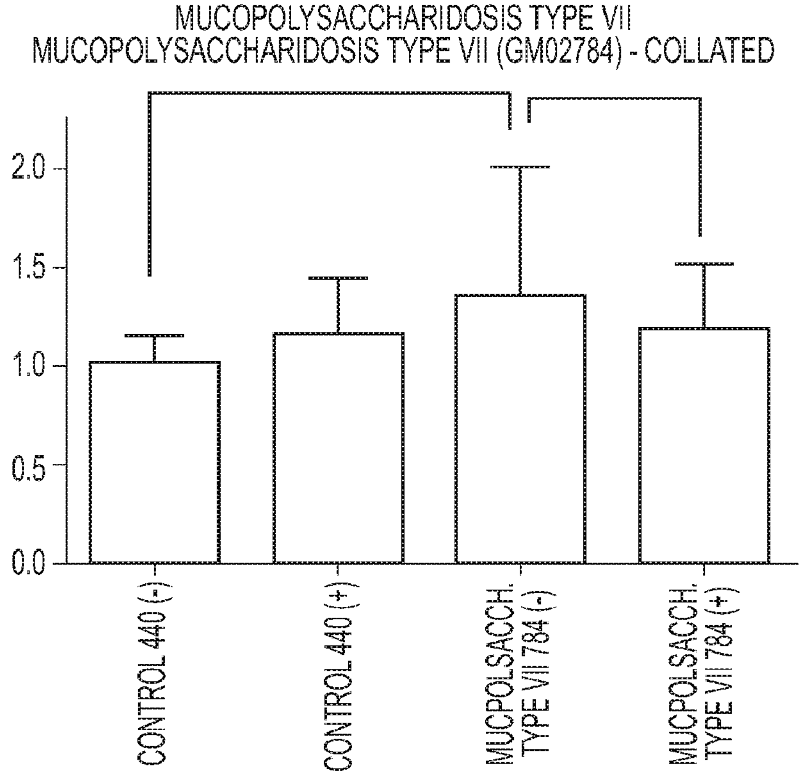

Fibroblasts derived from NPA, and MLII, MPS IIIB, Aspartylglucosaminuria, MLIIIA, and MPS VII patients were observed to have elevated LysoTracker fluorescence levels relative to age-matched wild-type controls (FIGS. 6C-6H). This is indicative of an expanded lysosome occurring as a result of lipid storage compared to fibroblasts from healthy individuals. Treatment with acetyl-leucine was associated with a statistically significant reduction in LysoTracker fluorescence toward control level in both the NPA, and MLII, and MPS IIIB fibroblasts relative to untreated NPA, and MLII, and MPS IIIB fibroblasts, respectively (FIGS. 6C-6E), and was associated with a trend in reducing LysoTracker fluorescence toward control level in the asp artylglucosaminuria, MLIIIA, and MPS VII fibroblasts relative to untreated aspartylglucosaminuria, MLIIIA, and MPS VII fibroblasts, respectively (FIGS. 6F-6H). The reduction in LysoTracker fluorescence was indicative of a decrease in lysosomal volume (FIGS. 6C-6H and 6D). Data presented in FIGS. 6A-6D show the results after 6 days of the treatment for each cell line, respectively with 1 mM acetyl-leucine, with lysosomal volume expressed as fold change relative to untreated wild-type fibroblasts. The asterisks (*/****) indicates a p-values of (<0.05/0.001) versus untreated disease fibroblasts.

Conclusion

N-acetyl-DL-leucine treatment was associated with the rectification of disturbed lysosomal storage by reducing lysosomal volume and thus acetyl-leucine directly corrected a phenotype of these lysosomal storage disorders. These diseases represent different classes of LSDs, and thus these results further support utility of acetyl-leucine's effect against a broad range of lysosomal storage disorders.

Example 3

Sandhoff disease is a disorder which may result from the autosomal recessive inheritance of mutations in the HEXB gene, which encodes the beta-subunit of beta-hexosaminidase. As a result of this, GM2 ganglioside fails to be degraded and accumulates within lysosomes in cells of the periphery and the central nervous system (CNS).

This study made use of a mouse model of Sandhoff disease, the $Hexb^{-/-}$ mouse, as described in Jeyakumar et al. (Jeyakumar, M. et al. (1999) *Proc. Natl. Acad. Sci. USA* 96: 6388-6393).

Wild-type ($Hexb^{+/+}$) mice were used as controls.

Lifespan

Figure 7A:
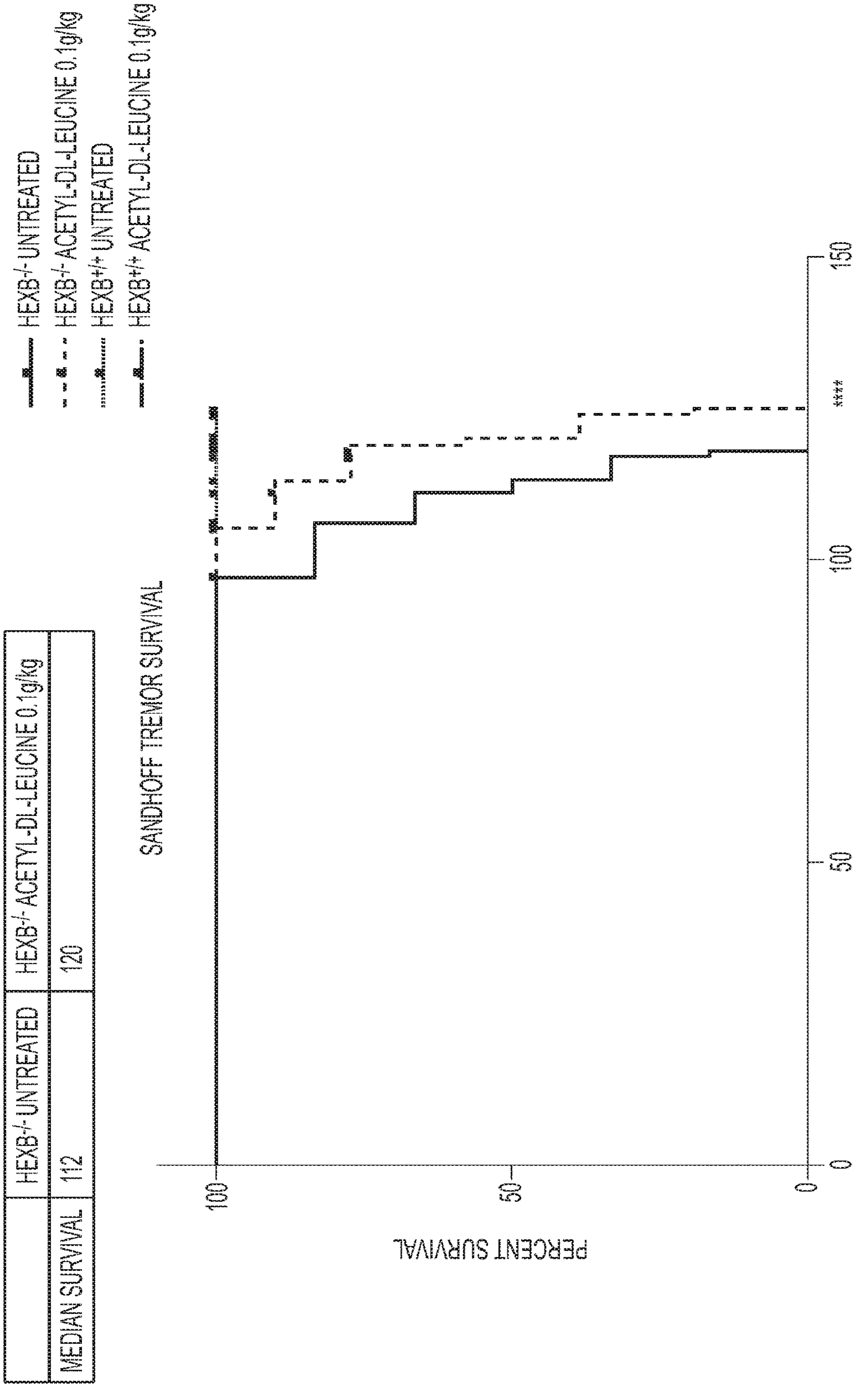
FIG. 7A shows a survival curve representing mortality in untreated or acetyl-leucine-treated wild-type and Sandhoff mice.

Treatment with acetyl-DL-Leucine was associated with a statistically significant increase in the lifespan of the Sandhoff mouse (FIG. 7A). In FIG. 7A, acetyl-leucine-treated mice were treated with 0.1 g/kg acetyl-leucine from 3 weeks of age. The asterisks (*) indicates a p-value of <0.05 vs untreated Sandhoff mice. Data is average of n=6 mice per group. Without treatment, the median survival time of Sandhoff mice was 112 days. Treatment with acetyl-leucine (0.1 g/kg body weight since 3 weeks of age) increased the median lifespan to 120 days.

Motor Function

Treatment of Sandhoff mice with acetyl-leucine gave rise to improvements in motor function as indicated by bar crossing and step cycle studies.

Bar Crossing Test

The bar crossing test is a method for assessing motor function in mice in which the mouse is placed hanging from the centre of a horizontal bar by its front limbs. A wild-type mouse with normal motor function will be able to engage its hind limbs and thereby move to one of the platforms at either end of the bar, and in doing so complete the test.

An untreated Sandhoff mouse is able to complete the test up until around 11 weeks of age. After this point motor function and hind-limb mobility/engagement have deteriorated to the point to which the mouse cannot complete the test, and will drop from the bar onto the padded surface below.

Figure 7B:
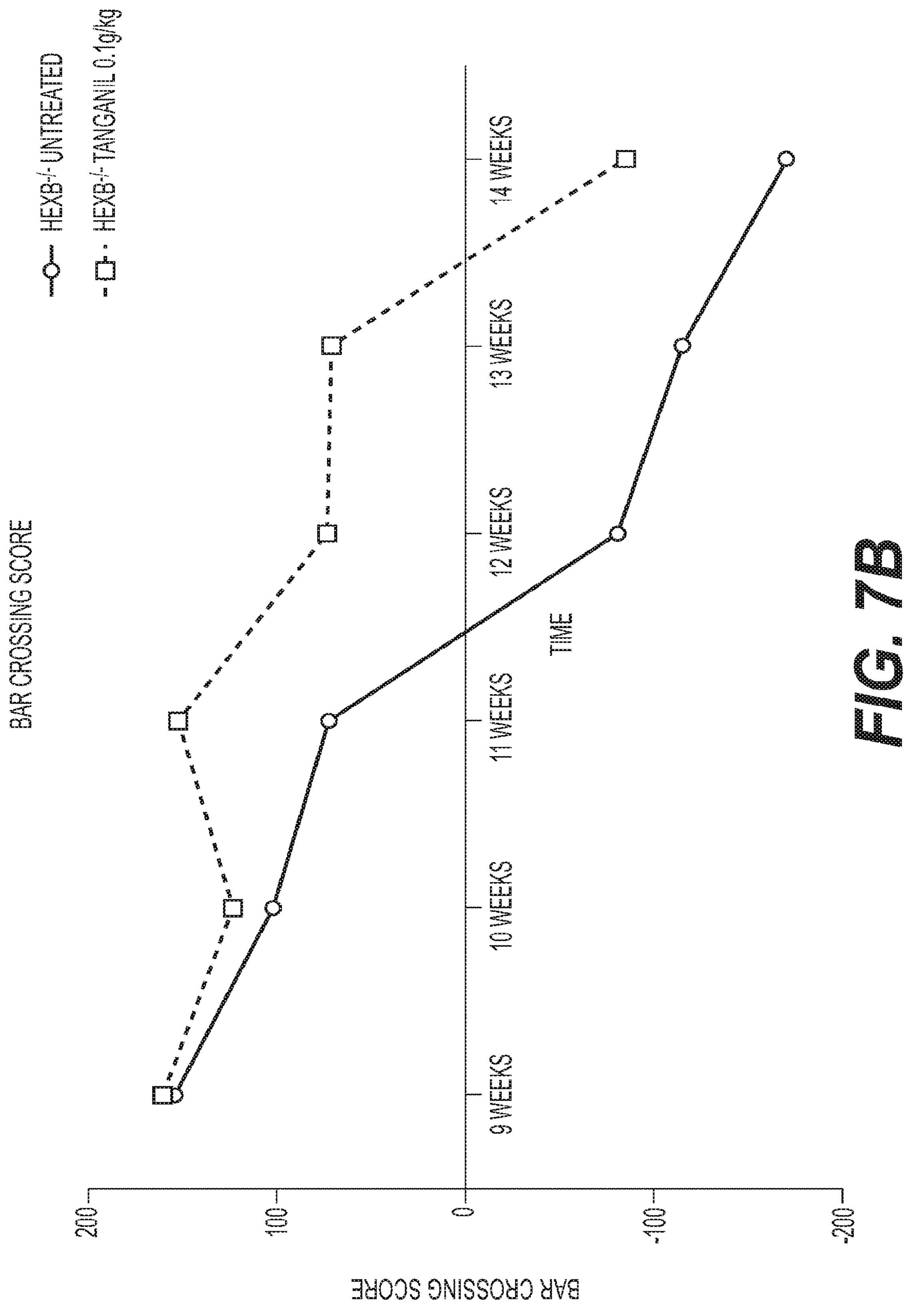
FIG. 7B shows bar crossing scores for untreated and acetyl-leucine-treated Sandhoff model mice.

Treatment of the Sandhoff mouse model with acetyl-DL-leucine (0.1 g/kg body weight from 3 weeks of age) was associated with improved motor function and hind-limb mobility/engagement as assessed via the bar-crossing test (FIG. 7B). In FIG. 7 B, acetyl-leucine treatment of 0.1 g/kg body weight was provided from 3 weeks of age. The acetyl-leucine treated Sandhoff mice retained the ability to complete the test up to 13 weeks of age (inclusive). Data shown is the mean of 6 mice per group. The treated Sandhoff mice retained the ability to complete the test up to 13 weeks of age (inclusive).

Step Cycle

Step cycle is the length of time taken during locomotion by a limb from the time it leaves the ground until it leaves the ground on the next occasion.

Step cycle time was assessed at 12 weeks of age in untreated and acetyl-leucine treated Sandhoff model mice. Acetyl-leucine treatment constituted 0.1 g/kg body weight acetyl-leucine from 3 weeks of age.

Figure 7C:
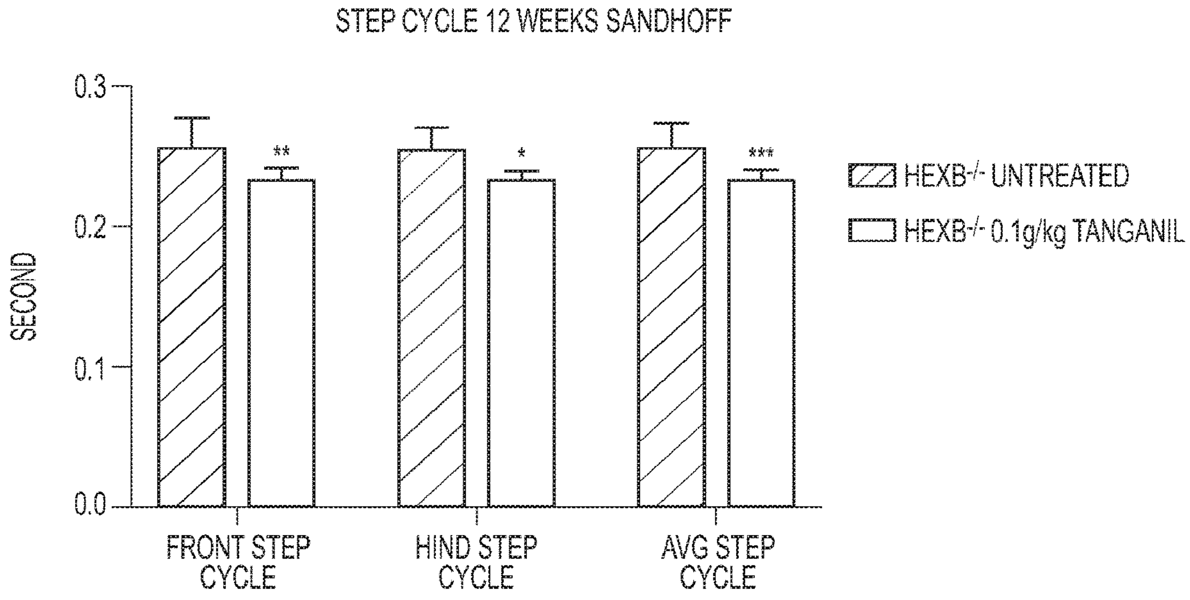
FIG. 7C shows the step cycle time for untreated and acetyl-leucine-treated Sandhoff mice assessed at 12 weeks of age.

Treatment of the Sandhoff mouse model with acetyl-leucine was associated with significantly faster front step cycle times ($p<0.05$ vs untreated SH mouse), significantly faster hind step cycle times ($p<0.01$ vs untreated SH mouse) and significantly faster average step cycle times ($p<0.001$ vs untreated SH mouse) (FIG. 7C). In FIG. 7 C, Acetyl-leucine treatment of 0.1 g/kg body weight was provided from 3 weeks of age. Front step cycle refers to the mouse's front limbs, hind step cycle to the mouse's rear limbs, and average step cycle takes into account all of the mouse's limbs. The asterisks (*//*) indicate p-values of <0.05/0.01/0.001 versus untreated Sandhoff mouse. Data shown is mean t Stdev.

Thus, acetyl-leucine treatment was associated with a faster step cycle in the Sandhoff mouse model, which may indicate improvement in motor function.

Conclusions

These studies demonstrate that acetyl-leucine treatment of a mouse model of Sandhoff disease may give rise to improvements in motor function as assessed by two independent experiments, as well as significantly increased lifespan.

Example 4

GM2 gangliosidoses are a group of lysosomal storage disorders arising from defects in β-hexosaminidase activity. The group encompasses Tay-Sachs disease, Sandhoff disease, and the AB variant of Tay-Sachs disease.

Fibroblasts derived from GM2 patients (Tay-Sachs disease, Sandhoff disease, and the AB variant of Tay-Sachs disease) and healthy controls were treated with acetyl-DL-leucine (1 mM for 6 days) prior to extraction and quantification of glycosphingolipid (GSL) levels via high performance liquid chromatography (HPLC).

Figure 8A:
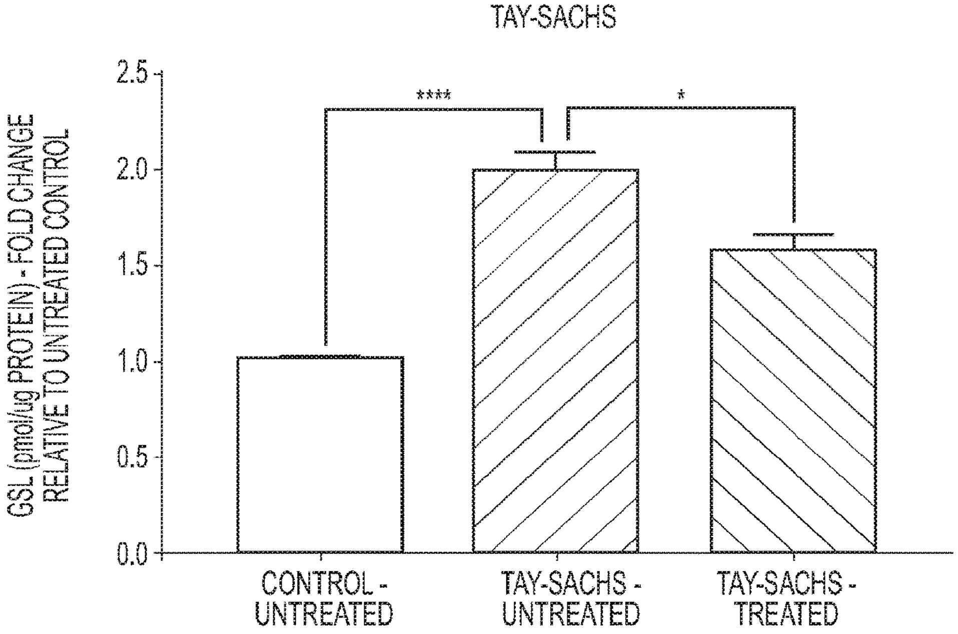
FIGS. 8A-8C show the effect of treatment with acetyl-DL-leucine on glycosphingolipid (GSL) levels in GM2 gangliosidoses patient fibroblasts (Tay-Sachs disease, Sandhoff disease, and AB variant of Tay-Sachs disease, respectively).
Figure 8B:
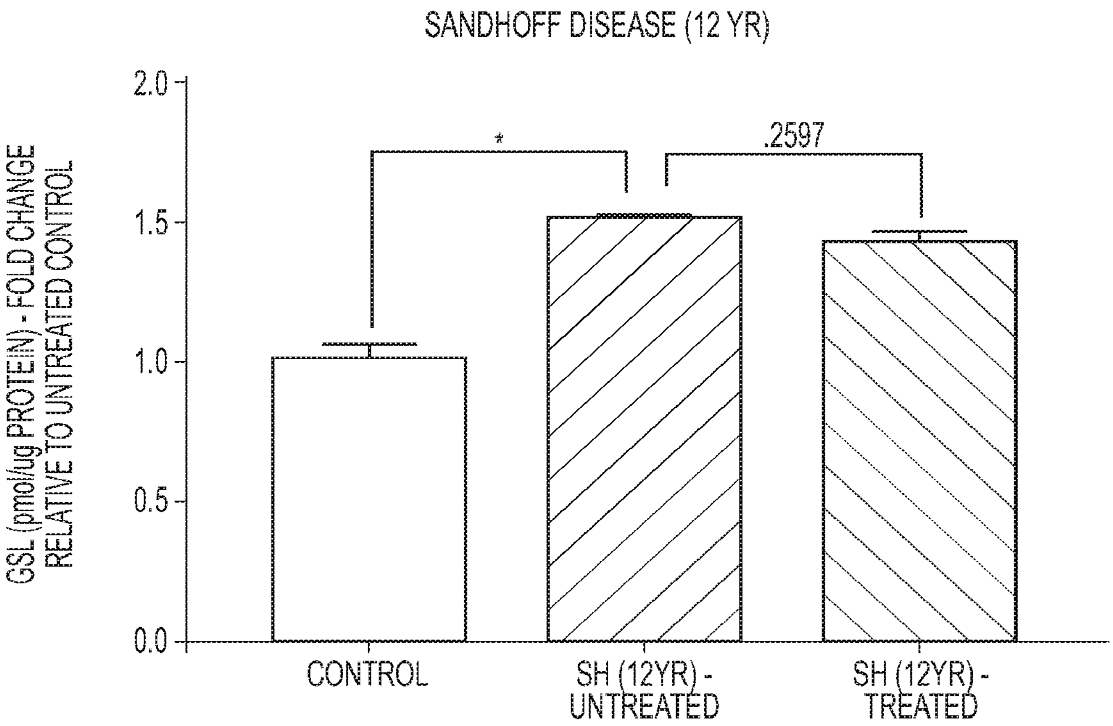
Figure 8C:
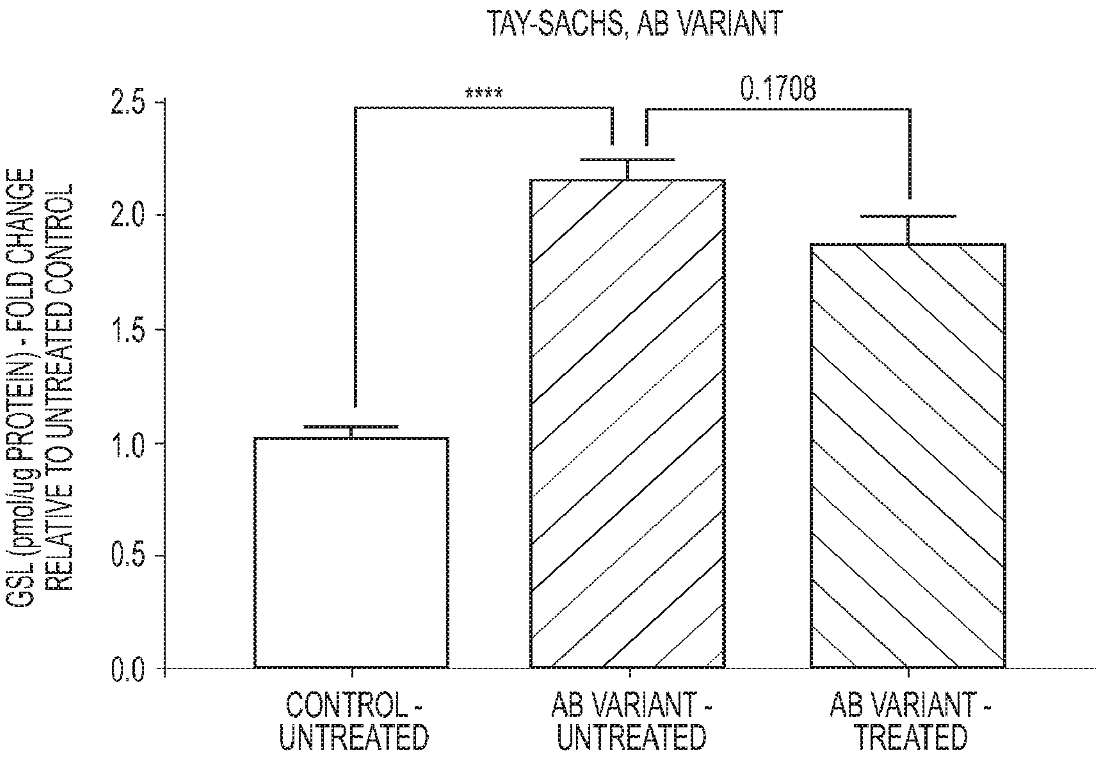

In the absence of treatment, fibroblasts derived from all 3 varieties of GM2 gangliosidosis demonstrated elevated GSL levels when compared to untreated wild-type controls. In all 3 cases, treatment with acetyl-DL-leucine (1 mM for 6 days) was associated with a reduction in GSL storage. In the case of Tay-Sachs disease, this decrease was statistically significant ($p<0.05$). In the case of Sandhoff disease and the AB variant of Tay-Sachs, there was a trend towards decreased GSL levels associated with treatment. Data presented in FIGS. 8A-8C show the results of the treatment for each cell line, respectively, with GSL levels adjusted for protein content and expressed as fold change relative to levels in untreated wild-type fibroblasts.

Example 5

Patient 1

The patient in this case study was a 28 year-old male who was genetically diagnosed with Tay-Sachs disease and who exhibited dysarthrophonia, tremor, ataxia of stance and gait, paraparesis and muscle atrophies. In particular, the patient was not able to stand or walk, could do single steps with strong support, and had distinct postural instability, ocular movement disorder, dysphagia and dysarthria, and mild cognitive function disorder. First symptoms were observed at the age of 16 years.

Before treatment was commenced, examination of the patient indicated a Scale for Assessment and Rating of Ataxia (SARA) score of 15.5/40. In addition, results from the patient's Spinocerebellar Ataxia Functional Index (SCAFI) analysis were:

Mean 8-meters Walking Test (8 MW): 21.6 s

MW 9-Hole Pegboard Test Dominant (9HPTD) (right): 48.3 s

MW 9-Hole Pegboard Test Non-Dominant (9HPTND): 44.9 s

MW PATA Word Test: 20

Montreal Cognitive Assessment (MoCA): 18/30

Video of the patient was also recorded for later comparison.

The day following this examination, the patient was started on therapy with acetyl-leucine, at a dose of 3 g per day for the first week, followed by a dose of 5 g per day for the second week onwards.

After one month and four months, respectively, the patient was re-examined while continuing treatment. After one month, the patient had improved fine motor skills and reduced hand tremor, for example while eating or drinking. Walking was not markedly changed. After four months, the patient was in stable condition with slightly improved cognitive function but had deterioration of stance, gait and fine motor function. The patient's SARA scores and results from the patient's SCAFI analyses are shown below compared to baseline.

TABLE 1

Patient Evaluation Parameters

| | Baseline | After one month with acetyl-DL-leucine | After 4 months with acetyl-DL-leucine |
|---|---|---|---|
| SARA | 15.5/40 | 15.5/40 | 17/40 |
| 8MWT | 21.6 sec | 7 sec | 25.49 sec |
| 9HPTD | 48.3 sec | 45.9 sec | 48.67 sec |
| 9HPTND | 44.9 sec | 40.1 sec | 47.09 sec |
| PATA | 20 | 22 | 21 |
| MoCA | 18/30 | 21/30 | 22/30 |

Overall, the patient exhibited an improvement in symptoms following acetyl-leucine treatment.

Patient 2

The patient in this case study was a 32 year-old female who was genetically diagnosed with Tay-Sachs disease and who exhibited ataxia of stance and gait, fine motor impairment, paraparesis of lower extremities, and muscle atrophies. In particular, walking was not possible without support, and the patient suffered from dysphagia and speech disorder, ocular movement disorder, and mild cognitive function disorder. First symptoms were observed at the age of 7 years.

Before treatment was commenced, examination of the patient indicated a Scale for Assessment and Rating of Ataxia (SARA) score of 10.5/40. In addition, results from the patient's Spinocerebellar Ataxia Functional Index (SCAFI) analysis were:

Mean 8-meters Walking Test (8 MW): 12.5 s

MW 9-Hole Pegboard Test Dominant (9HPTD) (right): 21.5 s

MW 9-Hole Pegboard Test Non-Dominant (9HPTND): 35.5 s

MW PATA Word Test: 18

Montreal Cognitive Assessment (MoCA): 21/30

Video of the patient was also recorded for later comparison.

The day of the examination, the patient was started on therapy with acetyl-leucine at a dose of 3 g per day for the first week, followed by a dose of 5 g per day for the second week onwards.

After one month, the patient was re-examined while continuing treatment and showed increased enunciation, improved postural stability, and enhanced cognitive function. Stance and gait were possible without support. The patient's SARA score and results from the patient's SCAFI analysis are shown below compared to baseline.

TABLE 2

Patient Evaluation Parameters

| | Baseline | After one month with acetyl-DL-leucine |
|---|---|---|
| SARA | 10.5/40 | 5/40 |
| 8MWT | 12.5 sec | 9.55 sec |
| 9HPTD | 21.5 sec | 34.97 sec |
| 9HPTND | 35.5 sec | 39.34 sec |
| PATA | 18 | 17 |
| MoCA | 21/30 | 25/30 |

Patient 3

The patient in this case study was an 8 year-old male who was genetically diagnosed with Tay-Sachs disease and who had epileptic cramps (tonic-clonic, about 10 seconds, self-limiting) almost every day before falling asleep, ocular movement disorder, anarthria, distinct problems in cognitive function and concentration (neurological examination was not possible), was not able to stand or walk by himself, and was very limited in daily activities (eating, washing or dressing himself was not possible). First symptoms were observed at the age of 9 months.

Before treatment was commenced, examination of the patient indicated a Scale for Assessment and Rating of Ataxia (SARA) score of 36/40, a mRDS score of 18/24, a EQ-5D-5L visual scale of 50, and a 8 MWT of 18.1 (only with strong support).

The patient was started on therapy with acetyl-leucine at a dose of 1.5 g per day for the first week, followed by a dose of 3 g per day for the second week onwards.

After one month, the patient was re-examined while continuing treatment and showed increased fine motor skills (was able to grab small things), increased motivation (tried more often to walk by himself), improved postural stability, gait and stance, and could speak single words. The patient's SARA, mRDS, EQ-5D-5L visual scale, and 8 MWT scores are shown below compared to baseline.

TABLE 3

Patient Evaluation Parameters

| | Baseline | After one month on acetyl-DL-leucine |
|---|---|---|
| SARA | 36/40 | 33/40 |
| mRDS | 18/24 | 16/24 |
| EQ-5D-5L visual scale | 50 | 60 |
| 8MWT | 18.1 (only with strong support) | 11.75 (with support of one arm) |

Example 6

The patient in this case study was a 13 year-old male who was genetically diagnosed with GM1 Gangliosidosis and who was not able to stand or walk by himself, was very limited in daily activities (eating, washing, dressing himself was not possible), and had ocular movement disorder, anarthria, and distinct problems in cognitive function and concentration (neurological examination was not possible). First symptoms were observed at the age of 2 years.

Before treatment was commenced, examination of the patient indicated a Scale for Assessment and Rating of Ataxia (SARA) score of 35/40, a mRDS score of 15, and a EQ-5D-5L visual scale of 50.

The patient was started on therapy with acetyl-leucine at a dose of 1.5 g per day for the first week, followed by a dose of 3 g per day for the second week onwards.

After one month, the patient was re-examined while continuing treatment and showed a stable general condition, increased gait (more fluent), and stable stance in natural position. The patient's SARA, mRDS, and EQ-5D-5L visual scale scores are shown below compared to baseline.

TABLE 4

Patient Evaluation Parameters

| | Baseline | After one month on acetyl-DL-leucine |
|---|---|---|
| SARA | 35/40 | 35/40 |
| mRDS | 15 | 16 |
| EQ-5D-5L visual scale | 50 | 60 |

Example 7

Patient 1

The patient in this case study was a 73 year-old male who had previously been diagnosed with amyotrophic lateral sclerosis (ALS).

The patient's symptomatology was characterised by progredient dysarthria (nasal and slurred speech) and weakness of the right dorsiflexor with consequent foot drop over the course of the previous three years.

Clinically, the patient showed bulbar speech, a 3/5 paresis of the right foot-dorsiflexors and big toe-lift, generalised exaggerated reflexes and spastic tone increase of the right lower limb. EMG showed spontaneous activity and cMRT did not show any pathology.

The patient was started on medication with Riluzol around the time of ALS diagnosis. However, the clinical symptomatology remained unchanged.

The patient was then started on therapy with acetyl-DL-leucine, at a dose of 3 gram per day for the first week, then a dose of 5 gram per day for the second week onwards. The results were documented by video.

After 15 days of treatment, a medical examination was conducted in which the patient reported significant improvement of speech. The patient was able to speak more fluently and was able to modulate his voice better compared to pre-medication (which was documented by video).

After a further 20 days, a further medical examination was conducted in which the patient reported further improvement of speech. In addition, the patient reported improvement of gait. The paresis of the right foot-dorsiflexors and consequently the foot drop had improved dramatically and were clinically hardly detectable. In addition, the patient reported an improvement in sleep: falling asleep much quicker, sleeping longer and feeling clearly more rested in the morning.

The patient continued on the treatment for approximately another 30 days. About 7 days after the patient stopped treatment, a medical examination was conducted in which the patient reported no further subjective improvement of either speech or paresis of the right dorsiflexor. Sleep had also deteriorated. After about 1-2 additional weeks off the acetyl-leucine treatment, the patient reported deterioration of speech. The patient resumed treatment at that time and, about two months later, reported stable symptomatology. Compared to the at the time when acetyl-leucine treatment was first initiated, a slight deterioration of speech could be observed.

As the patient had not observed any improvement of speech, the patient asked to stop the medication. Approximately 2-3 weeks later, the patient again reported deterioration of speech after discontinuation of acetyl-DL-leucine treatment. The patient resumed treatment and reported improved symptomatology, in particular speech.

Overall, the patient exhibited an improvement in symptoms following acetyl-leucine treatment.

Patient 2

The patient in this case study was a 74 old male who had been previously diagnosed with ALS.

The patient's symptomatology was characterised by progredient dysarthria (nasal and slurred speech) and concomitant dysphagia, and weakness while walking for over a year, and a paresis of the left upper limb for approximately four months. EMG had shown generalised polyphasic activity and chronic neurogenic impairment in the bulbar, cervical and lumbar segment.

Clinical examination of the patient showed severe dysarthria, hypomotility of the tongue, 2/5-3/5 paresis of the left arm with impairment of fine motor skills, generalised exaggerated reflexes and fasciculations. Medication with Riluzol had been started one month earlier.

The patient was started on treatment with acetyl-DL-leucine, at a dose of 3 g per day for the first week, then a dose of 5 g per day for the second week onwards.

After approximately 2 months, the patient was re-examined and he reported progredient deterioration of the motor function of the left hand, but a discrete improvement of walking. In addition, swallowing functions have remained stable.

Patient 3

The patient in this case study was a 66 year old male who had been previously diagnosed with ALS.

The patient's symptomatology was characterized by progredient weakness and atrophy of both proximal upper extremities, slight impairment of fine motor skills, and generalized fasciculations and cramps. EMG had shown pathologic spontaneous activity and chronic neurogenic change, MRT of the brain and cervical column did not show any pathology. Medication with Riluzol was started.

About two months later, a clinical examination showed a 3/5 to 4/5 paresis of both shoulders and proximal arms and a slowing of fine motor scills, generalized fasciculations, and normal reflexes. The patient was started on treatment with acetyl-DL-leucine, at a dose of 3 g per day for the first week, then a dose of 5 g per day for the second week onwards.

After one month, the patient did not report improvement of symptomatology, with no improvement of muscle force of upper limbs. Medication with acetyl-DL-leucine was suspended and the patient was asked to report worsening of symptomatology.

Patient 4

The patient in this case study was a 66 year old male who had been diagnosed with ALS. The patient's symptomatology was characterized by progressive weakness and atrophy of both proximal upper extremities, slight impairment of fine motor skills, and generalized fasciculations and cramps. EMG showed pathologic spontaneous activity and chronic neurogenic change. MRT of the brain and cervical column did not show any pathology. Treatment with riluzole was started.

A clinical examination showed a 3/5 to 4/5 paresis of both shoulders and proximal arms, a slowing of fine motor scills, generalized fasciculations, and normal reflexes, and an ALS-FRS score of 44/48.

The patient was started on treatment with acetyl-DL-leucine, at a dose of 3 g per day for the first week, then a dose of 5 g per day for the second week onwards.

After about one month, the patient reported subjective improvement of dysphagia and less hypersalivation. His relatives reported improved and more vital facial expression. Weakness of limbs was unchanged. Therapy was suspended and, 10 days later, the patient reported worsening of symptomatology, particularly subjective deterioration of dysphagia and hypersalivation. The patient resumed continuous treatment.

The patient was re-evaluated about 8 weeks later and symptomatology remained stable. The patient's ALS-FRS score was 43/48. Compared to symptomatology around the time of diagnosis, there was only a slight progression of weakness of gait and upper limbs.

Example 8

Acetyl-leucine treatment was demonstrated to give rise to improvements in 3 patients who had been diagnosed with multisystemic atrophy cerebellar type (MSA-C).

Patient 1

Patient 1 in this case study was a female in her late 50s who had shown progressive ataxia with speech problems and walking problems for the previous three years.

Clinical examination of the patient revealed central cerebellar ocular motor signs, moderate dysarthrophonia, mild limb ataxia, and moderate ataxia of stance and gait. Furthermore, a MRI of the patient showed atrophy of the cerebellum and the brainstem, in particular of the pons and mesencephalon. The patient was accordingly diagnosed as having MSA-C.

The patient was started on treatment with acetyl-DL-leucine, at a dose of 5 g per day (2 g upon waking, 1.5 g prior to lunch and 1.5 g prior to the evening meal).

After one week of treatment the patient already showed a significant improvement in speech.

Patient 2

The patient in this case study was a 77 year-old male who had been diagnosed with MSA-C.

The patient's symptomatology was characterised by progressive difficulties of walking and insecure gait with a tendency to fall (the patient fell approximately 10 times a month). The patient exhibited dizziness, hypokinetic-rigid syndrome, saccadic eye movements, dysmetria in the coordination test, and autonomic dysfunction, for example erectile dysfunction, orthostatic hypotension and incomplete bladder emptying over the course of the last four years.

Before treatment was commenced, the patient's symptoms remained unchanged over at least a three-month period.

The patient was started on treatment with acetyl-DL-leucine at a dose of 3 gram per day for the first week, followed by a dose of up to 5 gram per day.

After 3 weeks of treatment, a further examination was carried out. The patient and his wife reported significant improvement of gait: the patient walks more securely and the falls completely stopped. In addition, dizziness experienced by the patient substantially improved.

The patient was instructed to stop the medication and after one week the patient reported a deterioration of gait and dizziness. The patient reported feeling more insecure walking, with a strong tendency to fall.

The patient was then instructed to restart the medication, which he continued for a further 40 days and then again stopped. During clinical examination 7 days after stopping the medication, the patient confirmed progressive deterioration of gait and dizziness two days after stopping the treatment, and a very strong tendency to fall 5 days after stopping the treatment. The patient subsequently returned to continuous treatment.

Patient 3

The patient in this case study was a 76 year-old male who had been diagnosed with oligosymptomatic MSA-C.

The patient's symptomatology was characterised by progressive difficulties in walking and insecure gait (without falls), as well as dizziness.

Clinically, the patient showed saccadic eye movement and dysmetria in the coordination tests. cMRI showed an atrophy of the mesencephalon, and FDG-PET of the brain showed a reduced metabolism of the striatum and cerebellum. The patient's posturography test results were pathological with a high tendency to fall.

Before treatment was commenced, the patient's clinical symptomatology remained unchanged over at least a one-year period.

Gait analysis was performed, which showed atactic gait, and reduced speed and increased track width compared to the normal range, and fluctuations of gait. The patient was then started on treatment with acetyl-DL-leucine at a dose of 3 gram per day for the first week, followed by a dose of 5 gram per day for the second week onwards.

After one month of treatment, a further examination was carried out. Gait analysis showed an improvement of gait speed, and reductions of track width and gait fluctuations.

TABLE 5

Gait analysis parameters.

| | Shortly after commencing treatment | After 27 days of treatment | Normal range (±SD) |
|---|---|---|---|
| Speed (cm/sec) | 72 | 106 | 110.81 (18.33) |
| Max. speed (cm/sec) | 183 | 208 | 158.30 (22.66) |
| Cadence (steps/minute) | 101 | 113 | 109.19 (12.75) |
| Track width (cm) | 16.8 | 14.6 | 9.06 (1.94) |
| Step cycle length (cm) | 87 | 113 | 121.81 (11.52) |
| Double stance (%) | 32.5 | 27.3 | 20.73 (2.55) |
| Coefficient of variation (temporal) | 3.3 | 3.1 | 1.94 (0.85) |
| Functional Gait Assessment | 21/30 | 20/30 | 24.9 (3.6) |

The patient was instructed to stop the medication and he reported progressive deterioration of gait and dizziness approximately two to three weeks after stopping the medication.

The patient subsequently returned to continuous treatment and symptomatology re-improved. Treatment was again suspended and the patient was evaluated three weeks later. The patient reported deterioration of symptoms, especially dizziness. Gait analysis showed an increased gait width comparable to pre-therapy status:

TABLE 6

Gait analysis parameters.

| | After 20 days of re-suspending treatment |
|---|---|
| Speed (cm/sec) | 106 |
| Max. speed (cm/sec) | 197 |
| Cadence (steps/minute) | 112 |
| Track width (cm) | 17.5 |
| Step cycle length (cm) | 115 |
| Double stance (%) | 27.1 |
| Coefficient of variation (temporal) | 2.5 |
| Functional Gait Assessment | 22/30 |

Example 9

The patient in this case study was a 59 year-old male with progredient personality change characterised by apathy, lethargy and indifference. In addition, the patient showed a mainly left-side hypokinetic-rigid syndrome with impairment of fine motor skills and reduced resonation of left arm. Furthermore, the patient showed generalised bradykinesia and gait disorder with small steps and 2-3 falls per month. The patient also shows slurred speech and cognitive deficits concerning psychomotoric slowing and reduced semantic word fluency.

The patient was diagnosed with frontotemporal dementia with parkinsonism and Datscan revealed a reduction of dopamine receptors supporting the diagnosis. FDG-PET of the brain showed a mainly frontal reduced metabolism.

The patient exhibited little improvement during treatment with L-Dopa and Ropinirol.

The patient was started on treatment with acetyl-DL-leucine, at a dose of 3 gram per day for one week, then a dose of 5 gram per day for 4 weeks.

After approximately one month of acetyl-leucine treatment, medication was stopped and the patient was re-examined 13 days later.

The patient and his wife and daughter reported a significant improvement of gait under therapy with acetyl-leucine and in addition the patient's falls stopped. The patient also exhibited an improvement of speech, which was less slurred, more comprehensible and subjectively much more controlled. After suspension of treatment the symptoms worsened.

Example 10

The patient in this case study was a 75 year-old male with progressive insecure gait disorder and dizziness leading to backward falls. In addition, the patient presented a mainly left-sided hypokinetic-rigid syndrome with apraxia and alien-limb phenomenon.

The patient was diagnosed with corticobasal syndrome. A Datscan revealed a reduction of dopamine-receptors and an MRI showed an atrophic motorcortex of the right hemisphere supporting the diagnosis.

The patient exhibited no improvement during treatment with L-Dopa.

The patient was started on treatment with acetyl-DL-leucine, at a dose of 3 g per day for the first week, then 5 g per day. Gait analysis was performed before treatment commenced.

After 20 days of acetyl-leucine treatment, the patient was re-examined. An improvement of dizziness symptoms and significant reduction in the frequency of falls was noted.

TABLE 7

Gait analysis parameters.

| | Before treatment | After 20 days of treatment | Mean (±SD) |
|---|---|---|---|
| Speed (cm/sec) | 63 | 92 | 110.81 (18.33) |
| Max. speed (cm/sec) | 131 | 152 | 158.30 (22.66) |
| Cadence (steps/minute) | 90 | 106 | 109.19 (12.75) |
| Track width (cm) | 12.1 | 12.3 | 9.06 (1.94) |
| Step cycle length (cm) | 84 | 104 | 121.81 (11.52) |
| Double stance (%) | 29.8 | 26.6 | 20.73 (2.55) |
| Coefficient of variation (temporal) | 3.9 | 3.4 | 1.94 (0.85) |
| Functional Gait Assessment | 13/30 | 18/30 | 24.9 (3.6) |

There was an objective improvement in gait analysis parameters, for example in speed, maximal speed, cadence and reduced double stance (Table 2 and FIG. 9).

After 8 weeks of acetyl-leucine treatment, medication was stopped and the patient was re-examined 6 days later.

The patient reported an increase of dizziness symptoms two days after suspension of treatment (the sensation of being drunk).

The patient subsequently returned to continuous treatment.

Example 11

Patient 1

The patient in this case study was a 76 year-old female with dizziness, which mainly occurred while walking. No falls were reported. The patient also exhibited gait disorder with small steps and generalised bradykinesia and vertical gaze palsy with impairment of fine motor skills.

The patient was diagnosed with progressive supranuclear palsy. Datscan revealed a reduction of dopamine-receptors and FDG-PET of the brain showed a mainly frontal reduced metabolism, supporting the diagnosis.

The patient exhibited little improvement during treatment with L-Dopa.

The patient was started on treatment with acetyl-DL-leucine, at a dose of 3 g per day for one week, then a dose of 5 g per day for 4 weeks. After 27 days of acetyl-leucine treatment, medication was stopped and the patient was re-examined 60 days later.

The patient reported a significant reduction of dizziness and slight improvement of gait under therapy with acetyl-leucine. After suspension of treatment, the symptoms worsened.

The patient was re-examined about two months later and reported a stable symptomatology of underlying progressive supranuclear palsy; there was no clinical progression. The PSPRS Score remained stable, and the reduction of dizziness was still significant.

Patient 2

The patient in this case study was a 66 year-old female with symmetric hypokinetic-rigid syndrome, gait disorder with insecure and small steps (strong tendency to fall) and vertical gaze palsy with impairment of fine motor skills. The patient was diagnosed with progressive supranuclear palsy. Datscan revealed a reduction of dopamine-receptors and FDG-PET of the brain showed a mainly frontal reduced metabolism, supporting the diagnosis. There was no levodopa response.

The patient was started on treatment with acetyl-DL-leucine, at a dose of 3 g per day for the first week, then 5 g per day. Gait analysis was performed before treatment commenced. After 17 days of treatment, medication was stopped and the patient was re-examined 4 days later. The patient reported no significant improvement of gait or hypokinetic rigid syndrome.

TABLE 8

Gait analysis parameters.

| — | Before treatment | After 17 days of treatment | Normal values (±SD) |
|---|---|---|---|
| speed (cm/sec) | 51 | 68 | 119.12 (17.27) |
| Max. speed (cm/sec) | 123 | 98 | 176.78 (19.10) |
| cadence (steps/minute) | 93 | 99 | 113.06 (10.38) |
| Track width (cm) | 10.3 | 9.3 | 9.49 (3.56) |
| Step cycle length (cm) | 66 | 82 | 126.71 (13.06) |
| Double stance (%) | 34.5 | 28.6 | 20.35 (3.21) |
| Coefficient of variation (temporal) | 8.5 | 6.6 | 1.76 (0.73) |
| Functional Gait Assessment | 15/30 | 15/30 | 27.1 (2.3) |

The patient was reevaluated about two months later and reported no deterioration of symptoms after stopping medication.

Patient 3

The patient in this case study was a 56 year-old male with symmetric hypokinetic-rigid syndrome, insecure and history of falls and vertical gaze palsy with impairment of fine motor skills. The patient was diagnosed with progressive supranuclear palsy. Datscan revealed a reduction of dopamine-receptors and FDG-PET of the brain showed a frontomesial and parietotemporal reduced metabolism, supporting the diagnosis. There was no levodopa response.

The patient was started on treatment with acetyl-DL-leucine, at a dose of 3 g per day for the first week, then 5 g per day. Gait analysis was performed before treatment commenced. After 17 days of treatment, medication was stopped and the patient was re-examined 4 days later. The patient reported no significant improvement of gait or hypokinetic rigid syndrome.

TABLE 9

| Gait analysis parameters. | | | |
|---|---|---|---|
| — | Before treatment | After 17 days of treatment | Normal values (±SD) |
| speed (cm/ sec) | 103 | 120 | 125.34 (20.66) |
| Max. speed (cm/sec) | 163 | 194 | 180.07 (26.57) |
| cadence (steps/minute) | 106 | 112 | 115.27 (12.02) |
| Track width (cm) | 15.5 | 15.1 | 9.12 (2.97) |
| Step cycle length (cm) | 118 | 129 | 130.34 (13.01) |
| Double stance (%) | 25.8 | 24.3 | 19.65 (2.75) |
| Coefficient of variation (temporal) | 3.6 | 3.1 | 1.77 (1.04) |
| Functional Gait Assessment | 28/30 | 27/30 | 28.4 (1.6) |

The patient was reevaluated about two months later and reported no deterioration of symptoms after stopping medication.

Patient 4

The patient in this case study was a 76 year-old male with progredient gait disorder, insecure and small steps (strong tendency to fall), camptocormia, slow and hypometric saccades, blepharospasmus and impairment of fine motor skills. The patient was diagnosed with progressive supranuclear palsy. MRI showed discreet atrophy of the mid brain (Mickey Mouse sign). There was a slight levodopa response.

The patient was started on treatment with acetyl-DL-leucine, at a dose of 3 g per day for the first week, then 5 g per day. Gait analysis was performed before treatment commenced. After three weeks of treatment, medication was stopped and the patient was re-examined. The patient reported gait with increased subjective security and with reduced frequency of falls. Gait analysis showed improvement of gait with increased speed, max. speed, and step cycle length and reduction of track width, double stance and coefficient of variation.

TABLE 10

| Gait analysis parameters. | | | |
|---|---|---|---|
| | Before treatment | After 3 weeks of treatment | Normal values (±SD) |
| speed (cm/sec) | 39 | 65 | 110.81 (18.33) |
| Max. speed (cm/sec) | 70 | 93 | 158.30 (22.66) |
| cadence (steps/minute) | 109 | 125 | 109.19 (12.75) |
| Track width (cm) | 15.4 | 13.6 | 9.06 (1.94) |
| Step cycle length (cm) | 43 | 63 | 121.81 (11.52) |
| Double stance (%) | 45.4 | 36 | 20.73 (2.55) |
| Coefficient of variation (temporal) | 8.2 | 6.8 | 1.94 (0.85) |
| Functional Gait Assessment | | 14/30 | 24.9 (3.6) |

After three months without medication, the patient reported a progression of hypokinetic-rigid syndrome. Gait worsened, with more frequent falls.

Example 12

Patient 1

The patient in this case study was a 42 year-old male engineer who had suffered from dizziness and postural imbalance for almost one year.

The patient was diagnosed with downbeat nystagmus: the patient was severely impaired by blurred vision (oscillopsia) due to the nystagmus, and experienced difficulties while reading and writing. The patient's visual acuity was: right 0.75, left 0.67, binocular 0.83, and the downbeat nystagmus was documented by video-oculography. The patient also exhibited increased body sway, which was documented by posturography.

Treatment with 4-aminopyridine (Fampyra, 10 mg twice daily) for four weeks did not give rise to any benefit.

The patient was started on treatment with acetyl-DL-leucine, at a dose of 3 g per day (1 g upon waking, 1 g prior to lunch and 1 g prior to the evening meal) for one week, then a dose of 5 gram per day (2 g upon waking, 1.5 g prior to lunch and 1.5 g prior to the evening meal).

After 10 days, the patient reported significant benefit and that the effect developed slowly. The patient continued with this treatment dosage, and no side-effects resulted. A temporary suspension of the medication led to a considerable deterioration.

The patient was re-examined approximately 14 weeks after starting acetyl-leucine treatment, during which the patient reported to be very happy with the benefit. The patient's reading and writing were much better, because of reduced oscillopsia: the image of the visual surrounding was stable. The patient was able to suppress the nystagmus by visual fixation. In addition, the patient's spatial orientation was improved.

Clinical examination by two independent examiners revealed a reduction of the nystagmus and video-oculography showed that the patient could suppress the nystagmus by visual fixation. The patient's visual acuity was: right 0.83, left 1.0, binocular 1.

Posturography demonstrated a reduction of postural sway.

Overall, this case study demonstrates improvement in the patient's symptoms for this indication.

Patient 2

The patient in this case study was diagnosed with downbeat nystagmus. The patient showed postural imbalance and dizziness. The patient did not benefit from Fampyra®.

Figure 13A:
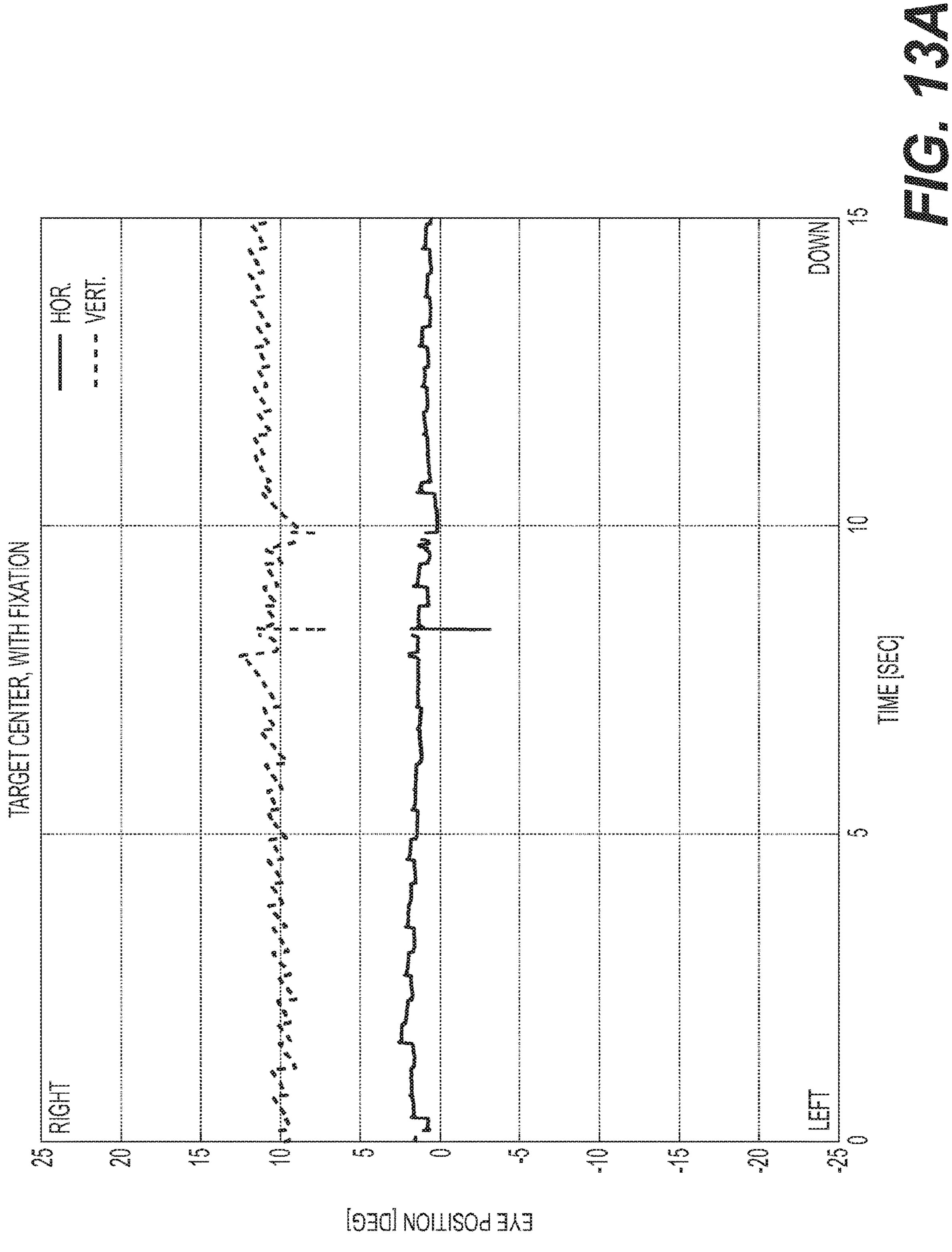
FIGS. 13A-13C show that after treatment with acetyl-DL-leucine, a patient who had been diagnosed with down-beat nystagmus syndrome could partially suppress the nystagmus by visual fixation.
Figure 13B:
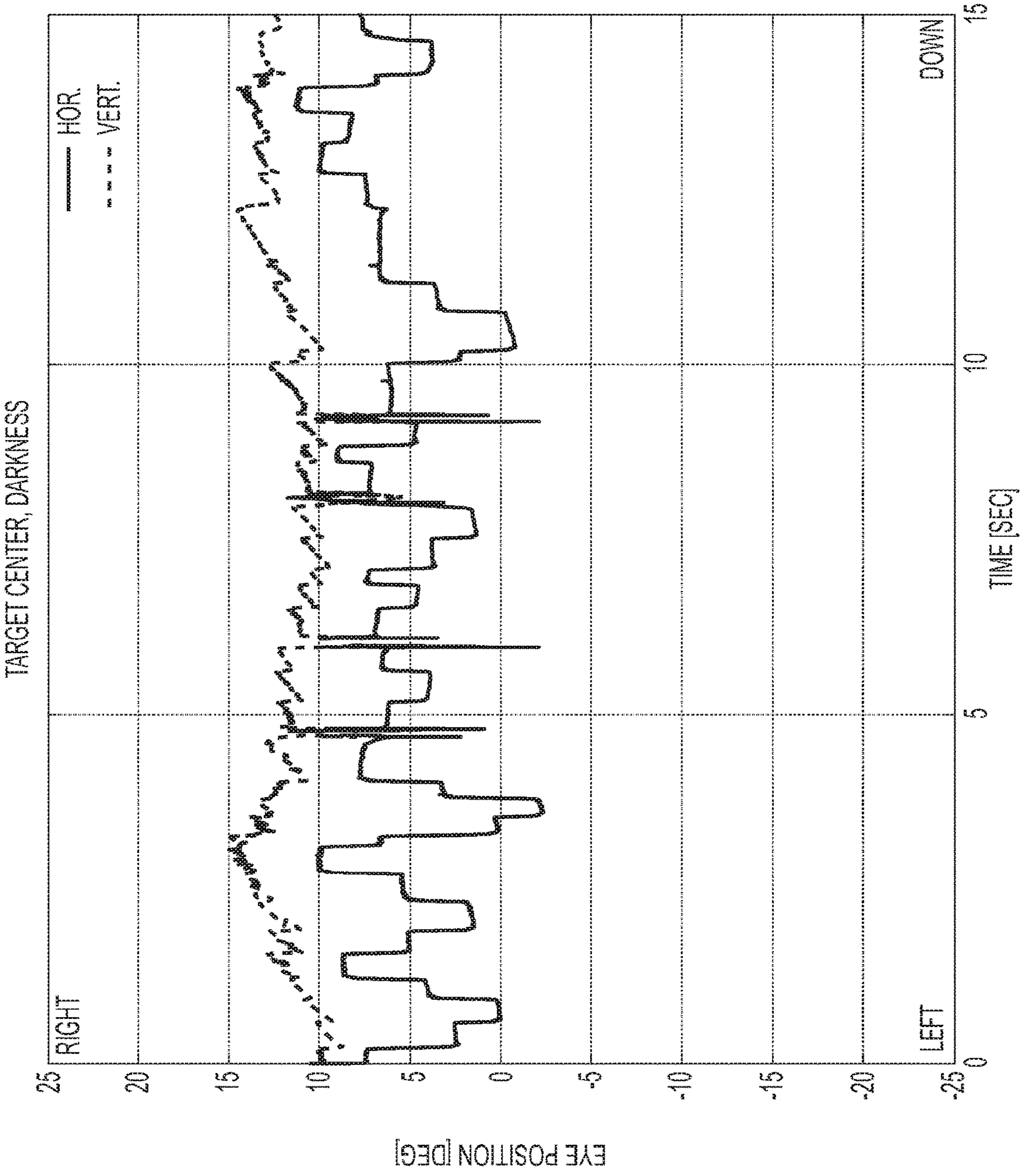
Figure 13C:
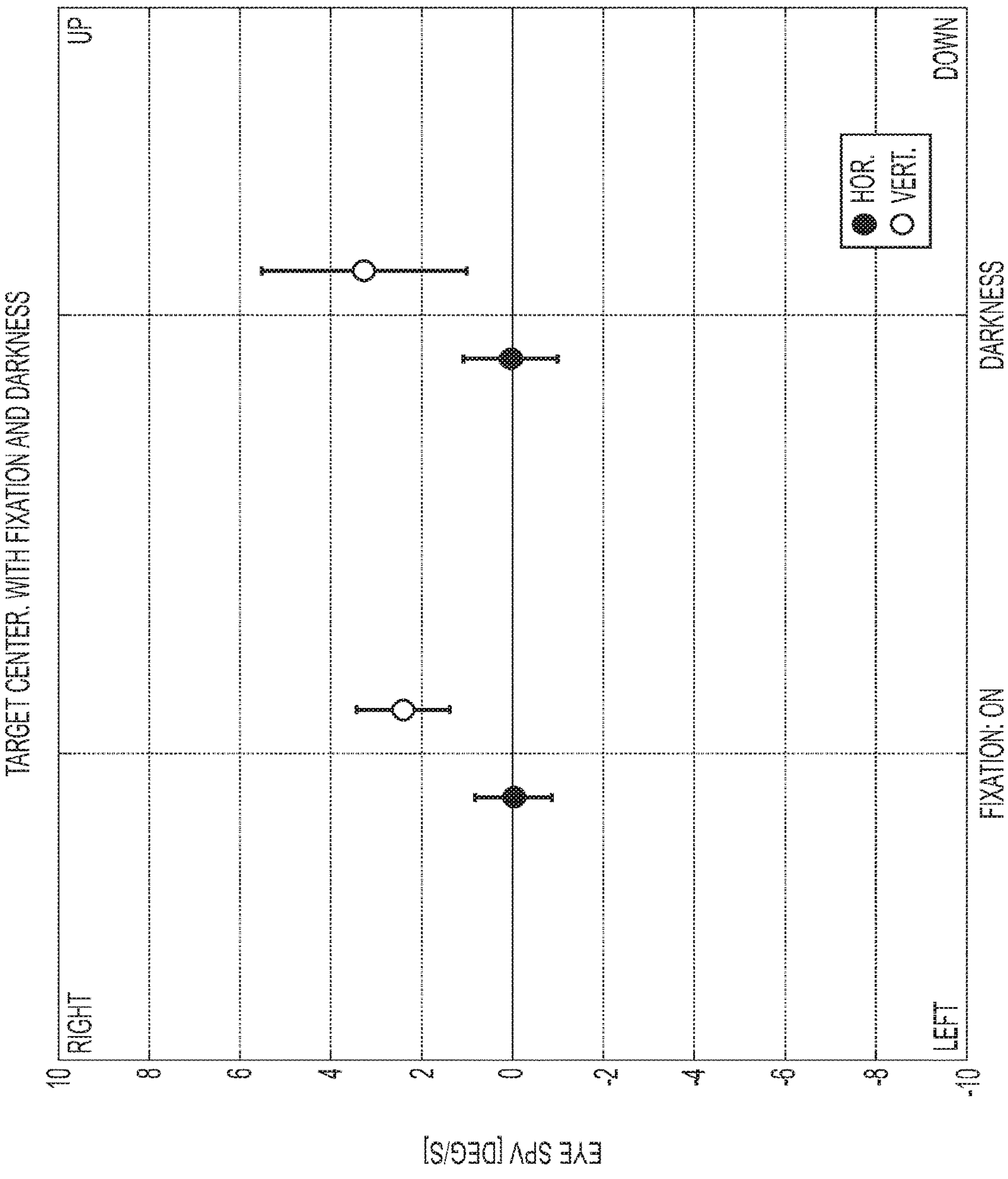

The patient began taking acetyl-DL-leucine (3 g/day for the first week; 5 g/day thereafter) and subsequently showed improvement of gait, with the ability to walk much longer distances (one hour), and improved alertness. The patient's downbeat nystagmus also improved (documented by video-oculography). The patient could partially suppress the nystagmus by visual fixation, as evaluated using a target center (dot presented in the center of a display for 30 seconds, FIG. 13A) and in complete darkness using goggles covered with special glasses for 45 seconds (FIG. 13B). The results (median of slow phase velocity, SPV) were as follows: Target Center-horizontal: −0.02°/s, vertical: 2.41°/s; Complete Darkness-horizontal: 0.05°/s, vertical: 3.27°/s (FIG. 13C). The patient was able to minimize eye movements while fixating, as shown in FIG. 13A.

Gait analysis showed an increase of self-chosen velocity from 56 to 85 cm/sec and maximal gait velocity from 122 to 155 cm/sec. Medication was then suspended. About one month after stopping acetyl-DL-leucine treatment, the patient's symptomatology worsened. Gait analysis showed a decrease of self-chosen velocity from 85 to 72 cm/sec and maximal gait velocity from 155 to 113 cm/sec.

Example 13

Patient 1

The patient in this case study was a 70 year-old female with mainly right sided hypokinetic-rigid syndrome and tremor, antecollis, frequent falls, orthostatic dysfunction and urge incontinence.

The patient was diagnosed with with multiple system atrophy Parkinson type (MSA-P). Datscan revealed a mainly left sided reduction of dopamine-receptors and FDG-PET of the brain showed a mainly parieto-occipital reduced metabolism. There was a discreet Levodopa response (100/25 mg 3×daily).

The patient began taking acetyl-DL-leucine (3 g/day for the first week; 5 g/day thereafter). After 3 weeks on acetyl-DL-leucine, the patient was evaluated and reported no significant improvement of gait, reduction of falls or improved hypokinetic rigid-syndrome. Medication was stopped.

6 weeks later the patient did not report deterioration of symptoms after stopping medication.

Patient 2

The patient in this case study was a 78 year-old male diagnosed with multiple system atrophy Parkinson type (MSA-P). The patient's symptomatology was characterized by a progressive hypokinetic-rigid syndrome, orthostatic dysfunction and consecutive dizziness and balance disorder. The patient showed saccadic eye movement and symmetric rigor of both upper limbs. Balancing on an imaginary tightrope was associated with insecureness and loss of balance. FDG-PET of the brain showed a reduced metabolism of both parietal and occipital cortex, suggestive for Lewy-Body-Dementia.

The patient was started on treatment with acetyl-DL-leucine, at a dose of 3 g per day for the first week, then 5 g per day. The patient was examined before initiation of treatment and showed the clinical symptomatology described above, with very pronounced insecure gait and dizziness.

After one month of treatment, medication was stopped and the patient was evaluated. The patient reported subjective improvement of dizziness and clinical examination showed improved balancing on an imaginary tightrope, which the patient performed without any difficulties compared to the prior examination. Gait analysis was performed.

After one month without medication, the patient reported stable symptomatology. No worsening of dizziness or insecurity of gait was reported. Gait analysis was performed.

After two months without medication, a gait analysis was performed and showed reduction of velocity of gait, reduction of step length and worsening of FGA-Score. The patient reported a worsening of general symptomatology, including progressive weakness of legs and increased insecureness of gait.

TABLE 11

Gait analysis parameters.

| | After 1 month of treatment | After 1 month without treatment | After 2 months without treatment | Normal values (±SD) |
|---|---|---|---|---|
| speed (cm/sec) | 109 | 114 | 94 | 110.81 (18.33) |
| Max. speed (cm/sec) | 214 | 196 | 177 | 158.30 (22.66) |
| cadence (steps/minute) | 109 | 109 | 106 | 109.19 (12.75) |
| Track width (cm) | 3.8 | 2.3 | 3.4 | 9.06 (1.94) |
| Step cycle length (cm) | 120 | 126 | 107 | 121.81 (11.52) |
| Double stance (%) | 25.6 | 22.5 | 26.7 | 20.73 (2.55) |
| Coefficient of variation (temporal) | 2.7 | 1.7 | 2.1 | 1.94 (0.85) |
| Functional Gait Assessment | 24/30 | 25/30 | 22/30 | 24.9 (3.6) |

Patient 3

The patient in this case study was a 78 year-old male diagnosed with multiple system atrophy Parkinson type (MSA-P). The patient's symptomatology was characterized by progressive hypokinetic-rigid syndrome, urinary incontinence, incipient cognitive dysfunction, and gait disorder with small steps and 2-3 falls per month. Cognitive deficits were characterized by psychomotoric slowing and intermittent mental confusion. Datscan revealed a reduction of dopamine-receptors, which supported the diagnosis. FDG-PET of the brain showed a mainly striatal reduced metabolism. Levodopa therapy was suspended due to side effects.

The patient was started on treatment with acetyl-DL-leucine, at a dose of 3 g per day for the first week, then 5 g per day. The patient evaluated after one month on acetyl-DL-leucine. The patient's wife reported a significant improvement of cognitive function. Episodes of mental confusion completely disappeared. The patient's cognitive structure seemed much clearer and straighter. There was no improvement of gait function. The patient's wife supported continuing the medication.

Example 14

The patient in this case study was a 45-year-old male diagnosed with spinocerebellar ataxia 28 (SCA 28). Genetic testing showed a known pathogenic variant in AFG3L2. The patient's symptomatology was characterized by progressive cerebellar syndrome since the age of 30, characterized by slurred speech, unstable gait, balance disorder and dizziness. The patient's father and grandmother suffered from a similar symptomatology. The patient showed saccadic eye movements and dysmetria in the coordination tests, ataxic gait, slurred speech, exaggerated reflexes of the lower limbs, spasticity of the lower limbs and a positive Babinski sign on the left. cMRI showed a marked atrophy of the cerebellum.

The patient was started on treatment with acetyl-DL-leucine at a dose of 5 g per day. A gait analysis was performed before treatment commenced. After about one month of treatment, medication was stopped and the patient was evaluated. The patient reported an improvement of the symptomatology, in particular reduced dizziness (almost vanished), and a more stable gait. The patient reported that he no longer walked like a robot and could climb the stairs without using the banisters. A gait analysis was performed, which showed an improvement of parameters.

TABLE 12

| Gait analysis parameters. | | | |
|---|---|---|---|
| | Before treatment | After treatment for one month | Standard values (±SD) |
| Self-chosen speed (cm/sec) | 101 | 118 | 126.61 (21.43) |
| Maximum speed (cm/sec) | 188 | 201 | 182.94 (25.37) |
| Cadence (steps/minute) | 100 | 105 | 115.52 (9.36) |
| Track width (cm) | 14.5 | 11.7 | 9.43 (2.27) |
| Step cycle length (cm) | 122 | 135 | 131.55 (17.98) |
| Double stance (%) | 24.9 | 23.8 | 18.76 (3.46) |
| Coefficient of variation (temporal) | 4.1 | 2.1 | 1.88 (0.79) |
| Functional Gait Assessment | 24/30 | 23/30 | 28.9 (1.5) |

Example 15

Patients 1 & 2

The patients in this case study were 2 female siblings, 24 (Patient 1) and 19 (Patient 2) years old, respectively. The patients suffer from ataxia telangiectasia.

Patient 1 showed delayed developmental milestones. The patient did not walk until 2 years of age and had progression of cerebellar ataxia signs and symptoms, seizures, together with generalized, distal pronounced hypertonia and telangiectasias on the eyes, ears, and chest. Diagnosis was established at the age of 9 years. Patient 1's ocular motor function showed downbeat-nystagmus with gaze straight-ahead and in the gaze to the left greater than right, gaze-holding nystagmus upward, vertical and horizontal saccadic smooth pursuit, and hypometric saccades horizontally and vertically, with restricted motility upward.

Before treatment was commenced, examination of Patient 1 indicated a Scale for Assessment and Rating of Ataxia (SARA) score of 22/40. Results from the patient's Spinocerebellar Ataxia Functional Index (SCAFI) analysis were:

Mean 8-meters Walking Test (8 MW): 21.8 s

MW 9-Hole Pegboard Test Dominant (9HPTD) (right): 90.2 s

MW 9-Hole Pegboard Test Non-Dominant (9HPTND): 125.8 s

MW PATA Word Test: 12.5

Visual analog scale (as evaluated by the patient): 99

Results from video-oculography were:

TABLE 13

| Video-oculography parameters. | | |
|---|---|---|
| Slow phase velocity of the gaze-holding nystagmus | Horizontal | Vertical |
| Centrum | 0.54 | 6.9 |
| Vpravo | −1.16 | 6.2 |
| Vl'avo | 12.2 | 12.6 |
| Nadol | −0.14 | 6.9 |
| Nahor | −0.39 | 5.95 |

Patient 1 began treatment with acetyl-DL-leucine (5 g/day) following examination. After one month of treatment, the patient was re-evaluated. Caregivers reported an improvement of speech and gait. The patient herself did not perceive any change. Examination indicated a Scale for Assessment and Rating of Ataxia (SARA) score of 15.5/40. Results from the patient's Spinocerebellar Ataxia Functional Index (SCAFI) analysis were:

Mean 8-meters Walking Test (8 MW): 18.5 s

MW 9-Hole Pegboard Test Dominant (9HPTD) (right): 77.9 s

MW 9-Hole Pegboard Test Non-Dominant (9HPTND): 101.3 s

MW PATA Word Test: 13

Visual analog scale (as evaluated by the patient): 85

Results from video-oculography were:

TABLE 14

| Video-oculography parameters. | | |
|---|---|---|
| Slow phase velocity of the gaze-holding nystagmus | Horizontal | Vertical |
| Center | 0.4 | 4.77 |
| Right | −0.95 | 4.83 |
| Left | 8.2 | 8.85 |
| Down | −0.44 | 5.29 |
| Up | 0.72 | 2.67 |

Patient 1's SARA and SCAFI subsets improved after treatment, and video-oculography showed significant improvement of fixation stability and decrease of intensity of downbeat-nystagmus.

Patient 2 showed delayed developmental milestones, seizure at the age of 1, generalized hypotonia, contractures of low extremities with pes equinovarus bilaterally, areflexia, acute lymphoblastic leukemia at the age of 3 years, slightly enlarged spleen, hypercholesterolemia, hypochromatic microcytic anemia, pigmental naevi, and vitiligo. First symptoms were noticed by the patient's parents at the age of 15 months. Patient 2's ocular motor function showed square wave jerks, gaze-holding nystagmus left greater than right with vertical component, downbeat-nystagmus, saccadic smooth pursuit, vertical gaze palsy upward greater than downward, and impaired convergence.

Before treatment was commenced, examination of Patient 2 indicated a Scale for Assessment and Rating of Ataxia (SARA) score of 28.5/40. Results from the patient's Spinocerebellar Ataxia Functional Index (SCAFI) analysis were:

Mean 8-meters Walking Test (8 MW): not able to perform without support

MW 9-Hole Pegboard Test Dominant (9HPTD) (right): 300 s

MW 9-Hole Pegboard Test Non-Dominant (9HPTND): 299.2 s

MW PATA Word Test: 13.5

Visual analog scale (as evaluated by the patient): 45

Results from video-oculography were:

TABLE 15

| Video-oculography parameters. | | |
|---|---|---|
| Slow phase velocity of the gaze-holding nystagmus | Horizontal | Vertical |
| Center | −2 | 6.18 |
| Right | −3.97 | 7.6 |
| Left | −0.24 | 9.49 |
| Down | −2.86 | 5.58 |
| Up | −1.11 | 4.97 |

Patient 2 began treatment with acetyl-DL-leucine (5 g/day) following examination. After one month of treatment, the patient was re-evaluated. Caregivers reported an improvement of fine motor function, hand tremor, and speech. The patient herself did not perceive any benefit. Examination indicated a Scale for Assessment and Rating of Ataxia (SARA) score of 23.5/40. Results from the patient's Spinocerebellar Ataxia Functional Index (SCAFI) analysis were:

Mean 8-meters Walking Test (8 MW): not able to perform without support

MW 9-Hole Pegboard Test Dominant (9HPTD) (right): 300 s

MW 9-Hole Pegboard Test Non-Dominant (9HPTND): 300 s

MW PATA Word Test: 14

Visual analog scale (as evaluated by the patient): 80

Results from video-oculography were:

TABLE 16

| Video-oculography parameters. | | |
|---|---|---|
| Slow phase velocity of the gaze-holding nystagmus | Horizontal | Vertical |
| Center | −1.45 | 5.6 |
| Right | −3.45 | 6.56 |
| Left | 3.58 | 7 |
| Down | −2.5 | 4.69 |
| Up | −0.51 | 3.15 |

Video-oculography showed improvement of fixation stability and significant improvement of downbeat-nystagmus intensity in Patient 2.

Patient 3

The patient in this case study was a 19 year old female suffering from ataxia telangiectasia from early childhood, having:

Delayed motor development, cerebellar ataxia signs and symptoms, pronounced axial hypotonia with acral hypertonia, severe contractures of feet with orthopedic deformities pes equinus et transversoplanus bilaterally and was thus confined to wheelchair, dysdiadochokinesis, and areflexia of low extremities with decreased proprioceptive perception; and Non-Hodgkin lymphoma, polymorphism MTHFR (C677T), lymphangioma of the lower lip, cholecystolithiasis, dilated cardiomyopathy, pigmental naevi, thoraco-lumbar kyphoscoliosis, and scleral teleangiectasias on both eyes.

The patient's ocular motor function showed gaze-holding nystagmus to the right and to the left, saccadic eye movements, slow saccades to all directions, especially horizontally, pathological vestibulo-ocular reflex with corrective catch-up saccades, and pathological visual-fixation suppression of the vestibulo-ocular reflex.

Before treatment was commenced, examination of the patient indicated a Scale for Assessment and Rating of Ataxia (SARA) score of 23/40. Results from the patient's Spinocerebellar Ataxia Functional Index (SCAFI) analysis were:

Mean 8-meters Walking Test (8 MW): not able to perform

MW 9-Hole Pegboard Test Dominant (9HPTD) (right): 150 s

MW 9-Hole Pegboard Test Non-Dominant (9HPTND): 161.6 s

MW PATA Word Test: 14

Visual analog scale (as evaluated by the patient): 80

Results from video-oculography were:

TABLE 17

| Video-oculography parameters. | | |
|---|---|---|
| Slow phase velocity of the gaze-holding nystagmus [°/s] | Horizontal | Vertical |
| Center | 3 | −1.5 |
| Right | −0.4 | −1 |
| Left | 7.3 | 2.5 |
| Down | 2.4 | −0.2 |

The patient began treatment with acetyl-DL-leucine (5 g/day) about six months after the examination. After slightly over 7 months of treatment, the patient was re-evaluated. Caregivers and patient reported general improvement of well-being, without clearer specification. Examination indicated a Scale for Assessment and Rating of Ataxia (SARA) score of 21.5/40. Results from the patient's Spinocerebellar Ataxia Functional Index (SCAFI) analysis were:

Mean 8-meters Walking Test (8 MW): not able to perform

MW 9-Hole Pegboard Test Dominant (9HPTD) (right): 124.5s

MW 9-Hole Pegboard Test Non-Dominant (9HPTND): 147.5 s

MW PATA Word Test: 10

Visual analog scale (as evaluated by the patient): 80

Results from video-oculography were:

TABLE 18

| Video-oculography parameters. | | |
|---|---|---|
| Slow phase velocity of the gaze-holding nystagmus [°/s] | Horizontal | Vertical |
| Center | −0.1 | 0.4 |
| Right | −4.2 | 1.7 |
| Left | 1.7 | 0.1 |
| Down | −0.6 | 1.2 |

The patient showed slight improvement of SARA and SCAFI subset 9HPT, and significant improvement of fixation stability and decrease of intensity of gaze-holding nystagmus at all positions.

Patient 4

The patient in this case study was a 15 year-old female suffering from ataxia telangiectasia from 4-years of age. From 7-years of age, the patient showed severe cerebellar ataxia signs and symptoms, fine motor impairment, muscular hypotonia with areflexia, muscular atrophy, and plantar flexion with discrete contractures. The patient was confined to a wheelchair, but was able to walk with constant support. The patient had severe hemolytic anemia, hypogammaglobulinemia, telangiectasias on the scleras and chest, Secondary Cushing syndrome due to corticosteroid intake, and was suspected of having CNS Non-Hodgkin lymphoma.

The patient's ocular motor function showed slow deviation of the eyes upward, left beating nystagmus in the central position, gaze-holding nystagmus in all directions, horizontally with downbeating component, startle with sudden head movement.

Before treatment was commenced, examination of the patient indicated a Scale for Assessment and Rating of Ataxia (SARA) score of 23.5/40. Results from the patient's Spinocerebellar Ataxia Functional Index (SCAFI) analysis were:

Mean 8-meters Walking Test (8 MW): not able to perform

MW 9-Hole Pegboard Test Dominant (9HPTD) (right): 124.5 s

MW 9-Hole Pegboard Test Non-Dominant (9HPTND): 52.3 s

MW PATA Word Test: 14

Visual analog scale (as evaluated by the patient): 70

Results from video-oculography were:

TABLE 19

| Video-oculography parameters. | | |
|---|---|---|
| Slow phase velocity of the gaze-holding nystagmus [°/s] | Horizontal | Vertical |
| Center | −0.6 | 1.76 |
| Right | 3.7 | −0.1 |
| Left | −6 | 0.6 |
| Down | 5.7 | 2.7 |

The patient began treatment with acetyl-DL-leucine (5 g/day) following the examination. After slightly over 1 month of treatment, the patient was re-evaluated. The patient and her mother reported improvement in handwriting, especially due to decreased hand tremor and fine motor function. The patient also reported that drinking was easier and no longer needed a straw. Family members described improvement of gait, with increased stability and needing less support. Examination indicated a Scale for Assessment and Rating of Ataxia (SARA) score of 18.5/40. Results from the patient's Spinocerebellar Ataxia Functional Index (SCAFI) analysis were:

Mean 8-meters Walking Test (8 MW): not able to perform

MW 9-Hole Pegboard Test Dominant (9HPTD) (right): 93.5 s

MW 9-Hole Pegboard Test Non-Dominant (9HPTND): 101.7 s

MW PATA Word Test: 15.5

Visual analog scale (as evaluated by the patient): 70

Results from video-oculography were:

TABLE 20

| Video-oculography parameters. | | |
|---|---|---|
| Slow phase velocity of the gaze-holding nystagmus [°/s] | Horizontal | Vertical |
| Center | −0.2 | 4.8 |
| Right | −1 | 0.3 |
| Left | −0.8 | 1.9 |
| Down | −0.7 | −2.3 |

The patient showed improvement of SARA and SCAFI subset 9HPT of the dominant hand. Video-oculography showed general improvement of fixation stability and decrease of intensity of spontaneous and gaze-holding nystagmus at all positions.

Patient 5

The patient in this case study was a 10 year-old boy suffering from ataxia telangiectasia from his early childhood, having:

Delayed psychomotor development, instable walking at 14 months with increased incidence of falls, severe cerebellar ataxia signs and symptoms, dysarthria and dyslalia, fine motor impairment, infrequent head tremor, slow psychomotor tempo, hypotonia with muscular atrophy and hyporeflexia, anteflexia of the head with kyphosis in the thoracal area, pedes transversoplani, scapullae allatae, parasomnia with pavor nocturnus, and autism; and Significant immunosuppression, telangiectasias on the soft palate, scleras, incontinence, and asthenic habitus.

The patient was confined to a wheelchair but was able to perform a few steps with strong constant support. The patient's ocular motor function showed oculomotor apraxia with pronounced head anteflexia, head and eye movement "en bloc" when looking to the right and left, vertical gaze palsy with slow vertical saccades and saccadic smooth pursuit, slow horizontal saccades to the left, saccade palsy to the right, restricted eye motility, especially vertically, and fixation instability in all positions.

Before treatment was commenced, examination of the patient indicated a Scale for Assessment and Rating of Ataxia (SARA) score of 24.5/40. Results from the patient's Spinocerebellar Ataxia Functional Index (SCAFI) analysis were:

Mean 8-meters Walking Test (8 MW): not able to walk without constant support

MW 9-Hole Pegboard Test Dominant (9HPTD) (right): 102.7 s

MW 9-Hole Pegboard Test Non-Dominant (9HPTND): 116.8 s

MW PATA Word Test: 6

Visual analog scale (as evaluated by the patient): 90

Results from video-oculography were:

TABLE 21

| Video-oculography parameters. Slow-phase velocity (SPV) of fixation and gaze-holding nystagmus, [°/s] | | |
|---|---|---|
| | Horizontal | Vertical |
| Center | 0.96 | 1.53 |
| Right | 0.21 | 2 |
| Left | 2.1 | 3.64 |
| Down | 0.71 | 3.91 |
| Up | 0.31 | 1.69 |

The patient began treatment with acetyl-DL-leucine (5 g/day) following examination. After about 1 month of treatment, the patient was re-evaluated. The patient's mother described a significant improvement of stability of the gait; prior to the therapy, he was constantly falling backward and had to be partially "transported". On medication, he was able to walk with only holding the caregiver's hand.

Fine motor function, the intensity of hand tremor, and body holding improved. Improvement of fine motor function was reflected in daily activities, such as eating and drinking independently. The patient gained 1.5 kg and had a better appetite. Examination indicated a Scale for Assessment and Rating of Ataxia (SARA) score of 20.5/40. Results from the patient's Spinocerebellar Ataxia Functional Index (SCAFI) analysis were:

Mean 8-meters Walking Test (8 MW): not able to walk without support

MW 9-Hole Pegboard Test Dominant (9HPTD) (right): 103.6 s

MW 9-Hole Pegboard Test Non-Dominant (9HPTND): 88.8 s

MW PATA Word Test: 7.5

Visual analog scale (as evaluated by the patient): 80

Results from video-oculography were:

TABLE 22

| Video-oculography parameters. Slow-phase velocity (SPV) of fixation and gaze-holding nystagmus, [°/s] | | |
|---|---|---|
| | Horizontal | Vertical |
| Center | 0.79 | 3.54 |
| Right | 1.17 | 2.36 |
| Left | 1.22 | 2.53 |
| Down | 0.62 | 1.08 |
| Up | 0.33 | 1.71 |

After almost 7 months of treatment, the patient was again re-evaluated. The patient's mother described significantly more stable gait; this finding remained constant from the first evaluation after treatment. The patient had improved concentration and speech. The patient could stand up on his own and was generally more independent with daily activities. The patient gained another 3 kg with improved appetite and showed improved strength.

Examination indicated a Scale for Assessment and Rating of Ataxia (SARA) score of 17.5/40. Results from the patient's Spinocerebellar Ataxia Functional Index (SCAFI) analysis were:

Mean 8-meters Walking Test (8 MW): 15.3 s (holding of the hand)

MW 9-Hole Pegboard Test Dominant (9HPTD) (right): 92.4 s

MW 9-Hole Pegboard Test Non-Dominant (9HPTND): 98.3 s

MW PATA Word Test: 11

Visual analog scale (as evaluated by the patient): 100

The patient was re-evaluated after slightly over a year of treatment and showed improved social interaction, activity, and agility. The patient's parents reported improvement of incontinence. The patient developed a repeatedly occurring frontal localized pain with vomiting in the morning. Based on family history, it was suspected that the localized pain may be due to infantile migraine.

Examination indicated a Scale for Assessment and Rating of Ataxia (SARA) score of 16.5/40. Results from the patient's Spinocerebellar Ataxia Functional Index (SCAFI) analysis were:

Mean 8-meters Walking Test (8 MW): 13.9 s (able to walk by himself, mother held hand)

MW 9-Hole Pegboard Test Dominant (9HPTD) (right): 95.6 s

MW 9-Hole Pegboard Test Non-Dominant (9HPTND): 127.6 s

MW PATA Word Test: 14.5

Visual analog scale (as evaluated by the patient): 95

On treatment with acetyl-DL-leucine, the patient showed improved SARA and SCAFI subtests, increased quality of life, generally improved fixation stability and decrease of intensity of spontaneous and gaze-holding nystagmus, especially in the vertical plane (after 1 month).

Patient 6

The patient in this case study was a 10 year-old female suffering from ataxia telangiectasia who had ataxic gait and stance, fine motor function disorder with hand tremor, dysphagia and speech disorder, ocular movement disorder, and problems with cognitive function and concentration. First symptoms were observed at the age of one year.

After baseline examination, the patient started acetyl-DL-leucine treatment at 1.5 g/day for the first week and at 3 g/day for the second week onwards. The patient was evaluated after one month and six months of treatment, respectively. After one month of treatment, the patient showed increased fine motor skills with reduced hand tremor, improved postural stability and gait, increased enunciation, and increased self-confidence. After six months of treatment, the patient had stable general conditions, stable gait and stance, and improved handwriting. The patient, however, was suffering from anxiety, which would be expected to negatively influence the response.

The patient's SARA and SCAFI scores at each evaluation are shown below.

TABLE 23

| Patient Evaluation parameters. | | | |
|---|---|---|---|
| | Baseline | After one month of acetyl-DL-leucine treatment | After six months of acetyl-DL-leucine treatment |
| SARA | 11/40 | 8.5/40 | 11/40 |
| 8MWT | 8.95 sec | 8.45 sec | 7.53 sec |
| 9HPTD | 85.38 sec | 81.95 sec | 136.27 sec |
| 9HPTND | 71.2 sec | 70.39 sec | 80.32 sec |
| PATA | 14.5 | 15.5 | 13 |

Example 16

The patient in this case study was a female in her early 60s who was genetically diagnosed with Spinocerebellar Ataxia (SCA) 1. Before treatment, the patient had severe problems with speaking and swallowing, tremor of both arms, spasticity and moderate ataxia of stance and gait. The patient also had problems sleeping.

Three weeks on medication with acetyl-DL-leucine (5 g/day), all symptoms significantly improved, as further demonstrated by clinical examination, including spasticity and impairment of ocular motor function.

Three months later the medication was stopped. After two weeks, the intensity of the signs and symptoms were the same as before therapy. Treatment was started again, and the patient has remained, and continues, on the treatment after over two years, on the same dosage without any side-effects.

The patient's daughter reported considerable progression of the disease over time with a persisting symptomatic effect, yet observed, anecdotally, that there was long-term symptomatic efficacy from treatment.

Example 17

The patient in this case study was a 70 year-old female with insecure gait and frequent falls, visual hallucinations at night, REM-sleep disorder. The patient had symmetric hypokinetic-rigid syndrome with impairment of fine motor skills and fluctuations in attention and awareness.

The patient was diagnosed with Lewy Body dementia. FDG-PET of the brain showed a synaptic dysfunction in the parietal and occipital lobe and DATscan showed a degeneration of presynaptic dopamine transporter, supporting the diagnosis. Treatment with Levodopa 100 mg 4×daily and Quetiapin 25 mg at night improved the symptomatology.

The patient started taking acetyl-leucine (3 g/day for one week; 5 g/day thereafter) and was evaluated after four weeks. The patient reported increased fatigue and a deterioration of balance and speech. Medication was reduced to 3 g/day, and the patient was instructed to stop medication about two weeks later.

The patient was re-evaluated about one month after ceasing medication and did not report improvement of symptomatology with the decreased dose and no deterioration of symptoms after stopping medication.

TABLE 24

Gait parameters.

| — | After 1 week on acetyl-DL-leucine | After 4 weeks on acetyl-DL-leucine | Normal value (±SD) |
|---|---|---|---|
| speed (cm/sec) | 55 | 56 | 119.12 (17.27) |
| Max. speed (cm/sec) | 92 | 74 | 176.78 (19.10) |
| cadence (steps/minute) | 81 | 85 | 113.06 (10.38) |
| Track width (cm) | 4.6 | 6.7 | 9.49 (3.56) |
| Step cycle length (cm) | 81 | 79 | 126.71 (13.06) |
| Double stance (%) | 36.1 | 38.7 | 20.35 (3.21) |
| Coefficient of variation (temporal) | 9.1 | 8.8 | 1.76 (0.73) |
| Functional Gait Assessment | | 11/30 | 27.1 (2.3) |

Example 18

In this case study, four patients (male siblings) suffered from, and were later diagnosed with, ataxia with oculomotor apraxia type 4. The older three siblings were 12, 11, and 10 years of age, respectively, at the time of disease onset. Prior to commencing treatment with acetyl-DL-leucine, by the age of 15/16 years, the three older siblings walked with an expedient, as reported by the patients' mother. The older siblings began treatment with acetyl-leucine at 25, 23, and 19 years of age, respectively, and have been on the treatment for approximately four years. No long-term clinical data is available for these three patients.

The youngest sibling was 11 years old at the time of onset. He began treatment with acetyl-DL-leucine at the age of 13. While on treatment, the youngest sibling did not walk with an expedient until nearly 18 years of age, as reported by the patient's mother. The patient's mother also reported that the youngest sibling had improved fine motor skills and improved speech at each age compared to his older siblings. No long-term clinical data is available for the youngest sibling.

Example 19

An NPC patient's severity may be quantified by assigning a clinical severity score (CSS), which assesses various parameters of the disease and gives each parameter a score out of 5 (higher score=greater severity). See Yanjanin et al., "Linear Clinical Progression, Independent of Age of Onset, in Niemann-Pick Disease, Type C," *Am J Med Genet Part B* 153B:132-140. In an untreated patient, one can typically predict how the CSS will change over time in an individual, as disease progression appears to be linear. For example, if Patient A moves from a CSS of 8 to a CSS of 12 between month 0 and month 12, it can be predicted that by month 36, the patient will have a CSS of 20. The annual severity increment score (ASIS) quantities the annual rate of change in the CSS, calculated by dividing the CSS of a patient by the patient's age. For example, if untreated Patient B had a CSS of 8 at two years of age, the patient's ASIS would be 4. Each year, the patient would be expected to progress by 4 CSS points, such that at 4 years of age, the patient's CSS would be 16. If therapeutic intervention slowed or arrested disease progression, one would expect the patient to have a smaller ASIS score after such therapy than at baseline.

Ten NPC patients were administered acetyl-leucine at 4.5 g/day over long durations. A CSS was determined at baseline, and at various time points, for eye movement, ambulation, speech, swallow, fine motor skills, cognition, memory, and seizures. An overall CSS was calculated at baseline and at each such time point by adding the individual CSS values for each parameter (eye movement, ambulation, etc.). The number of days post-initiation of therapy at which CSS was assessed was different for each patient, as shown in Table 25.

TABLE 25

Days post-initiation of acetyl-leucine administration at which CSS was assessed

| Patient I.D | Baseline (days) | Time Point 2 (days) | Time Point 3 (days) | Time Point 4 (days) |
|---|---|---|---|---|
| 1 | 0 | 126 | 231 | |
| 2 | 0 | 119 | 200 | 297 |
| 3 | 0 | 91 | 240 | |
| 4 | 0 | 107 | 196 | |
| 5 | 0 | 78 | 238 | 414 |
| 6 | 0 | 184 | 238 | 414 |
| 7 | 0 | 81 | 165 | |
| 8 | 0 | 90 | 217 | |
| 9 | 0 | 400 | 644 | |
| 10 | 0 | 83 | | |

Tables 26-34 below show each CSS for overall, eye movement, ambulation, speech, swallow, fine motor skills, cognition, memory, and seizures, respectively.

TABLE 26

CSS overall.

| Clinical Severity Score (CSS) Patient I.D | Baseline | Time Point 2 | Time Point 3 | Time Point 4 |
|---|---|---|---|---|
| 1 | 11 | 11 | 10 | |
| 2 | 33 | 33 | 33 | 33 |
| 3 | 13 | 12 | 11 | |
| 4 | 13 | 13 | 10 | |
| 5 | 12 | 12 | 12 | 12 |
| 6 | 21 | 23 | 21 | 21 |
| 7 | 19 | 19 | 19 | |
| 8 | 13 | 12 | 11 | |
| 9 | 22 | 22 | 21 | |
| 10 | 14 | 11 | | |

TABLE 27

CSS eye movement.

| Clinical Severity Score (CSS) Patient I.D | Baseline | Time Point 2 | Time Point 3 | Time Point 4 |
|---|---|---|---|---|
| 1 | 3 | 3 | 3 | |
| 2 | 3 | 3 | 3 | 3 |
| 3 | 3 | 3 | 3 | |
| 4 | 2 | 2 | 2 | |
| 5 | 3 | 3 | 3 | 3 |
| 6 | 3 | 3 | 3 | 3 |
| 7 | 3 | 3 | 3 | |
| 8 | 3 | 3 | 2 | |
| 9 | 3 | 3 | 3 | |
| 10 | 3 | 3 | | |

TABLE 28

CSS ambulation.

| Clinical Severity Score (CSS) Patient I.D | Baseline | Time Point 2 | Time Point 3 | Time Point 4 |
|---|---|---|---|---|
| 1 | 2 | 2 | 1 | |
| 2 | 5 | 5 | 5 | 5 |
| 3 | 1 | 1 | 1 | |
| 4 | 2 | 2 | 1 | |
| 5 | 1 | 1 | 1 | 1 |
| 6 | 2 | 4 | 2 | 2 |
| 7 | 2 | 2 | 2 | |
| 8 | 1 | 1 | 1 | |
| 9 | 2 | 2 | 2 | |
| 10 | 2 | 2 | | |

TABLE 29

CSS speech.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 2 | 2 | 2 | 2 |
| 3 | 1 | 1 | 1 | |
| 4 | 2 | 2 | 1 | |
| 5 | 1 | 1 | 1 | 1 |
| 6 | 2 | 2 | 2 | 2 |
| 7 | 1 | 1 | 1 | |
| 8 | 1 | 1 | 1 | |
| 9 | 2 | 2 | 2 | |
| 10 | 1 | 1 | | |

TABLE 30

CSS swallow.

| Clinical Severity Score (CSS) Patient I.D | Baseline | Time Point 2 | Time Point 3 | Time Point 4 |
|---|---|---|---|---|
| 1 | 0 | 0 | 0 | |
| 2 | 4 | 4 | 4 | 4 |
| 3 | 2 | 2 | 2 | |
| 4 | 2 | 2 | 2 | |
| 5 | 2 | 2 | 2 | 2 |
| 6 | 3 | 3 | 3 | 3 |
| 7 | 3 | 3 | 3 | |
| 8 | 2 | 2 | 2 | |
| 9 | 3 | 3 | 3 | |
| 10 | 2 | 2 | | |

TABLE 31

CSS fine motor skills.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 5 | 5 | 5 | 5 |
| 3 | 2 | 1 | 1 | |
| 4 | 1 | 1 | 1 | |
| 5 | 1 | 1 | 1 | 1 |
| 6 | 4 | 4 | 4 | 4 |
| 7 | 2 | 2 | 2 | |

TABLE 31-continued

CSS fine motor skills.

| Clinical Severity Score (CSS) Patient I.D | Baseline | Time Point 2 | Time Point 3 | Time Point 4 |
|---|---|---|---|---|
| 8 | 2 | 1 | 1 | |
| 9 | 4 | 4 | 4 | |
| 10 | 1 | 1 | | |

TABLE 32

CSS cognition.

| Clinical Severity Score (CSS) Patient I.D | Baseline | Time Point 2 | Time Point 3 | Time Point 4 |
|---|---|---|---|---|
| 1 | 3 | 3 | 3 | |
| 2 | 5 | 5 | 5 | 5 |
| 3 | 3 | 3 | 3 | |
| 4 | 3 | 3 | 3 | |
| 5 | 3 | 3 | 3 | 3 |
| 6 | 4 | 4 | 4 | 4 |
| 7 | 4 | 4 | 4 | |
| 8 | 3 | 3 | 3 | |
| 9 | 4 | 4 | 4 | |
| 10 | 3 | 2 | | |

TABLE 33

CSS memory.

| Clinical Severity Score (CSS) Patient I.D | Baseline | Time Point 2 | Time Point 3 | Time Point 4 |
|---|---|---|---|---|
| 1 | 1 | 1 | 1 | |
| 2 | 4 | 4 | 4 | 4 |
| 3 | 1 | 1 | 0 | |
| 4 | 1 | 1 | 0 | |
| 5 | 1 | 1 | 1 | 1 |
| 6 | 3 | 3 | 3 | 3 |
| 7 | 4 | 4 | 4 | |
| 8 | 1 | 1 | 1 | |
| 9 | 4 | 4 | 3 | |
| 10 | 2 | 0 | | |

TABLE 34

CSS seizures.

| Clinical Severity Score (CSS) Patient I.D | Baseline | Time Point 2 | Time Point 3 | Time Point 4 |
|---|---|---|---|---|
| 1 | 0 | 0 | 0 | |
| 2 | 5 | 5 | 5 | 5 |
| 3 | 0 | 0 | 0 | |
| 4 | 0 | 0 | 0 | |
| 5 | 0 | 0 | 0 | 0 |
| 6 | 0 | 0 | 0 | 0 |
| 7 | 0 | 0 | 0 | |
| 8 | 0 | 0 | 0 | |
| 9 | 0 | 0 | 0 | |
| 10 | 0 | 0 | | |

The ASIS at baseline and each time point was calculated using each patient's CSS and age at the time of assessment. The overall ASIS for each patient at each time point is shown below in Table 35.

TABLE 35

| ASIS overall. | | | |
|---|---|---|---|
| Annual Severity Increment Scores (ASIS) Baseline | Time Point 2 | Time Point 3 | Time Point 4 |
| 0.381371618 | 0.376864272 | 0.339262493 | |
| 1.94125463 | 1.904748736 | 1.880675612 | 1.852636028 |
| 0.65 | 0.592617631 | 0.53250497 | |
| 0.481909063 | 0.476731928 | 0.363469002 | |
| 0.433188377 | 0.429874461 | 0.423232908 | 0.416160273 |
| 0.561964246 | 0.607297766 | 0.552333117 | 0.545420607 |
| 0.536675431 | 0.533334614 | 0.529913714 | |
| 0.486750384 | 0.445200609 | 0.402903129 | |
| 0.738624874 | 0.71243018 | 0.665646967 | |
| 0.595597228 | 0.406038403 | | |

Figure 10A:
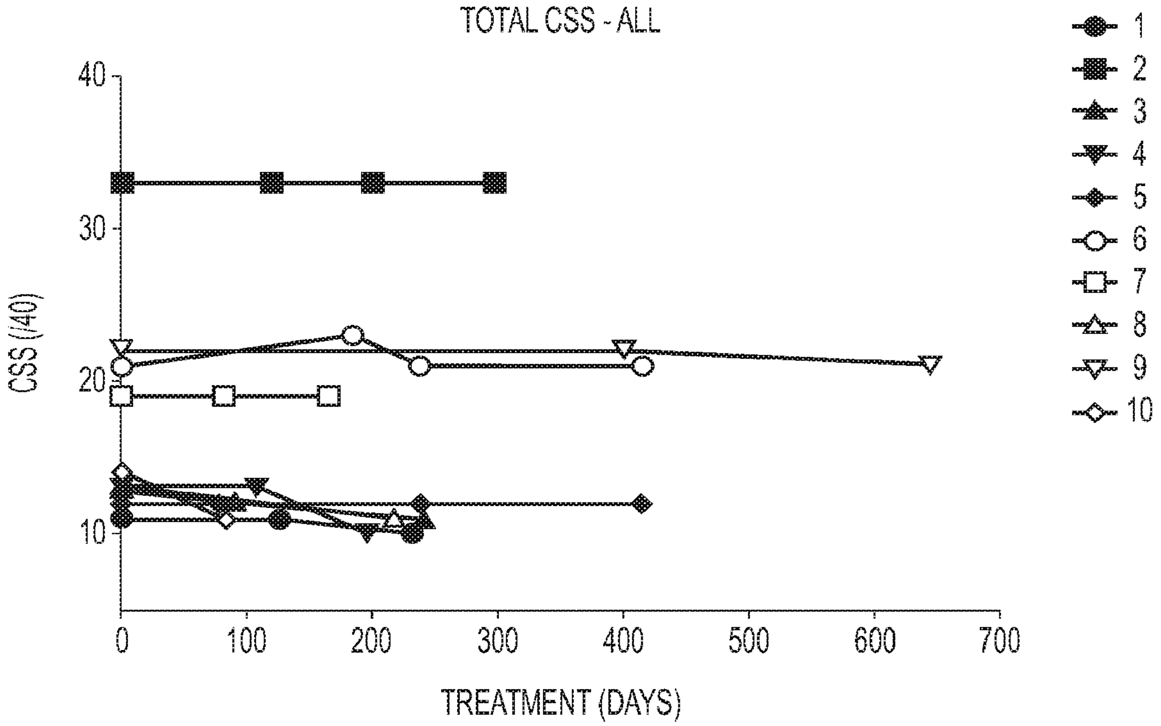
FIGS. 10A and 10B show the effect of treatment with acetyl-DL-leucine over time on the overall clinical severity score (CSS) and overall annual severity increment score (ASIS), respectively, of ten NPC patients.

As shown in Table 26 and FIG. 10A, none of the ten patients showed an overall increase in CSS over the course of the experiment. Patient 6 showed an increased CSS between baseline and time point 2, but returned to baseline by time point 3 and remained there at time point 4. Four of the ten patients (Patients 2, 5, 6, and 7) had a constant CSS over the course of the experiment, indicating that the disease did not progress in these individuals. Six of the ten patients (Patients 1, 3, 4, 8, 9, and 10) showed a reduction in CSS over the course of the experiment, indicating that the disease did not progress and actually became less severe. Improvements were seen in different subscores: Patient 1: ambulation; Patient 3: fine motor skills; Patient 4: ambulation and speech; Patient 8: eye movement and fine motor skills; Patient 9: memory; Patient 10: cognition. Data presented in FIGS. 11A-11J show the CSS subscores for each patient, respectively, in the form of a bar graph.

Figure 10B:
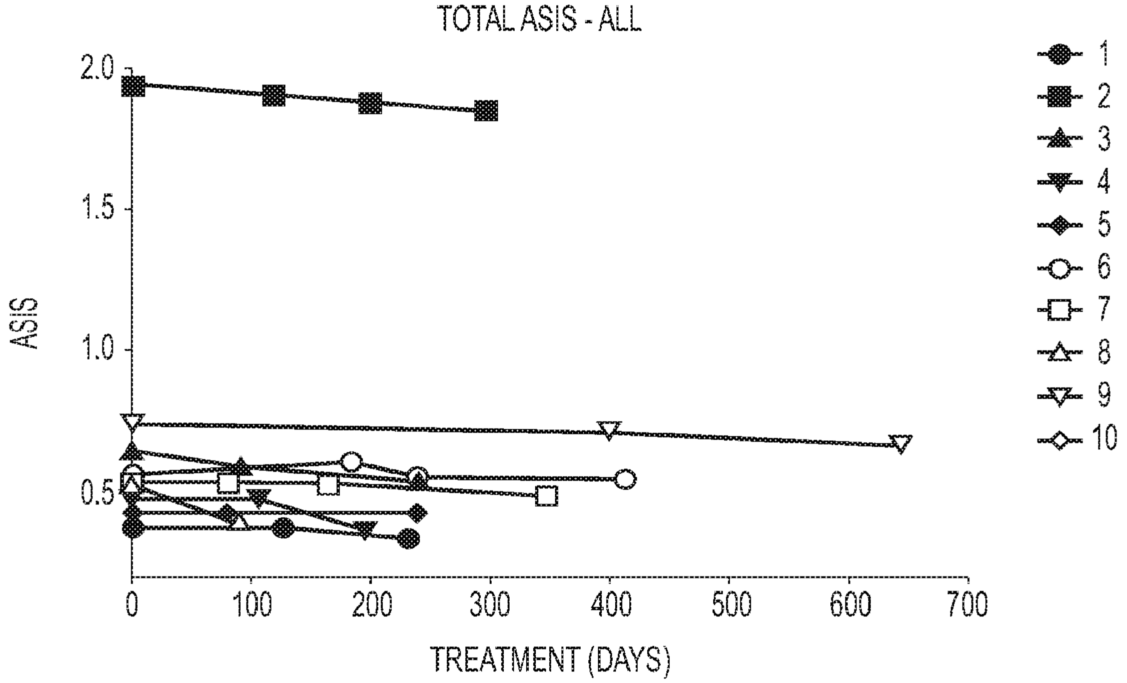
Figure 11A:
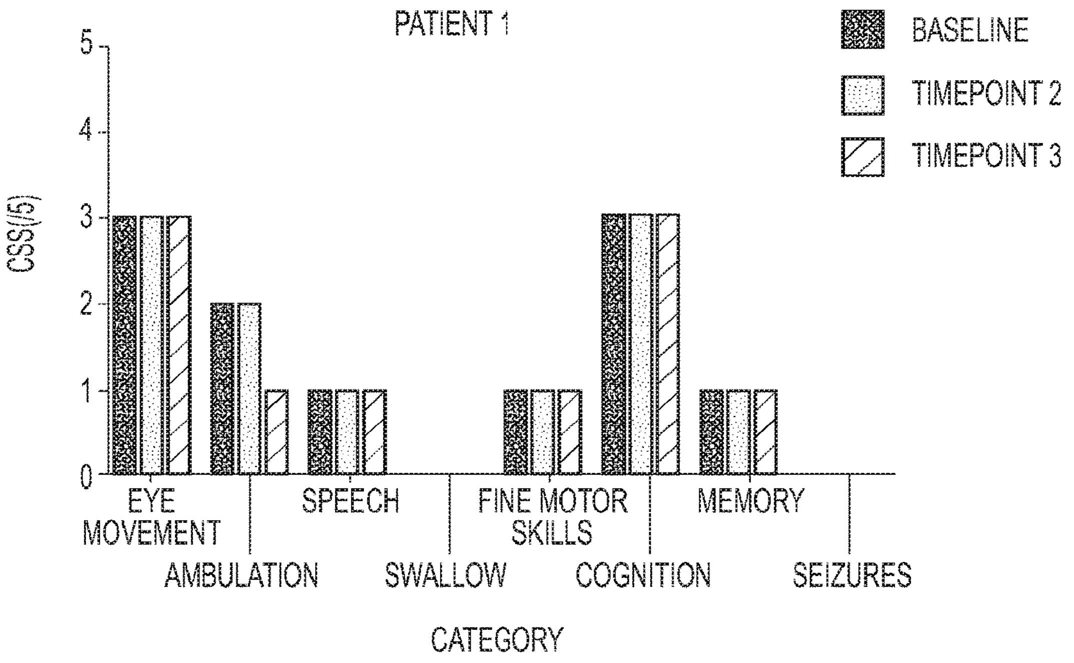
FIGS. 11A-11J show the effect of treatment with acetyl-DL-leucine over time on the CSS subscores for each of the ten NPC patients.
Figure 11B:
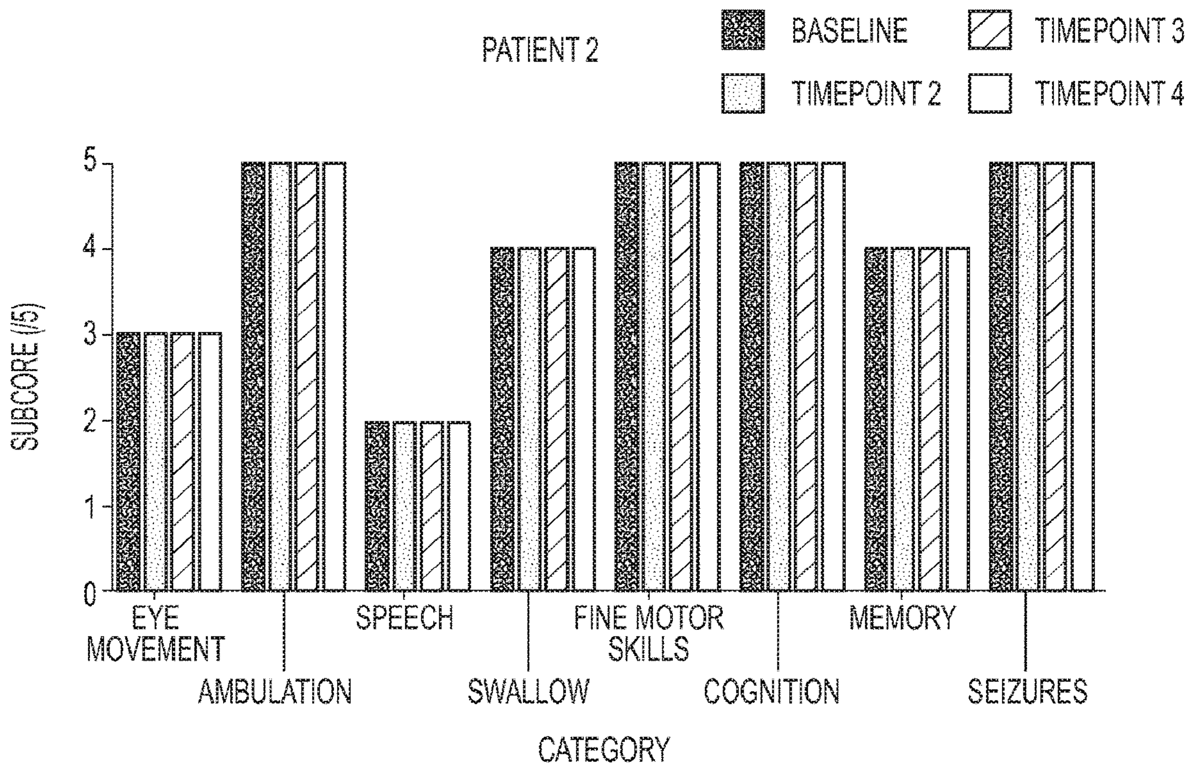
Figure 11C:
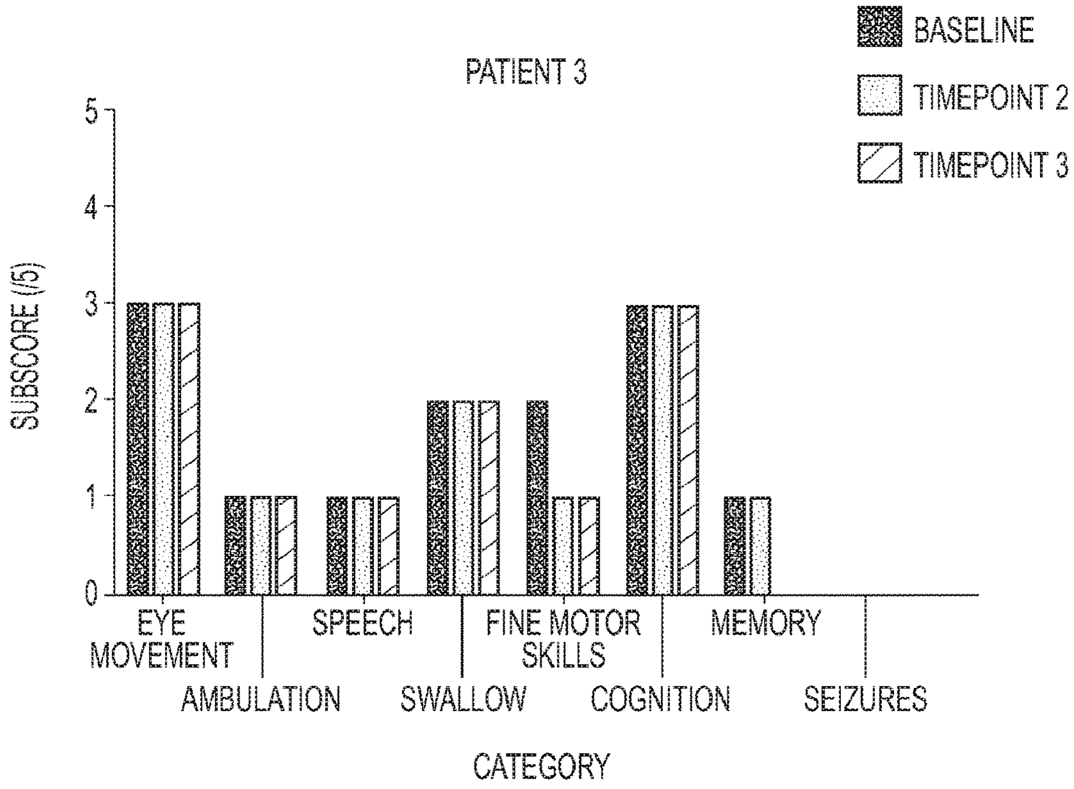
Figure 11D:
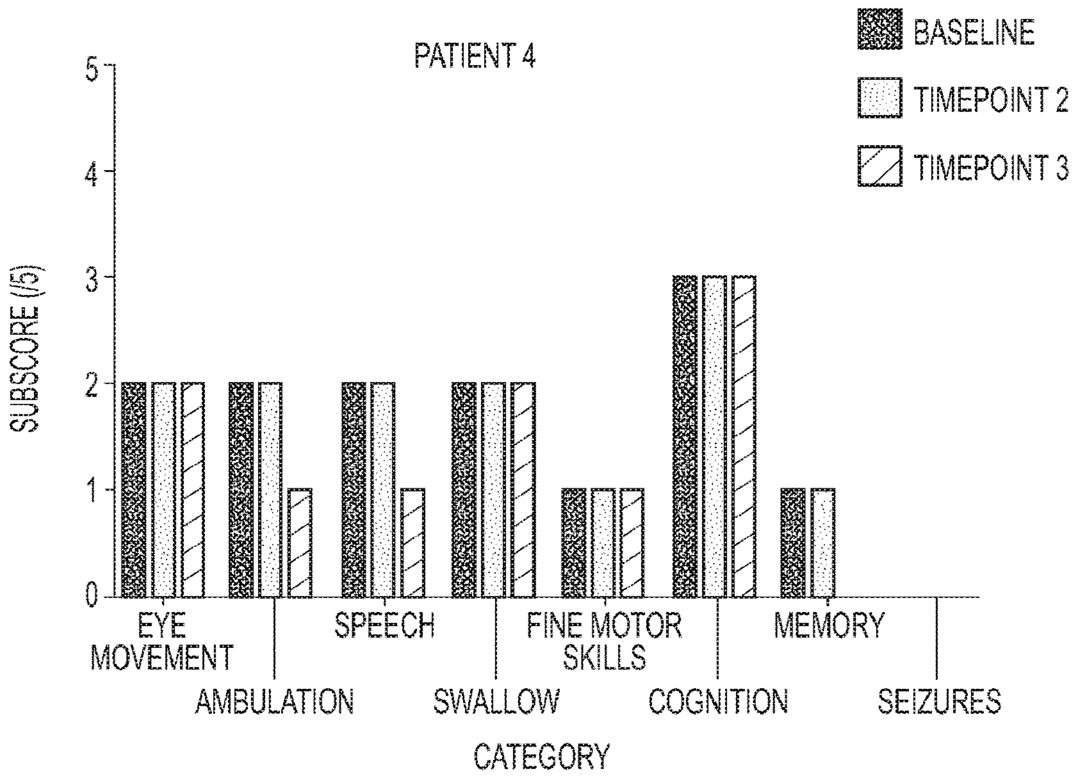
Figure 11E:
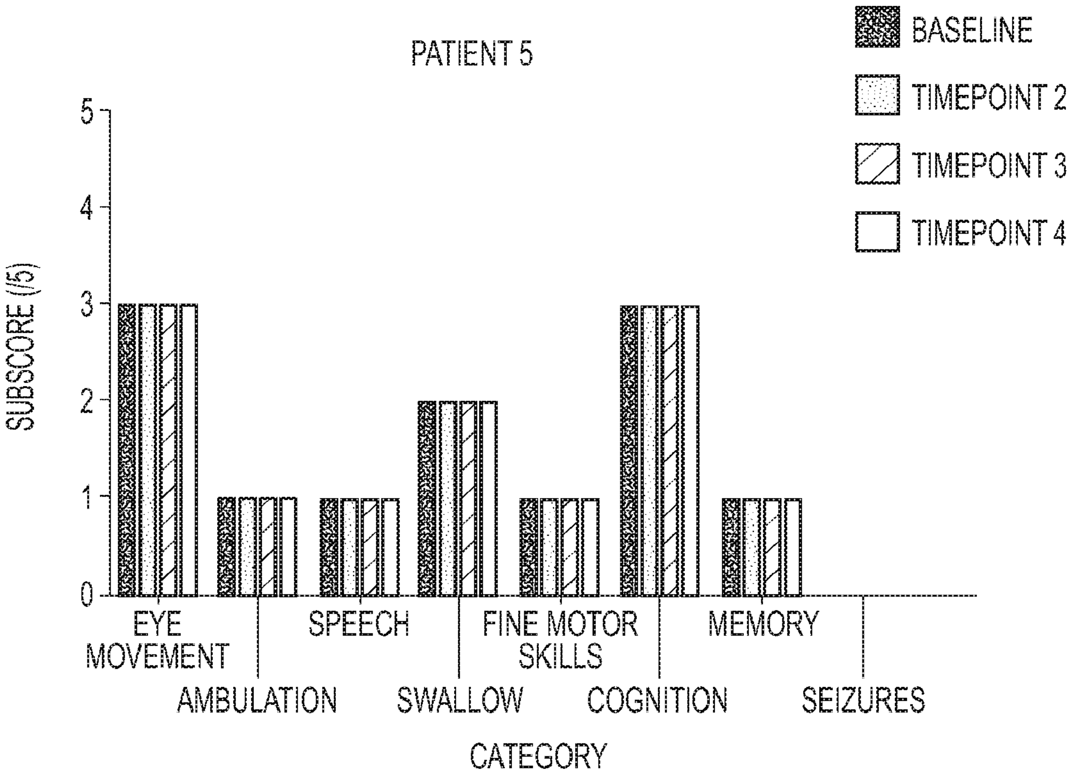
Figure 11F:
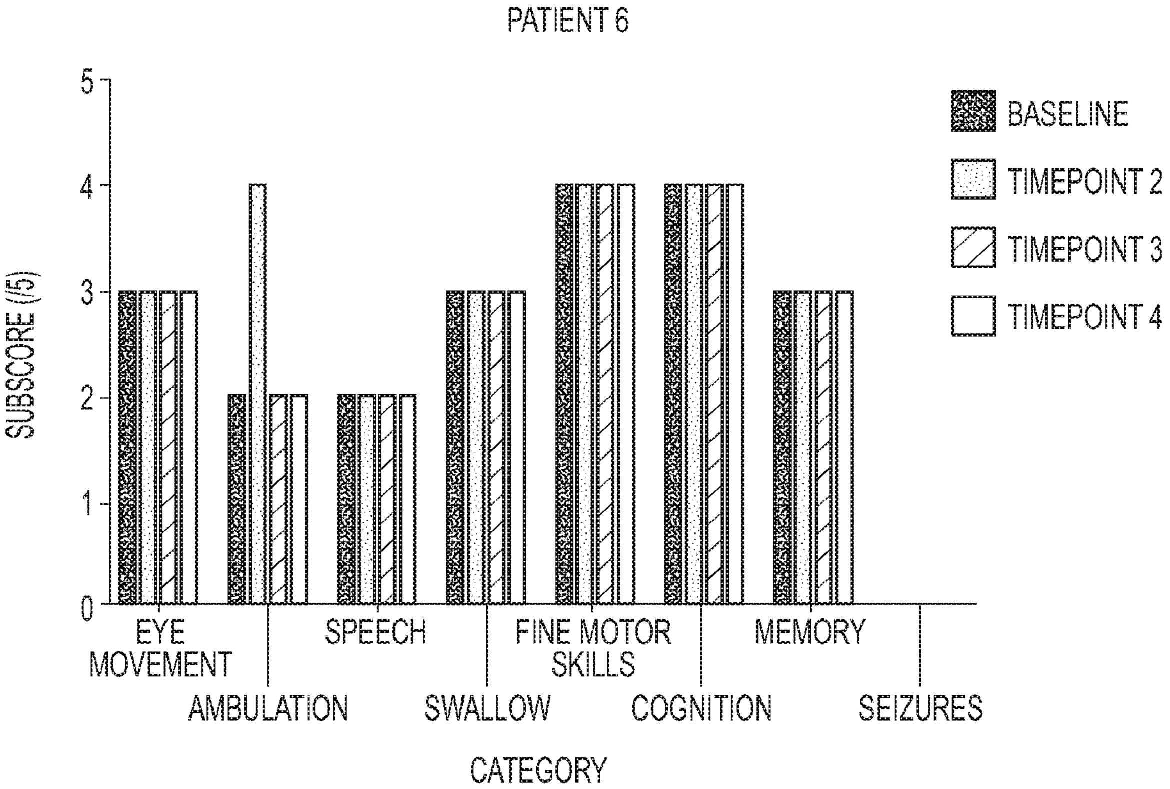
Figure 11G:
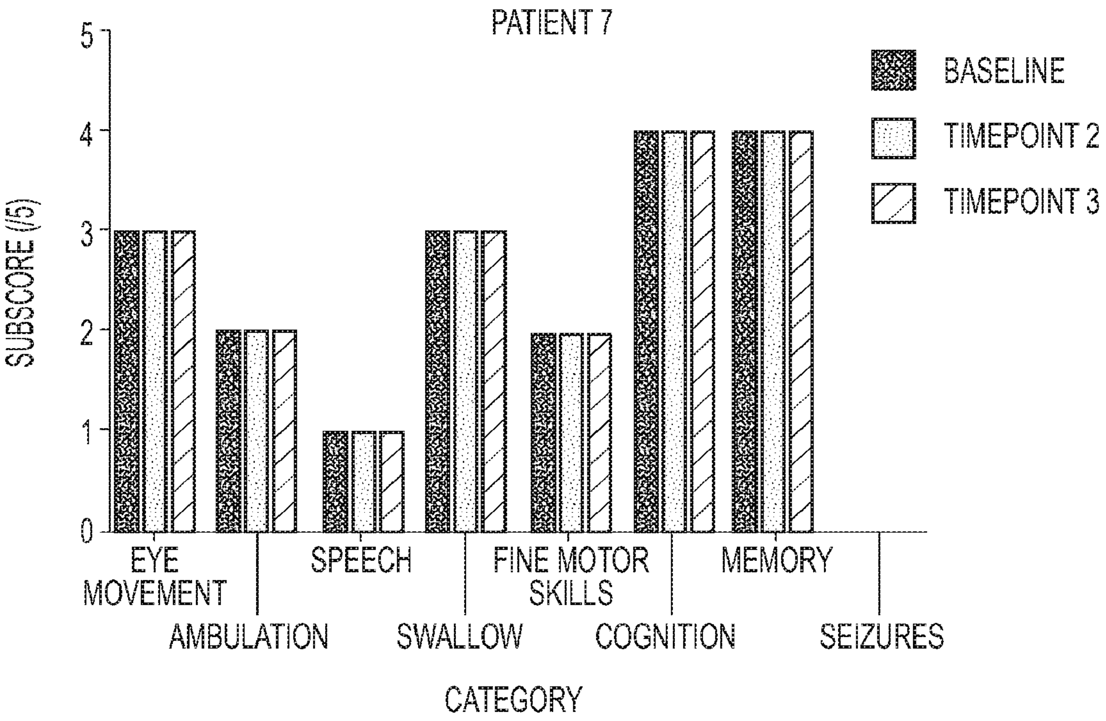
Figure 11H:
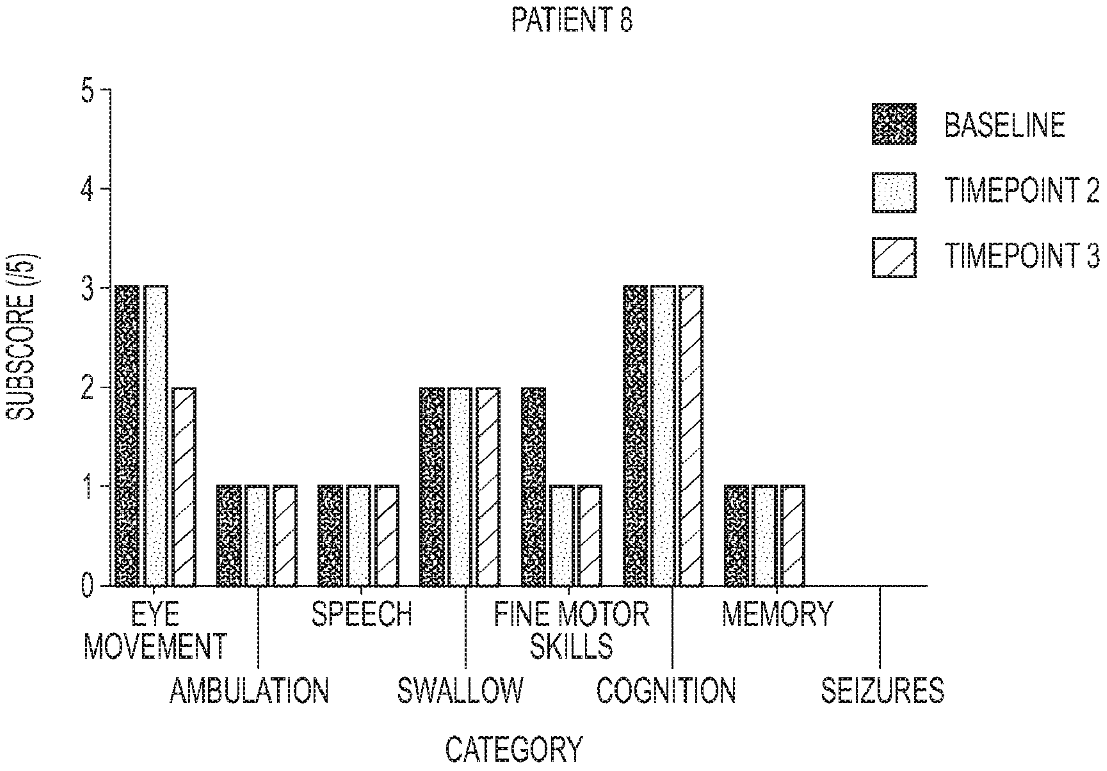
Figure 11I:
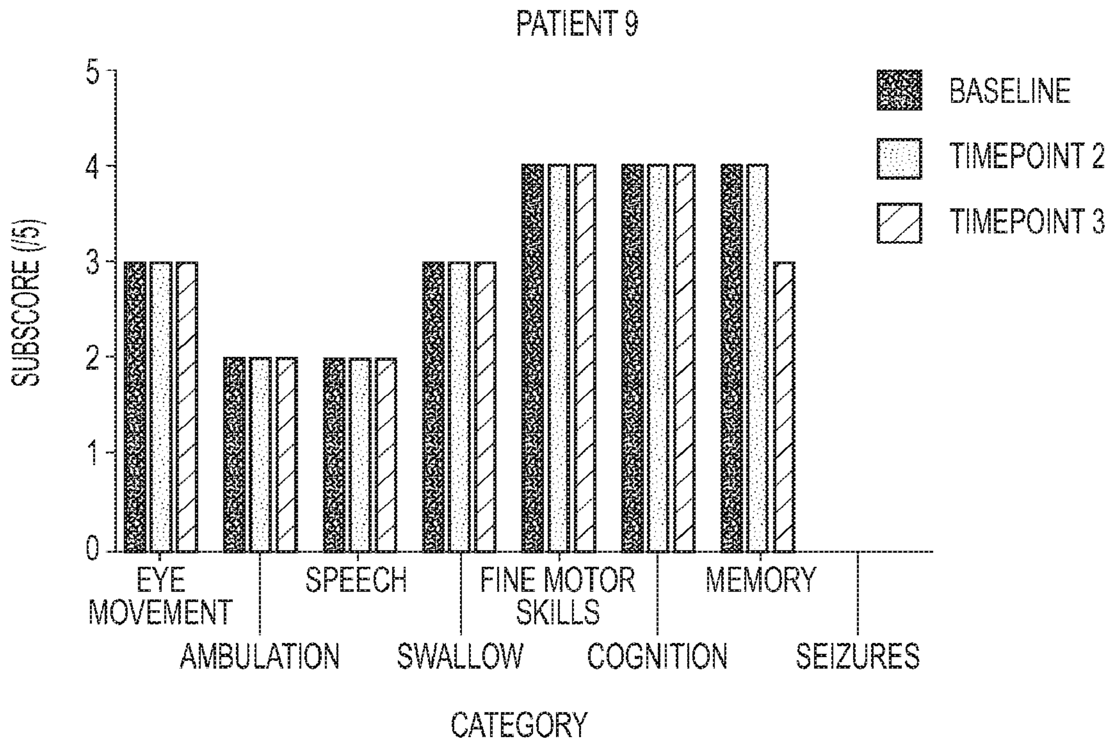
Figure 11J:
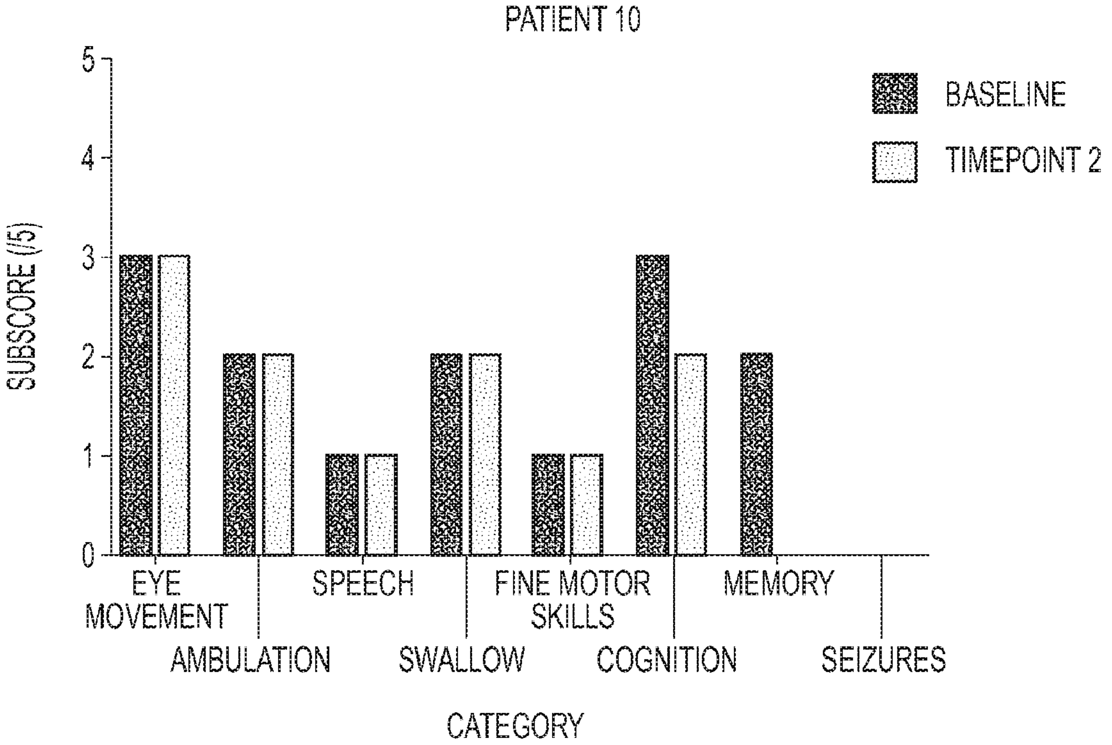

As shown in Table 35 and FIGS. 10B, all ten patients showed a reduction in ASIS during treatment relative to ASIS at baseline. In Patients 2, 5, 6, and 7, CSS remained the same while age increased, resulting in a small reduction in ASIS. In Patients 1, 3, 4, 8, 9, and 10, the reduction in ASIS was larger due to CSS decreasing while age increased.

Example 20

The Niemann-Pick Disease Type C (NPC) mouse model shares a number of pathological features with Alzheimer's disease (AD) as described herein. Wild type $NPC1^{-/-}$ mice were treated with acetyl-dl-leucine (0.1 g/kg body weight daily) from 3 weeks of age. Mice were sacrificed at 8 weeks of age. Levels of amyloid precursor protein C-terminal fragments (APP-CTFs) were evaluated relative to total amyloid precursor protein (APP) levels in the cerebellum for wild type, untreated wild type $NPC1^{-/-}$ mice, and AL-treated wild type $NPC1^{-/-}$ mice. Levels of microtubule-associated protein 1A/1B-light chain 3-phosphatidylethanolamine conjugate (LC3-II) were also evaluated relative to levels of tubulin loading control for wild type, untreated wild type $NPC1^{-/-}$ mice, and AL-treated wild type $NPC1^{-/-}$ mice.

Figure 12A:
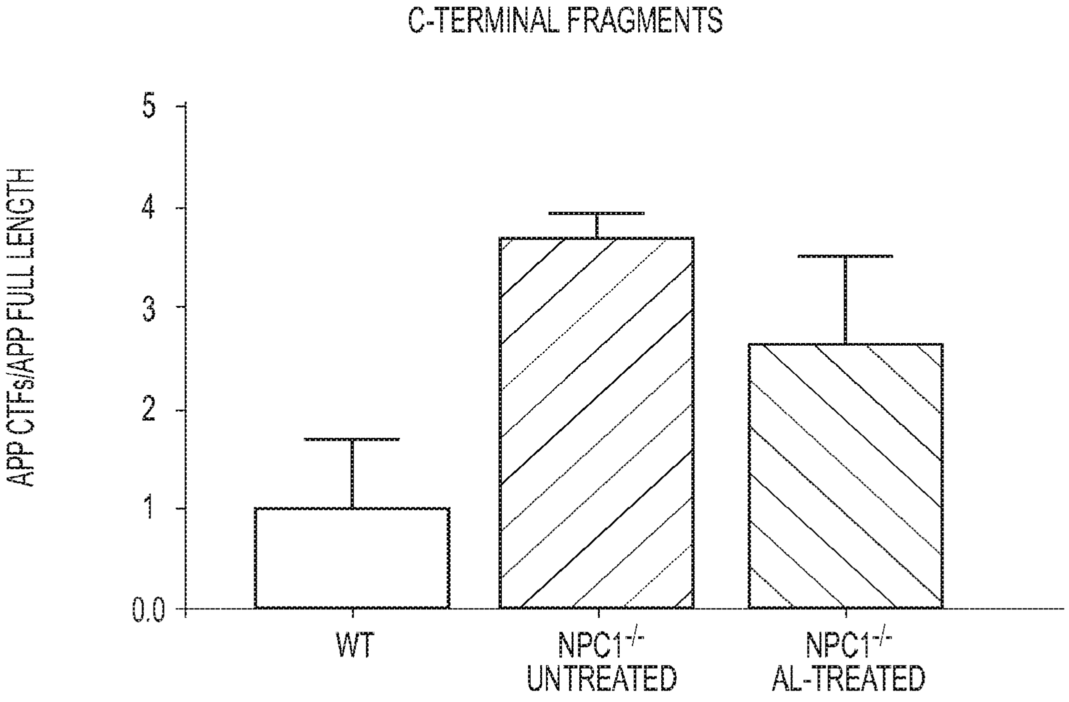
FIGS. 12A and 12B show the effect of treating wild type $NPC1^{-/-}$ mice with acetyl-DL-leucine on levels of amyloid precursor protein C-terminal fragments (APP-CTFs) and levels of microtubule-associated protein 1A/1B-light chain 3-phosphatidylethanolamine conjugate (LC3-II), respectively.

The APP-CTF data is shown in FIG. 12A. The data replicated the previously noted accumulation of APP-CTFs in the NPC1 mouse brain. Treatment with acetyl-dl-leucine was associated with lowering of APP-CTFs.

Figure 12B:
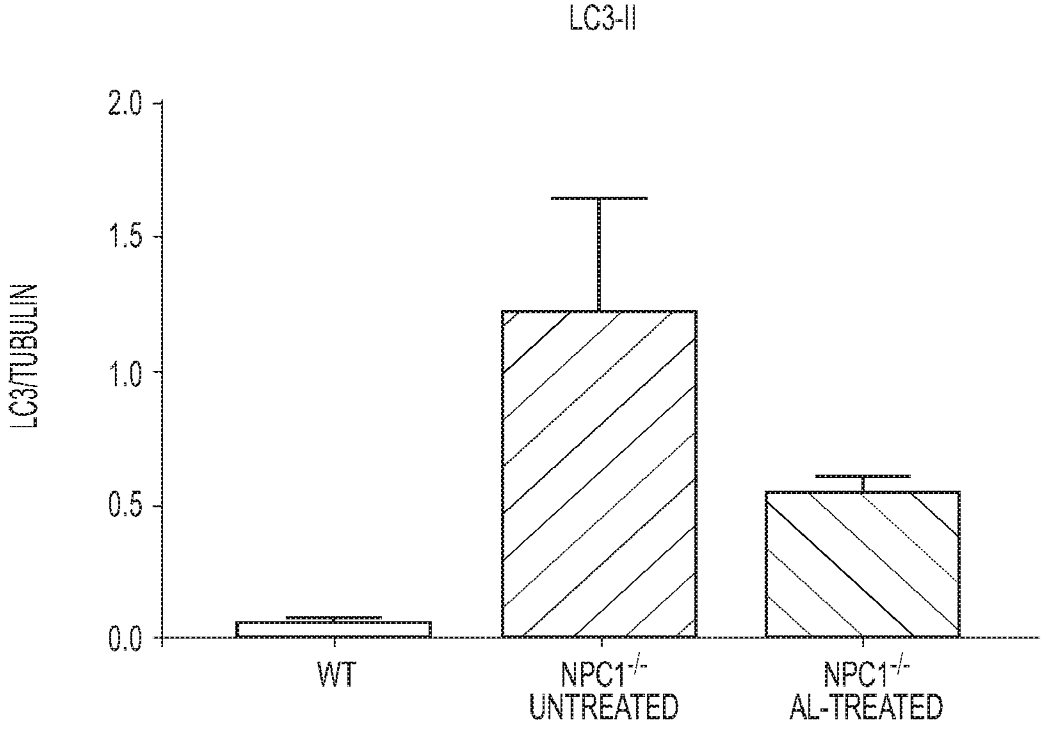

The LC3-II data is shown in FIG. 12B. The data replicated the previously noted accumulation of LC3-II in the NPC1 mouse brain. Treatment with acetyl-dl-leucine was associated with a lowering of LC3-II, indicative of a partial restoration of autophagic flux.

CONCLUSION

Acetyl-leucine treatment was associated with an improvement in AD pathology in the NPC1 mouse brain.

The invention claimed is:

1. A method of treating reduced sleep quality in a subject in need thereof comprising: administering a therapeutically effective amount of acetyl-leucine or a pharmaceutically acceptable salt thereof to the subject, wherein the reduced sleep quality is associated with a neurodegenerative disease, wherein the neurodegenerative disease is chosen from multiple system atrophy (MSA-P/MSA-C), Parkinson's Disease, Lewy Body dementia, and frontotemporal dementia with parkinsonism.

2. The method of claim 1, wherein the reduced sleep quality is REM Sleep Behavior Disorder (RBD).

3. The method according to claim 1, wherein the acetyl-leucine is acetyl-DL-leucine.

4. The method according to claim 1, wherein the acetyl-leucine has an enantiomeric excess of the L-enantiomer or the D-enantiomer.

5. The method according to claim 1, wherein therapeutically effective amount ranges from about 1 g to about 15 g per day.

6. A method of delaying onset of a neurodegenerative disease that would otherwise be expected to manifest according to typical disease progression in a subject in need thereof comprising: treating one or more symptoms of the neurodegenerative disease by administering a therapeutically effective amount of acetyl-leucine or a pharmaceutically acceptable salt thereof to the subject, wherein the one or more symptoms of the neurodegenerative disease is reduced sleep quality, and wherein the neurodegenerative disease is chosen from multiple system atrophy (MSA-P/MSA-C), Parkinson's Disease, Lewy Body dementia, and frontotemporal dementia with parkinsonism.

7. The method according to claim 6, wherein the reduced sleep quality is REM Sleep Behavior Disorder (RBD).

8. The method according to claim 6, wherein the one or more symptoms of the neurodegenerative disease further comprises motor function, cognitive impairment, autonomic dysfunction, and combinations thereof.

9. The method according to claim 6, wherein the acetyl-leucine is acetyl-DL-leucine.

10. The method according to claim 6, wherein the acetyl-leucine has an enantiomeric excess of the L-enantiomer or the D-enantiomer.

11. The method according to claim 6, wherein therapeutically effective amount ranges from about 1 g to about 15 g per day.

12. A method of delaying progression of a neurodegenerative disease in a subject in need thereof over time as compared to typical disease progression comprising: treating one or more symptoms of the neurodegenerative disease by administering a therapeutically effective amount of the acetyl-leucine or a pharmaceutically acceptable salt thereof to the subject for a duration chosen from at least about 3 months, at least about 6 months, at least about 1 year, at least about 2 years, and at least about 5 years, wherein one or more symptoms of the neurodegenerative disease is reduced sleep quality, and wherein the neurodegenerative disease is chosen from multiple system atrophy (MSA-P/MSA-C), Parkinson's Disease, Lewy Body dementia, and frontotemporal dementia with parkinsonism.

13. The method according to claim 12, wherein the reduced sleep quality is REM Sleep Behavior Disorder (RBD).

14. The method according to claim 12, wherein the acetyl-leucine is acetyl-DL-leucine.

15. The method according to claim 12, wherein the acetyl-leucine has an enantiomeric excess of the L-enantiomer or the D-enantiomer.

16. The method according to claim 6, wherein the acetyl-leucine is acetyl-L-leucine.

17. The method according to claim 1, wherein the acetyl-leucine is acetyl-L-leucine.

18. The method according to claim 12, wherein the acetyl-leucine is acetyl-L-leucine.

* * * * *